United States Patent
Kim et al.

(10) Patent No.: US 10,326,086 B2
(45) Date of Patent: *Jun. 18, 2019

(54) ORGANOMETALLIC COMPOUND, COMPOSITION CONTAINING THE ORGANOMETALLIC COMPOUND, AND ORGANIC LIGHT-EMITTING DEVICE INCLUDING THE ORGANOMETALLIC COMPOUND OR COMPOSITION

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Wook Kim, Hwaseong-si (KR); Changho Noh, Suwon-si (KR); Rupasree Ragini Das, Suwon-si (KR); Youngseok Park, Seoul (KR); Hyejin Bae, Suwon-si (KR); Miyoung Chae, Suwon-si (KR); Dmitry Kravchuk, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 501 days.

This patent is subject to a terminal disclaimer.

(21) Appl. No.: 15/013,404

(22) Filed: Feb. 2, 2016

(65) Prior Publication Data
US 2016/0233441 A1 Aug. 11, 2016

(30) Foreign Application Priority Data

Feb. 6, 2015 (KR) .................. 10-2015-0018868
Jan. 29, 2016 (KR) .................. 10-2016-0011879

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/025* (2013.01);
(Continued)

(58) Field of Classification Search
CPC ........... H01L 51/0085; H01L 51/0067; H01L 51/5016; H01L 51/006; H01L 51/0072;
(Continued)

(56) References Cited

U.S. PATENT DOCUMENTS 7,585,573 B2 9/2009 Lee et al.
7,897,421 B2 3/2011 Suzuri et al.
(Continued)

FOREIGN PATENT DOCUMENTS

DE 102013208026 A1 11/2013
EP 2562229 A1 8/2012
(Continued)

OTHER PUBLICATIONS

Ruben Seifert et al. "Chemical degradation mechanisms of highly efficient blue phosphorescent emitters used for organic light emitting diodes" Organic Electronics 14 (2013) 115-123.
(Continued)

Primary Examiner — Eli D. Strah
(74) Attorney, Agent, or Firm — Cantor Colburn LLP

(57) ABSTRACT

An organometallic compound represented by Formula 1:

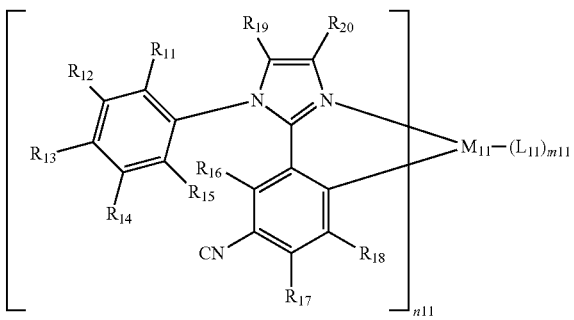

Formula 1 wherein, in Formula 1, groups an variables are the same as described in the specification.

22 Claims, 1 Drawing Sheet

(51) Int. Cl.
 *C07F 15/00* (2006.01)
 *C09K 11/02* (2006.01)
 *H01L 51/50* (2006.01)
(52) U.S. Cl.
 CPC .......... *C09K 11/06* (2013.01); *H01L 51/0067* (2013.01); *B32B 2457/206* (2013.01); *C09K 2211/1007* (2013.01); *C09K 2211/1044* (2013.01); *C09K 2211/1088* (2013.01); *C09K 2211/185* (2013.01); *H01L 51/006* (2013.01); *H01L 51/0072* (2013.01); *H01L 51/0094* (2013.01); *H01L 51/5004* (2013.01); *H01L 51/5012* (2013.01); *H01L 51/5016* (2013.01); *H01L 2251/552* (2013.01)
(58) Field of Classification Search
 CPC .......... H01L 51/5004; H01L 51/0094; H01L 51/5012; H01L 2251/552; C07F 15/0033; C09K 11/025; C09K 11/06; C09K 2211/1088; C09K 2211/185; C09K 2211/1044; C09K 2211/1007; B32B 2457/202

See application file for complete search history.

(56) References Cited

U.S. PATENT DOCUMENTS

| | | | |
|---|---|---|---|
| 8,142,909 B2 | 3/2012 | Beers et al. | |
| 8,148,891 B2 | 4/2012 | Tung et al. | |
| 9,024,308 B2 | 5/2015 | Bold et al. | |
| 9,184,399 B2 | 11/2015 | Dyatkin et al. | |
| 9,735,376 B2 * | 8/2017 | Choi | H01L 51/0085 |
| 2005/0008895 A1 | 1/2005 | Takada et al. | |
| 2008/0233433 A1 * | 9/2008 | Igarashi | C09K 11/06 428/704 |
| 2008/0281098 A1 | 11/2008 | Lamansky et al. | |
| 2010/0270916 A1 | 10/2010 | Xia et al. | |
| 2013/0032766 A1 | 2/2013 | Molt et al. | |
| 2013/0049576 A1 | 2/2013 | Katakura et al. | |
| 2013/0168656 A1 | 7/2013 | Tsai et al. | |
| 2013/0200340 A1 | 8/2013 | Otsu et al. | |
| 2014/0054563 A1 | 2/2014 | Xia et al. | |
| 2014/0073076 A1 | 3/2014 | D'Andrade et al. | |
| 2016/0028024 A1 * | 1/2016 | Das | H01L 51/0085 257/40 |
| 2016/0233440 A1 * | 8/2016 | Bae | H01L 51/0085 |
| 2016/0380214 A1 * | 12/2016 | Rai | C09K 11/025 257/40 |

FOREIGN PATENT DOCUMENTS

| | | | | |
|---|---|---|---|---|
| JP | 2008069221 A | * | 3/2008 | |
| KR | 2007-0050859 A | | 5/2007 | |
| KR | 2014-0026282 A | | 3/2014 | |
| WO | 2002-015645 A1 | | 2/2002 | |
| WO | 2005-019373 A2 | | 3/2005 | |
| WO | 2006-009024 A1 | | 1/2006 | |
| WO | 2012-170463 A1 | | 12/2012 | |
| WO | 2012-170571 A1 | | 12/2012 | |
| WO | WO-2012170463 A1 | * | 12/2012 | .......... C07F 15/0033 |
| WO | 2013-061850 A1 | | 5/2013 | |

OTHER PUBLICATIONS

Extended Search Report for European Patent Application No. 16154171.9 issued by the European Patent Office, dated Jul. 6, 2016.

* cited by examiner

ORGANOMETALLIC COMPOUND, COMPOSITION CONTAINING THE ORGANOMETALLIC COMPOUND, AND ORGANIC LIGHT-EMITTING DEVICE INCLUDING THE ORGANOMETALLIC COMPOUND OR COMPOSITION

CROSS-REFERENCE TO RELATED APPLICATIONS

This application claims priority to and the benefit of Korean Patent Application No. 10-2015-0018868, filed on Feb. 6, 2015, in the Korean Intellectual Property Office, and Korean Patent Application No. 10-2016-0011879, filed on Jan. 29, 2016, in the Korean Intellectual Property Office, the contents of which are incorporated herein in their entirety by reference.

BACKGROUND

1. Field

The present disclosure relates to an organometallic compound, a composition containing the organometallic compound, and an organic light-emitting device including the organometallic compound or the composition.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state to thereby generate light.

Different types of organic light emitting devices are known. However, there still remains a need in OLEDs having low driving voltage, high efficiency, high brightness, and long lifespan.

SUMMARY

Provided are a novel organometallic compound, a composition containing the novel organometallic compound, and an organic light-emitting devices including the organometallic compound or the composition.

Additional aspects will be set forth in part in the description which follows and, in part, will be apparent from the description, or may be learned by practice of the presented embodiments.

According to an aspect of the present invention, there is provided an organometallic compound represented by Formula 1:

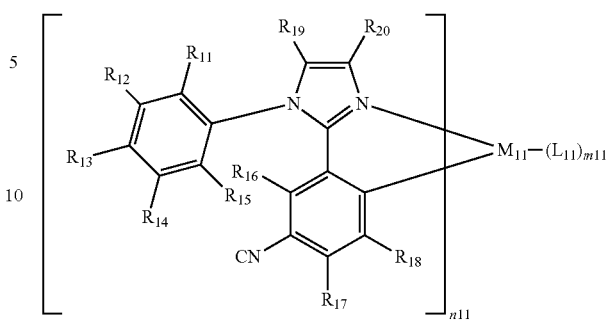

Formula 1 wherein, in Formula 1, $M_{11}$ is selected from a first-row transition metal, a second-row transition metal, and a third-row transition metal;

$R_{11}$ to $R_{18}$ are each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group; a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

optionally, adjacent two of $R_{11}$ to $R_{15}$ are linked to form a substituted or unsubstituted saturated ring, or a substituted or unsubstituted unsaturated ring;

at least one of $R_{11}$ to $R_{15}$ is selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group; a substituted or unsubstituted $C_6$-$C_{30}$ arylthio group, a substituted or unsubstituted $C_7$-$C_{30}$ arylalkyl group, a substituted or unsubstituted heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{19}$ and $R_{20}$ are each independently selected from a hydrogen, a deuterium, a $C_1$-$C_{30}$ alkyl group, and a deuterium-substituted $C_1$-$C_{30}$ alkyl group;

at least one of $R_{11}$ to $R_{23}$ is a deuterium-containing substituent;

n11 is selected from 1, 2, and 3;

$L_{11}$ is selected from a monodentate ligand and a bidentate ligand; and m11 is selected from 0, 1, 2, 3, and 4.

According to another aspect of the present invention, an organometallic compound-containing composition includes:

a first organometallic compound represented by Formula 1 and a second organometallic compound represented by Formula 2:

Formula 1

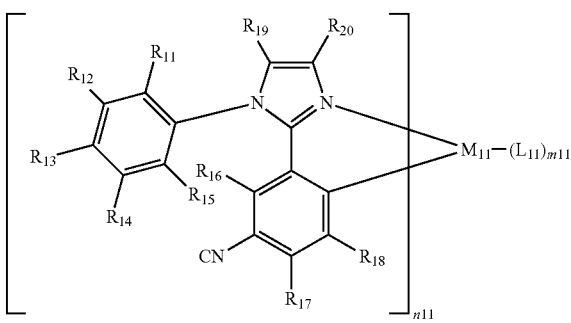

Formula 2

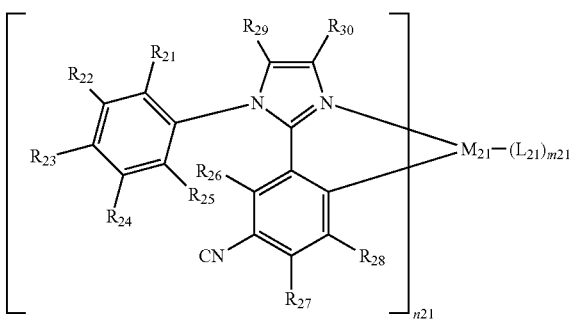

wherein, in Formulae 1 and 2, $R_{11}$ to $R_{18}$ are each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

optionally, adjacent two of $R_{11}$ to $R_{15}$ are linked to form a substituted or unsubstituted saturated ring, or a substituted or unsubstituted unsaturated ring;

at least one of $R_{11}$ to $R_{15}$ is selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{19}$ and $R_{20}$ are each independently selected from a hydrogen; a deuterium, a $C_1$-$C_{30}$ alkyl group, and a deuterium-substituted $C_1$-$C_{30}$ alkyl group;

at least one of $R_{11}$ to $R_{20}$ is a deuterium-containing substituent;

$R_{21}$ to $R_{28}$ are each independently selected from a hydrogen, —F, —Cl, —Br, —I, a hydroxyl group, a cyano group, a nitro group, a carbonyl group, an amino group, an amidino group; a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted alkylsilyl group;

optionally, adjacent two of $R_{21}$ to $R_{25}$ are linked to form a substituted or unsubstituted saturated ring, or a substituted or unsubstituted unsaturated ring;

at least one of $R_{21}$ to $R_{25}$ is selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{29}$ and $R_{30}$ are each independently selected from a hydrogen and a $C_1$-$C_{30}$ alkyl group;

$R_{21}$ to $R_{30}$ are a deuterium-non-containing substituent;

$M_{11}$ and $M_{21}$ are each independently selected from a first-row transition metal, a second-row transition metal, and a third-row transition metal;

n11 and n21 are each independently selected from 1, 2, and 3;

$L_{11}$ and $L_{21}$ are each independently selected from a monodentate ligand and a bidentate ligand; and m11 and m21 are each independently selected from 0, 1, 2, 3, and 4.

According to another aspect of the present inventive concept, an organic light-emitting device includes:

a first electrode;

a second electrode; and an organic layer disposed between the first electrode and the second electrode, wherein the organic layer includes an emission layer and at least one organometallic compound of Formula 1, or wherein the above-described organometallic compound-containing composition includes a first organometallic compound represented by Formula 1 described above and a second organometallic compound represented by Formula 2 described above.

The emission layer may include the organometallic compound or the organometallic compound-containing composition. The emission layer may further include a host, and the organometallic compound in the emission layer may serve as a dopant.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
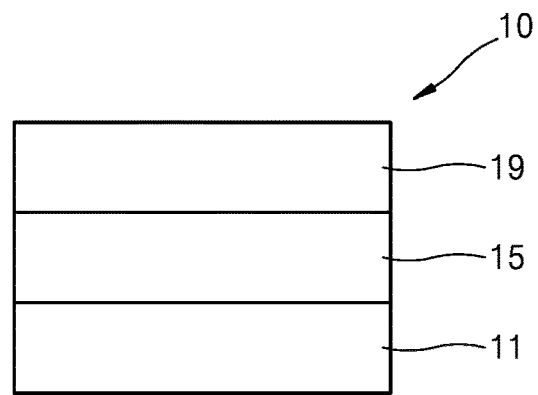
FIG. 1 is a schematic cross-sectional view illustrating an organic light-emitting device according to an embodiment.
Figure 2:
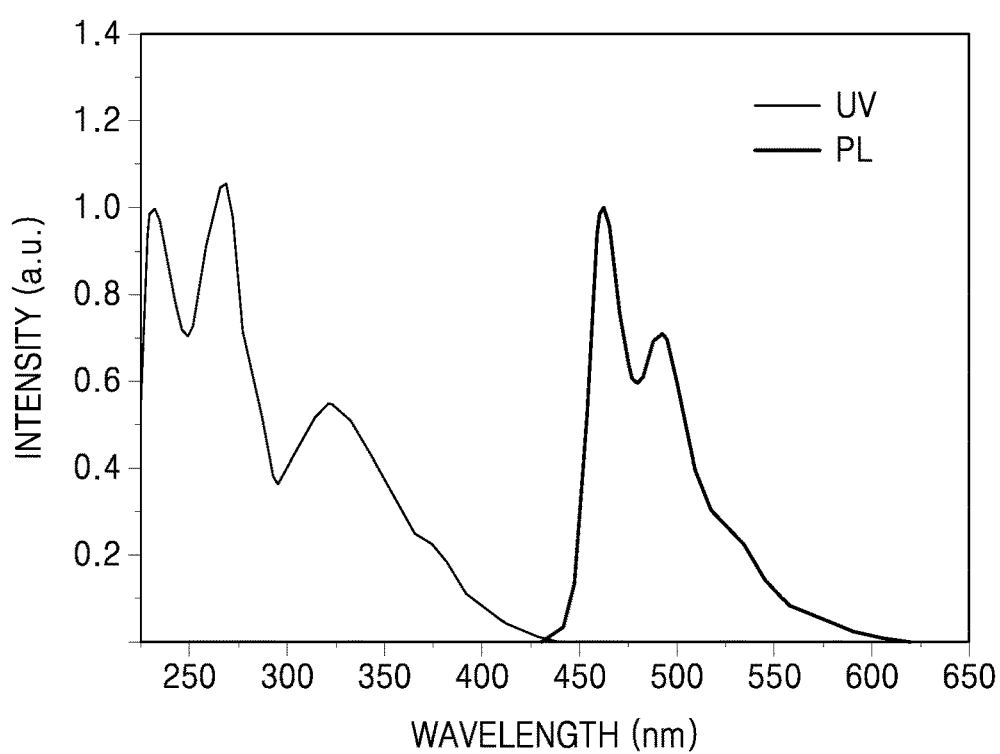
FIG. 2 is a graph of intensity (arbitrary unit, a. u.) versus wavelength (nanometers, nm) illustrating photoluminescent (PL) spectra and ultraviolet (UV) absorption spectra of Compound BD040 according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an aspect of the present disclosure, there is provided an organometallic compound represented by Formula 1:

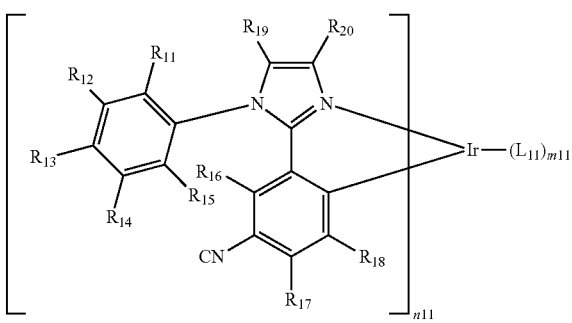

Formula 1

In Formula 1, $M_{11}$ may be selected from a first-row transition metal, a second-row transition metal, and a third-row transition metal.

For example, in Formula 1, $M_{11}$ may be selected from iridium (Ir), platinum (Pt), osmium (Os), ruthenium (Ru), rhodium (Rh), palladium (Pd), copper (Cu), silver (Ag), gold (Au), titanium (Ti), zirconium (Zr), hafnium (Hf), europium (Eu), terbium (Tb), and thulium (Tm). However, embodiments are not limited thereto.

In some embodiments, in Formula 1, $M_{11}$ may be selected from Ir, Pt, and Os, but is not limited thereto.

In some other embodiments, in Formula 1, $M_{11}$ may be selected from Ir and Pt, but is not limited thereto.

In Formula 1, $R_{11}$ to $R_{18}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{1e}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group, wherein optionally, adjacent two of $R_{11}$ to $R_{15}$ may be linked to form a substituted or unsubstituted saturated ring, or a substituted or unsubstituted unsaturated ring.

For example, in Formula 1, $R_{11}$ to $R_{18}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group, wherein optionally, adjacent two of $R_{11}$ to $R_{15}$ may be linked to form a substructure represented by Formula 10. However, embodiments are not limited thereto.

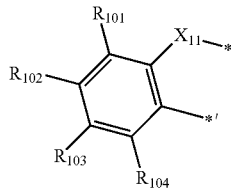

Formula 10

In Formula 10, $X_{11}$ may be selected from O, S, and $N(R_{105})$;

$R_{101}$ to $R_{105}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group; and

* and *' may be each independently a carbon atom to which adjacent two of $R_{11}$ to $R_{15}$ are bound.

In some embodiments, in Formula 1, $R_{11}$ to $R_{18}$ may be each independently selected from a hydrogen, a deuterium, —F, —Cl, —Br, —I, a cyano group, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group, wherein optionally, adjacent two of $R_{11}$ to $R_{15}$ may be linked to form a substructure represented by Formula 10. However, embodiments are not limited thereto.

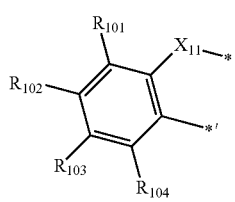

Formula 10

In Formula 10, $X_{11}$ may be selected from O, S, and $N(R_{105})$;

$R_{101}$ to $R_{105}$ may be each independently selected from a hydrogen, a deuterium, —F, —Cl, —Br, —I, a cyano group, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group;

* and *' may be each independently a carbon atom to which adjacent two of $R_{11}$ to $R_{15}$ are bound.

In some embodiments, in Formula 1, $R_{11}$ to $R_{18}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, and —Si($Q_1$)($Q_2$)($Q_3$), a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group, a phenyl group, a biphenyl group, a terphenyl group, a naphthyl group, a phenanthrenyl group, an anthracenyl group, a triphenylenyl group, a pyrenyl group, and a chrysenyl group, each substituted with at least one of a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, and —Si($Q_4$)($Q_5$)($Q_6$), wherein $Q_1$ to $Q_3$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group; and $Q_4$ to $Q_6$ may be each independently selected from
a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, and a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I and a cyano group;

at least one of $Q_4$ to $Q_6$ may be selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group; and optionally, adjacent two of $R_{11}$ to $R_{15}$ may be linked to form a substructure represented by Formula 10. However, embodiments are not limited thereto.

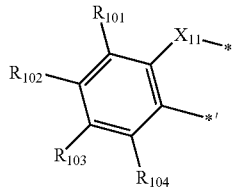

Formula 10

In Formula 10, $X_{11}$ may be selected from 0, 3, and $N(R_{105})$;

$R_{101}$ to $R_{105}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group; and

* and *' may be each independently a carbon atom to which adjacent two of $R_{11}$ to $R_{15}$ are bound.

In some embodiments, in Formula 1, $R_{11}$ to $R_{18}$ may be each independently selected from a hydrogen, a deuterium, —F, —Cl, —Br, —I, a cyano group, a methyl group, an iso-propyl group, an iso-butyl group, a tert-butyl group, a neo-pentyl group, a phenyl group, a biphenyl group, and —Si($Q_1$)($Q_2$)($Q_3$), a methyl group, an iso-propyl group, an iso-butyl group, a tert-butyl group, and a neo-pentyl group, each substituted with at least one of a deuterium, —F, —Cl, —Br, —I, and a cyano group, a phenyl group and a biphenyl group, each substituted with at least one of a deuterium, —F, —Cl, —Br, —I, a cyano group, a methyl group, an iso-propyl group, an iso-butyl group, a tert-butyl group, and a neo-pentyl group, and —Si($Q_4$)($Q_5$)($Q_6$);

$Q_1$ to $Q_3$ may be each independently selected from a methyl group, an iso-propyl group, an iso-butyl group, a tert-butyl group, and a neo-pentyl group;

$Q_4$ to $Q_6$ may be each independently selected from a methyl group, an iso-propyl group, an iso-butyl group, a tert-butyl group, and a neo-pentyl group, and a methyl group, an iso-propyl group, an iso-butyl group, a tert-butyl group, and a neo-pentyl group, each substituted with at least one of a deuterium, —F, —Cl, —Br, —I and a cyano group;

at least one of $Q_4$ to $Q_6$ may be selected from a methyl group, an iso-propyl group, an iso-butyl group, a tert-butyl group, and a neo-pentyl group, each substituted with at least one of a deuterium, —F, —Cl, —Br, —I and a cyano group; and optionally, $R_{12}$ and $R_{13}$ may be linked to form a substructure represented by Formula 10. However, embodiments are not limited thereto,

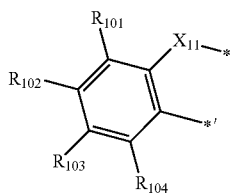

Formula 10

In Formula 10, $X_{11}$ may be selected from O, S, and $N(R_{105})$:

$R_{101}$ to $R_{105}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group; and

* and *' may be each independently a carbon atom to which $R_{12}$ and $R_{13}$ are bound.

In some embodiments, in Formula 1, $R_{11}$ to $R_{19}$ may be each independently selected from a hydrogen, a deuterium, a methyl group, an iso-propyl group, an iso-butyl group, a tert-butyl group, a neo-pentyl group, a phenyl group, a biphenyl group, and —Si(CH$_3$)$_3$, a methyl group, an iso-propyl group, an iso-butyl group, a tert-butyl group; and a neo-pentyl group, each substituted with a deuterium, a phenyl group and a biphenyl group, each substituted with a deuterium, and —Si(CD$_3$)$_3$; and optionally, $R_{12}$ and $R_{13}$ may be linked to form a substructure represented by Formula 10. However, embodiments are not limited thereto.

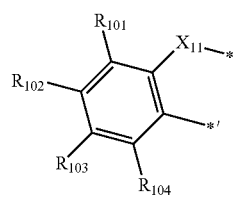

Formula 10

In Formula 10, $X_{11}$ may be selected from O, S, and $N(R_{105})$:

$R_{101}$ to $R_{105}$ may be each independently selected from a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group; and

* and *' may be each independently a carbon atom to which $R_{12}$ and $R_{13}$ are bound.

In some embodiments, in Formula 1, at least one of $R_{11}$ to $R_{15}$ may be selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_5$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group.

For example, in Formula 1, at least one of $R_{11}$ to $R_{15}$ may be selected from a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group, but is not limited thereto.

In some embodiments, in Formula 1, at least one of $R_{11}$ to $R_{15}$ may be selected from a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group. However, embodiments are not limited thereto.

In some other embodiments, in Formula 1, at least one of $R_{11}$ to $R_{15}$ may be selected from an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, and —Si(Q$_1$)(Q$_2$)(Q$_3$), an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group, a phenyl group, a biphenyl group, a terphenyl group, a naphthyl group, a phenanthrenyl group, an anthracenyl group, a triphenylenyl group, a pyrenyl group, and a chrysenyl group, each substituted with at least one of a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, and —Si(Q$_4$)(Q$_5$)(Q$_6$), wherein Q$_1$ to Q$_3$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group;

$Q_4$ to $Q_6$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, and a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group; and at least one of $Q_4$ to $Q_6$ may be selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group. However, embodiments are not limited thereto.

In some other embodiments, in Formula 1, at least one of $R_{11}$ to $R_{15}$ may be selected from an iso-propyl group, an iso-butyl group, a tert-butyl group, a neo-pentyl group, a phenyl group, a biphenyl group, and —Si($Q_1$)($Q_2$)($Q_3$), an iso-propyl group; an iso-butyl group; a tert-butyl group, and a neo-pentyl group, each substituted with at least one of a deuterium, —F, —Cl, —Br, —I, and a cyano group, a phenyl group and a biphenyl group, each substituted with at least one of a deuterium, —F, —Cl, —Br, —I, a cyano group, a methyl group, an iso-propyl group, an iso-butyl group, a tert-butyl group, and a neo-pentyl group; and —Si($Q_4$)($Q_5$)($Q_6$), wherein $Q_1$ to $Q_3$ may be each independently a methyl group, an iso-propyl group, an iso-butyl group, a tert-butyl group, and a neo-pentyl group;

$Q_4$ to $Q_6$ may be each independently selected from a methyl group, an iso-propyl group, an iso-butyl group, a tert-butyl group, and a neo-pentyl group, and a methyl group, an iso-propyl group, an iso-butyl group, a tert-butyl group, and a neo-pentyl group, each substituted with at least one of a deuterium, —F, —Cl, —Br, —I and a cyano group; and at least one of $Q_4$ to $Q_6$ may be selected from a methyl group, an iso-propyl group, an iso-butyl group; a tert-butyl group, and a neo-pentyl group, each substituted with at least one of a deuterium, —F, —Cl, —Br, —I, and a cyano group. However, embodiments are not limited thereto.

In some other embodiments, in Formula 1, at least one of $R_{11}$ to $R_{15}$ may be selected from an iso-propyl group, an iso-butyl group, a tert-butyl group, a neo-pentyl group, a phenyl group, a biphenyl group, and —Si($Q_1$)($Q_2$)($Q_3$), an iso-propyl group; an iso-butyl group; a tert-butyl group, and a neo-pentyl group, each substituted with at least one of a deuterium, —F, —Cl, —Br, —I, and a cyano group, a phenyl group and a biphenyl group, each substituted with at least one of a deuterium, —F, —Cl, —Br, —I, a cyano group, a methyl group, an iso-propyl group, an iso-butyl group, a tert-butyl group, and a neo-pentyl group, and —Si($Q_4$)($Q_5$)($Q_6$);

$Q_1$ to $Q_3$ may be each independently selected from a methyl group, an iso-propyl group, an iso-butyl group, a tert-butyl group, and a neo-pentyl group;

$Q_4$ to $Q_6$ may be each independently selected from a methyl group, an iso-propyl group, an iso-butyl group, a tert-butyl group, and a neo-pentyl group, and a methyl group, an iso-propyl group, an iso-butyl group, a tert-butyl group, and a neo-pentyl group, each substituted with at least one of a deuterium, —F, —Cl, —Br, —I and a cyano group; and at least one of $Q_4$ to $Q_6$ may be selected from a methyl group, an iso-propyl group, an iso-butyl group, a tert-butyl group, and a neo-pentyl group, each substituted with at least one of a deuterium, —F, —Cl, —Br, —I, and a cyano group. However, embodiments are not limited thereto.

In some other embodiments, in Formula 1, at least one of $R_{11}$ to $R_{15}$ may be selected from an iso-propyl group, an iso-butyl group, a tert-butyl group, a neo-pentyl group, a phenyl group, a biphenyl group, and —Si(CH$_3$)$_3$, an iso-propyl group, an iso-butyl group, a tert-butyl group, and a neo-pentyl group, each substituted with a deuterium, a phenyl group, and a biphenyl group, each substituted with a deuterium, and —Si(CD$_3$)$_3$. However, embodiments are not limited thereto.

In some embodiments, in Formula 1, $R_{11}$ and $R_{12}$, $R_{12}$ and $R_{13}$, $R_{13}$ and $R_{14}$, or $R_{14}$ and $R_{15}$ may be optionally linked to each other to form a condensed ring. However, embodiments are not limited thereto.

In some embodiments, in Formula 1, $R_{15}$ and $R_{15}$ may be optionally linked to each other via a single bond. However, embodiments are not limited thereto.

In Formula 1, $R_{19}$ and $R_{20}$ may be each independently selected from a hydrogen, a deuterium, a $C_1$-$C_{30}$ alkyl group, and a deuterium-substituted $C_1$-$C_{30}$ alkyl group.

For example, in Formula 1, $R_{19}$ and $R_{20}$ may be each independently selected from a hydrogen;

a deuterium;

a methyl group, an ethyl group, an n-propyl group, an iso-propyl group, an n-butyl group, a sec-butyl group; an iso-butyl group, and a tert-butyl group; and a methyl group, an ethyl group, an n-propyl group, an iso-propyl group, an n-butyl group, a sec-butyl group, an iso-butyl group, and a tert-butyl group, each substituted with a deuterium. However, embodiments are not limited thereto.

In some embodiments, in Formula 1, $R_{19}$ and $R_{20}$ may be each independently selected from a hydrogen and a deuterium. However, embodiments are not limited thereto.

In some embodiments, in Formula 1, $R_{19}$ may be a deuterium, and $R_{20}$ may be a hydrogen. However, embodiments are not limited thereto.

In some embodiments, in Formula 1, $R_{19}$ may be a hydrogen, and $R_{20}$ may be a deuterium. However, embodiments are not limited thereto, In some embodiments, in Formula 1, $R_{19}$ and $R_{20}$ may be both a deuterium. However, embodiments are not limited thereto.

In Formula 1, at least one of $R_{11}$ to $R_{20}$ may be a deuterium-containing substituent.

As used herein, the term "deuterium-containing substituent" refers to a deuterium or a substituent that contains at least one deuterium. For example, a deuterium-containing substituent may refer to a substituent that is obtained by substituting at least one hydrogen atom in a substituent such as a $C_1$-$C_{30}$ alkyl group, a $C_6$-$C_{30}$ aryl group, or the like as described above with a deuterium atom.

For example, in Formula 1, the deuterium-containing substituent may be selected from a deuterium, and a $C_1$-$C_{30}$ alkyl group, a $C_3$-$C_{30}$ branched alkyl group; a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, and a $C_1$-$C_{30}$ alkylsilyl group, each substituted with a deuterium. However, embodiments are not limited thereto.

In some embodiments, in Formula 1, the deuterium-containing substituent may be selected from a deuterium, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group, each substituted with a deuterium, and —Si($Q_4$)($Q_5$)($Q_6$), wherein $Q_4$ to $Q_6$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, and a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group, wherein at least one of $Q_4$ to $Q_6$ may be selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium. However, embodiments are not limited thereto.

In some embodiments, in Formula 1, the deuterium-containing substituent may be selected from a deuterium, and a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, a phenyl group, a biphenyl group, a terphenyl group, a naphthyl group, a phenanthrenyl group, an anthracenyl group, a triphenylenyl group, a pyrenyl group, and a chrysenyl group, each substituted with a deuterium. However, embodiments are not limited thereto.

In some embodiments, in Formula 1, the deuterium-containing substituent may be selected from -D, —$CH_2D$, —$CHD_2$, —$CD_3$, —$CH_2CH_2D$, —$CH_2CHD_2$, —$CH_2CD_3$, —$CHDCH_3$, —$CHDCH_2D$, —$CHDCHD_2$, —$CHDCD_3$, —$CD_2CH_3$, —$CD_2CH_2D$, —$CD_2CHD_2$, —$CD_2CD_3$, —$CH_2CH_2CH_2D$, —$CH_2CH_2CHD_2$, —$CH_2CH_2CD_3$, —$CH_2CHDCH_3$, —$CH_2CHDCH_2D$, —$CH_2CHDCHD_2$, —$CH_2CHDCD_3$, —$CH_2CD_2CH_3$, —$CH_2CD_2CH_2D$, —$CH_2CD_2CHD_2$, —$CH_2CD_2CD_3$, —$CHDCH_2CH_2D$, —$CHDCH_2CHD_2$, —$CHDCH_2CD_3$, —$CHDCHDCH_3$, —$CHDCHDCH_2D$, —$CHDCHDCHD_2$, —$CHDCHDCD_3$, —$CHDCD_2CH_3$, —$CHDCD_2CH_2D$, —$CHDCD_2CHD_2$, —$CHDCD_2CD_3$, —$CD_2CH_2CH_2D$, —$CD_2CH_2CHD_2$, —$CD_2CH_2CD_3$, —$CD_2CHDCH_3$, —$CD_2CHDCH_2D$, —$CD_2CHDCHD_2$, —$CD_2CHDCD_3$, —$CD_2CD_2CH_3$, —$CD_2CD_2CH_2D$, —$CD_2CD_2CHD_2$, —$CD_2CD_2CD_3$, —$CH(CH_3)(CH_2D)$, —$CH(CH_3)(CHD_2)$, —$CH(CH_2D)(CH_2D)$, —$CH(CH_3)(CD_3)$, —$CH(CHD_2)(CHD_2)$, —$CH(CH_2D)(CD_3)$, —$CH(CHD_2)(CHD_2)$, —$CH(CHD_2)(CD_3)$, —$CH(CD_3)_2$, —$CD(CH_3)_2$, —$CD(CH_3)(CH_2D)$, —$CD(CH_3)(CHD_2)$, —$CD(CH_2D)(CH_2D)$, —$CD(CH_3)(CD_3)$, —$CD(CHD_2)(CHD_2)$, —$CD(CH_2D)(CD_3)$, —$CD(CHD_2)(CHD_2)$, —$CD(CHD_2)(CD_3)$, —$CD(CD_3)_2$, —$CD_2CD(CD_3)_2$, —$C(CD_3)_3$, —$CD_2C(CD_3)_3$; and groups represented by Formulae 3-1 to 3-5. However, embodiments are not limited thereto.

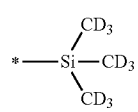

3-1

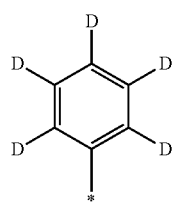

3-2

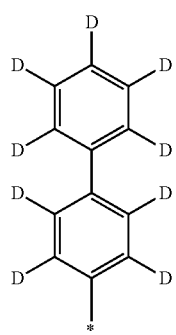

3-3

3-4

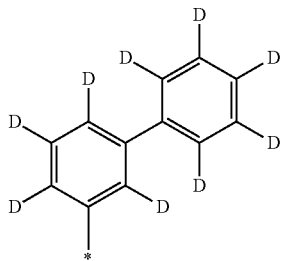

3-5

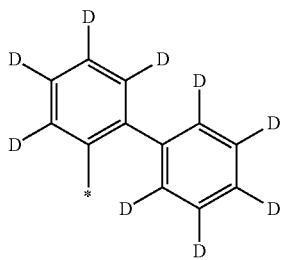

In Formulae 3-1 to 3-5, may be a binding site to an adjacent atom.

In some embodiments, in Formula 1, the deuterium-containing substituent may be selected from -D, —CH$_2$D, —CHD$_2$, —CD$_3$, —CH(CH$_3$)(CH$_2$D), —CH(CH$_3$)(CHD$_2$), —CH(CH$_2$D)$_2$, —CH(CH$_3$)(CD$_3$), —CH(CHD)(CHD$_2$), —CH(CH$_2$D)(CD$_3$), —CH(CHD$_2$)$_2$, —CH(CHD$_2$)(CD$_3$), —CH(CD$_3$)$_2$, —CD(CH$_3$)$_2$, —CD(CH$_3$)(CH$_2$D), —CD(CH$_3$)(CHD$_2$), —CD(CH$_2$D)(CH$_2$D), —CD(CH$_3$)(CD$_3$), —CD(CHD)(CHD$_2$), —CD(CH$_2$D)(CD$_3$), —CD(CHD$_2$)$_2$, —CD(CHD$_2$)(CD$_3$), —CD(CD$_3$)$_2$, —CD$_2$CD(CD$_3$)$_2$, —C(CD$_3$)$_3$, —CD$_2$C(CD$_3$)$_3$; and groups represented by Formulae 3-1 to 3-5. However, embodiments are not limited thereto:

3-1

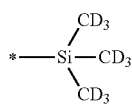

3-2

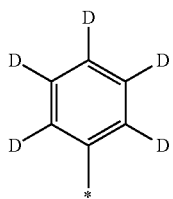

3-3

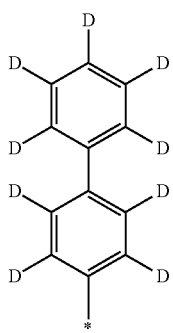

3-4

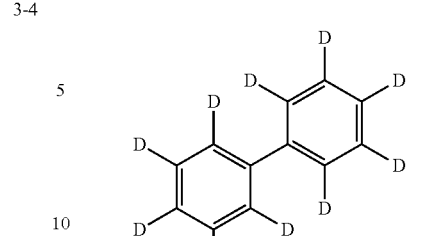

3-5

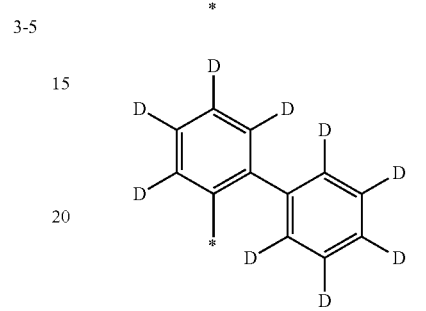

In Formulae 3-1 to 3-5, * may be a binding site to an adjacent atom.

In some other embodiments, in Formula 1, the deuterium-containing substituent may be selected from -D, —CH$_2$D, —CHD$_2$, —CD$_3$, —CD(CH$_3$)$_2$, —CD(CH$_3$)(CH$_2$D), —CD(CH$_3$)(CHD$_2$), —CD(CH$_3$)(CD$_3$), —CD(CH$_2$D)(CD$_3$), —CD(CHD$_2$)(CD$_3$), —CD(CD$_3$)$_2$, —CD$_2$CD(CD$_3$)$_2$, —C(CD$_3$)$_3$, —CD$_2$C(CD$_3$)$_3$, and groups represented by Formulae 3-1 to 3-5. However, embodiments are not limited thereto:

3-1

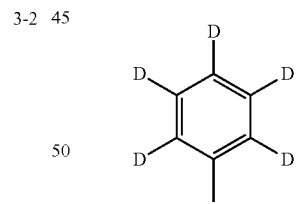

3-2

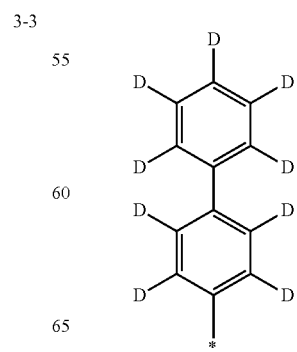

3-3

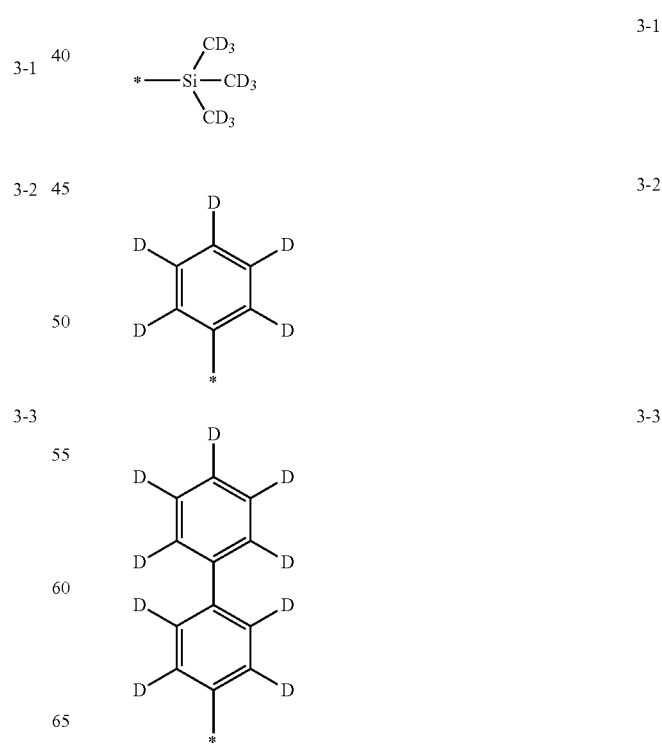

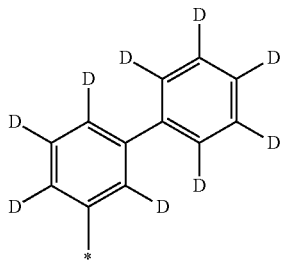

3-4

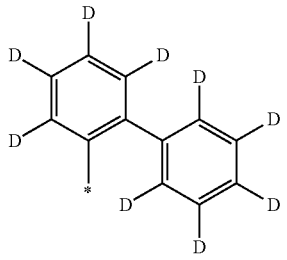

3-5

In Formulae 3-1 to 3-5, * may be a binding site to an adjacent atom.

In Formula 1, a moiety represented by

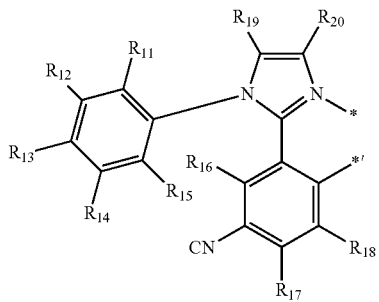

(wherein * and *' may be each a binding site to $M_{11}$ in Formula 1) may include at least one deuterium.

Whether the moiety represented by

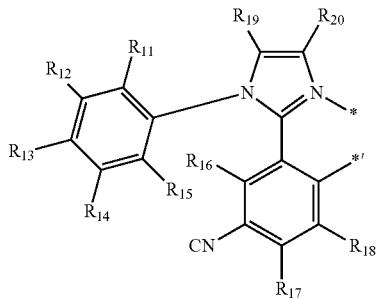

includes a deuterium or not may be identified by analyzing the $^1$H NMR spectrum or molecular weight measured using a molecular weight measurement device such as a matrix-assisted laser desorption-ionization-time-of-flight mass spectrometer.

For example, a compound (hereinafter referred to as a "first reference compound") having a backbone that is identical to that of the organometallic compound represented by Formula 1 but including no deuterium atom may be prepared. The $^1$H NMR spectra of the first reference compound and the organometallic compound represented by Formula 1 may be measured. Then, by comparing integral values of signals at a certain ppm in the measured spectra of the first reference compound and the organometallic compound with each other, the number of hydrogen atoms at certain positions (i.e., hydrogen atoms bound to certain carbons) in the organometallic compound represented by Formula 1 that are substituted with deuterium may be determined.

Alternatively, a compound (hereinafter referred to as a "second reference compound") having a backbone that is identical to that of the organometallic compound represented by Formula 1 and of which all hydrogen atoms are substituted with deuterium may be assumed. By comparing the calculated molecular weight of the second reference compound with the molecular weight of the organometallic compound represented by Formula 1, the number of hydrogen atoms in the organometallic compound represented by Formula 1 that are substituted with deuterium may be determined.

In some embodiments, the organometallic compound represented by Formula 1 may have a deuteration rate, which is determined by Equation 1 of 50% or more, but embodiments are not limited thereto:

$$\text{Deuteration rate } (\%) = n_{D1}/(n_{H1} + n_{D1}) \times 100 \quad \text{Equation 1}$$

In Equation 1, $n_{H1}$ indicates a total number of hydrogens included in the deuterium-containing substituents; and $n_{D1}$ indicates a total number of deuterium atoms included in the deuterium-containing substituents.

In some embodiments, a deuteration rate represented by Equation 1 of the organometallic compound represented by Formula 1 may be 70% or more, but embodiments are not limited thereto.

In some embodiments, a deuteration rate represented by Equation 1 of the organometallic compound represented by Formula 1 may be 90% or more, but embodiments are not limited thereto.

In Formula 1, n11 indicates the number of ligands represented by

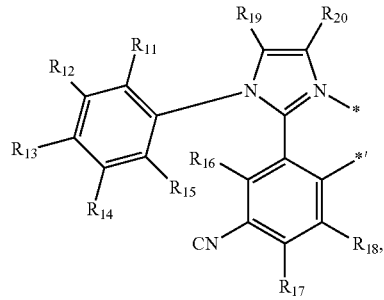

and n11 may be selected from 1, 2, and 3. When n11 is 2 or more, the ligands represented by

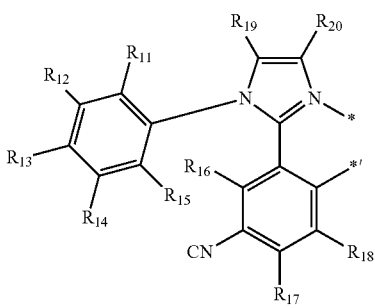

may be identical to or different from each other.

In some embodiments, in Formula 1, $M_{11}$ may be Ir; and n11 may be selected from 2 and 3. However, embodiments are not limited thereto.

In some other embodiments, in Formula 1, $M_{11}$ may be Pt; and n11 may be selected from 1 and 2. However, embodiments are not limited thereto.

In Formula 1, $L_{11}$ may be selected from a monodentate ligand and a bidentate ligand.

In some embodiments, in Formula 1, $L_{11}$ may be selected from monodentate ligands. For example, $L_{11}$ may be selected from I$^-$, Br$^-$, Cl$^-$, a sulfide, a nitrate, an azide, a hydroxide, a cyanate, an isocyanate, a thiocyanate, water, acetonitrile, a pyridine, ammonia, carbon monoxide, P(Ph)$_3$, P(Ph)$_2$CH$_3$, PPh(CH$_3$)$_2$, and P(CH$_3$)$_3$, but embodiments are not limited thereto.

In some embodiments, in Formula 1, $L_{11}$ may be selected from bidentate ligands. For example, $L_{11}$ may be selected from an oxalate, an acetylacetonate, a picolinic acid, a 1,2-bis(diphenylphosphino)ethane, a 1,1-bis(diphenylphosphino)methane, a glycinate, an ethylenediamine, and ligands represented by Formulae 4-1 to 4-4, but embodiments are not limited thereto:

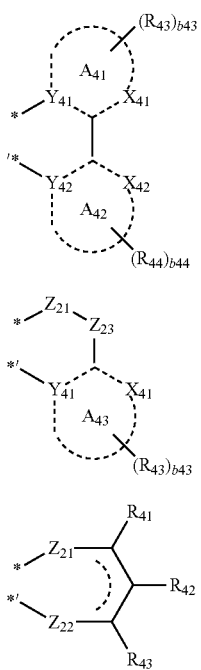

4-1

4-2

4-3

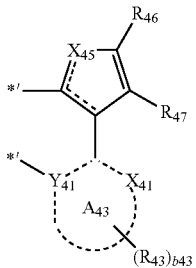

4-4

In Formulae 4-1 to 4-4, $X_{41}$ may be $CR_{41}$ or a nitrogen atom (N);

$X_{42}$ may be $CR_{42}$ or N;

$X_{45}$ may be O, S, or $N(R_{45})$;

$Y_{41}$ and $Y_{42}$ may be each independently a carbon (C) atom or N;

$Z_{21}$ and $Z_{22}$ may be each independently N, O, $N(R_{48})$, $P(R_{48})(R_{49})$, or $As(R_{48})(R_{49})$:

$Z_{23}$ may be CO or CH$_2$;

$A_{41}$ to $A_{43}$ may be each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arena, a $C_1$-$C_{10}$ heteroarene, a non-aromatic condensed polycycle, and a non-aromatic condensed heteropolycycle;

$R_{41}$ to $R_{49}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, a substituted or unsubstituted monovalent non-aromatic condensed polycyclic group, a substituted or unsubstituted monovalent non-aromatic condensed heteropolycyclic group, and —Si($Q_{41}$)($Q_{42}$)($Q_{43}$);

optionally, adjacent two of $R_{41}$ to $R_{44}$ are linked to form a substituted or unsubstituted saturated ring or a substituted or unsubstituted unsaturated ring;

optionally, $R_{46}$ and $R_{47}$ are linked to form a substituted or unsubstituted saturated ring or a substituted or unsubstituted unsaturated ring;

b43 and b44 may be each independently an integer selected from 1 to 5;

$Q_{41}$ to $Q_{43}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_6$-$C_{30}$ aryloxy group, a $C_6$-$C_{30}$ arylthio group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group; and

* and *' each independently indicate a binding site to $M_{11}$ in Formula 1

In some embodiments, in Formula 1, $L_{11}$ may be represented by one of Formulae 4-1 to 4-4;

$A_{41}$ to $A_{43}$ may be each independently selected from a benzene, a naphthalene, a fluorene, a spiro-fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole, and a triazine;

$R_{41}$ to $R_{47}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{23}$ alkyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, and —Si($Q_{41}$)($Q_{42}$)($Q_{43}$);

b43 and b44 may be each independently an integer selected from 1 to 3;

$Q_{41}$ to $Q_{43}$ may be each independently selected from a $C_1$-$C_{10}$ alkyl group, a phenyl group, a naphthyl group, a pyridinyl group, a pyrimidinyl group, and a triazinyl group;

optionally, adjacent two of $R_{41}$ to $R_{44}$ may be linked to form a substituted or unsubstituted saturated ring or a substituted or unsubstituted unsaturated ring;

optionally, $R_{48}$ and $R_{47}$ may be linked to form a substituted or unsubstituted saturated ring or a substituted or unsubstituted unsaturated ring. However, embodiments are not limited thereto.

In some embodiments, in Formula 1, $L_{11}$ may be represented by one of Formulae 4-1 to 4-4;

$A_{41}$ may be selected from a pyridine, an imidazole, a pyrazole, a triazole, and a tetrazole, $A_{42}$ may be selected from a benzene, a pyridine, a pyrazine, a pyrimidine, and a triazine, $A_{43}$ may be selected from a benzene and a pyridine;

$R_{41}$ to $R_{44}$ may be each independently selected from a hydrogen, —F, a cyano group, a nitro group, a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, a nitro group, and a methyl group; and b43 and b44 may be each independently an integer selected from 1 to 3. However, embodiments are not limited thereto.

In some embodiments, $L_{11}$ in Formula 1 may be represented by one of Formulae 5-1 to 5-122. However, embodiments are not limited thereto 5-1

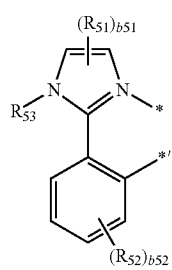

5-2

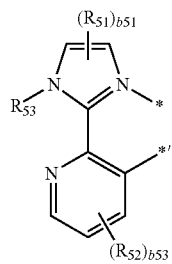

5-3

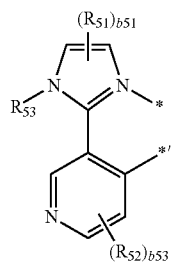

-continued 5-4

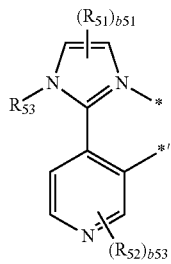

5-5

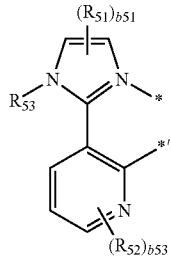

5-6

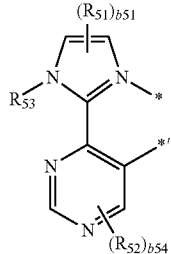

5-7

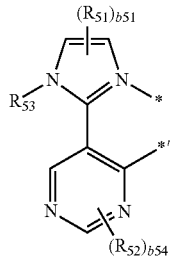

5-8

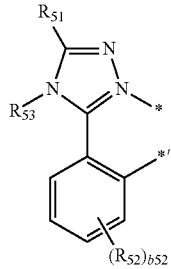

5-9

-continued

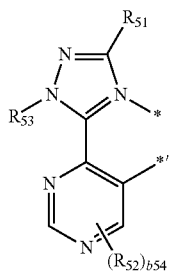
5-20
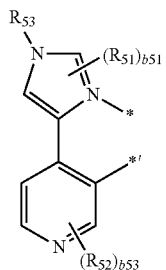
5-25
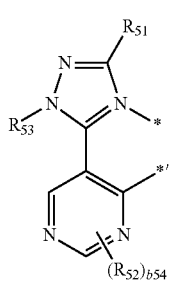
5-21
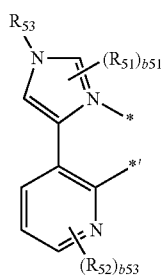
5-26
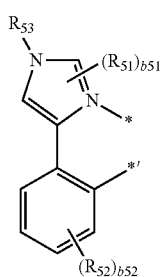
5-22
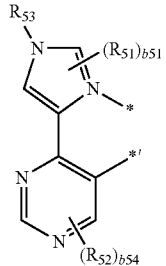
5-27
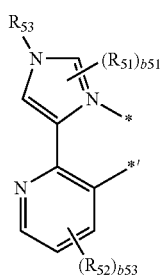
5-23
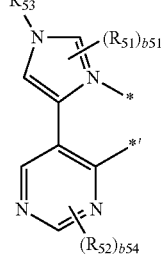
5-28
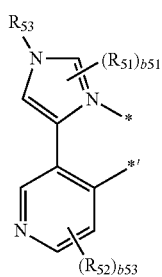
5-24
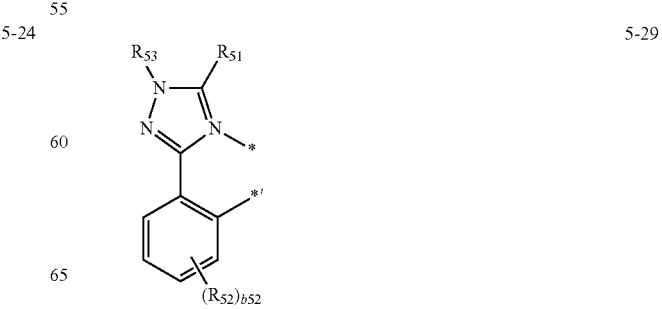
5-29

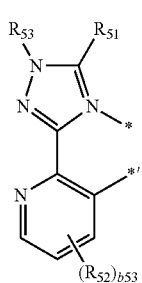
5-30
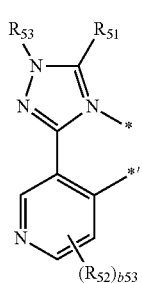
5-31
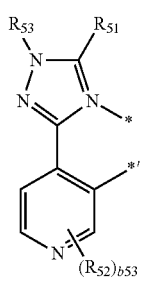
5-32
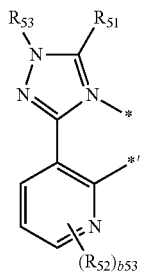
5-33
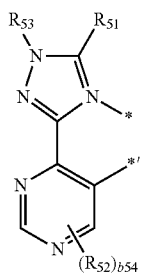
5-34
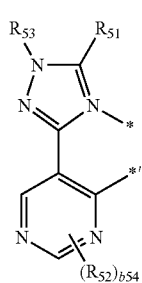
5-35
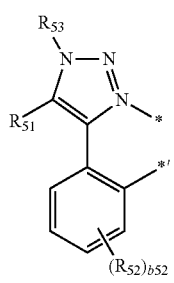
5-36
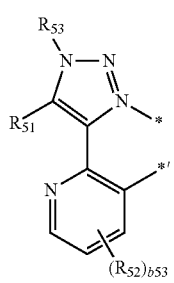
5-37
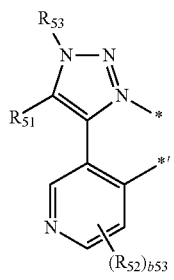
5-38
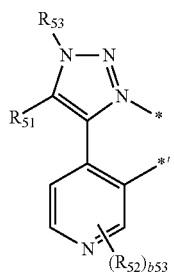
5-39

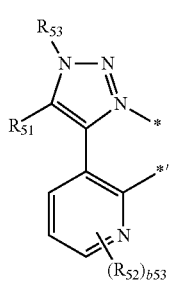
5-40
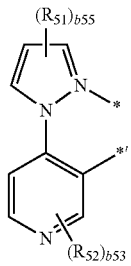
5-46
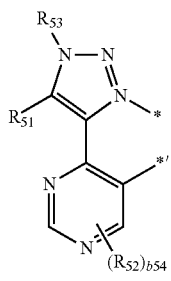
5-41
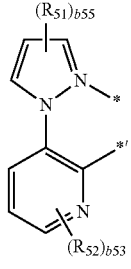
5-47
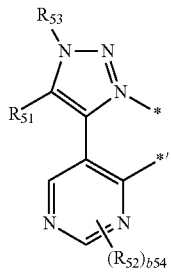
5-42
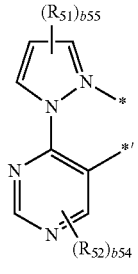
5-48
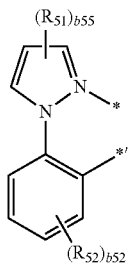
5-43
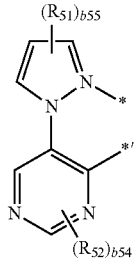
5-49
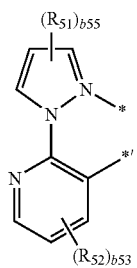
5-44
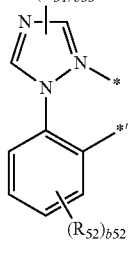
5-50
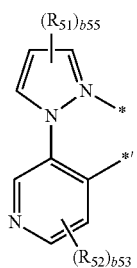
5-45
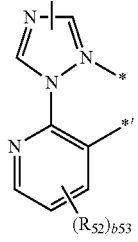
5-51

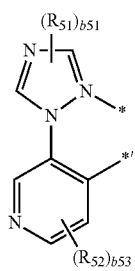
5-52
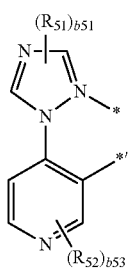
5-53
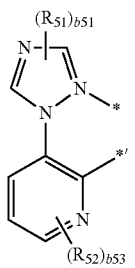
5-54
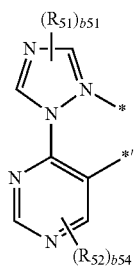
5-55
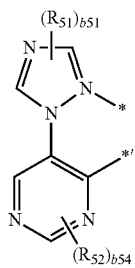
5-56
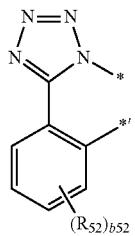
5-57
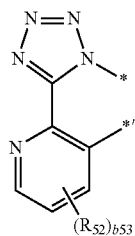
5-58
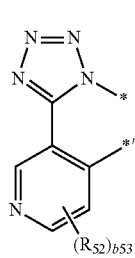
5-59
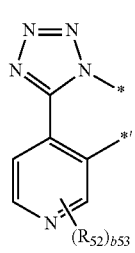
5-60
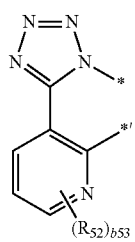
5-61
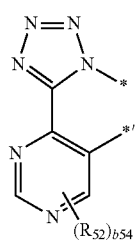
5-62
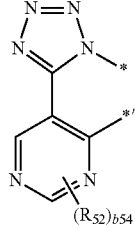
5-63

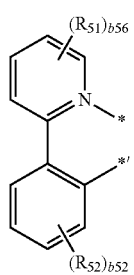
5-64
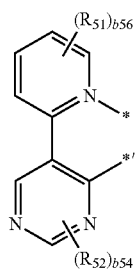
5-70
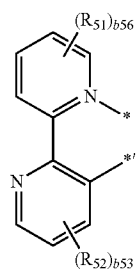
5-65
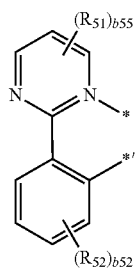
5-71
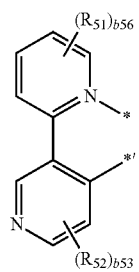
5-66
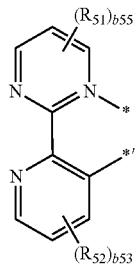
5-72
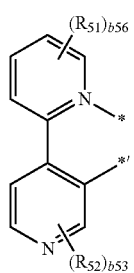
5-67
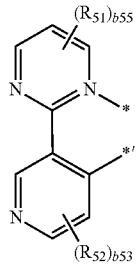
5-73
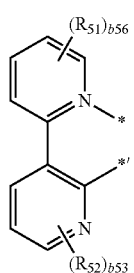
5-68
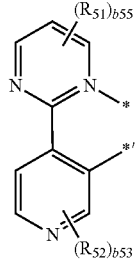
5-74
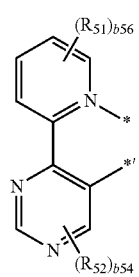
5-69
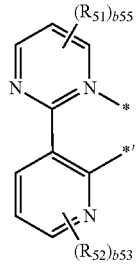
5-75

5-76 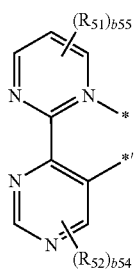
5-77 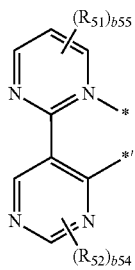
5-78 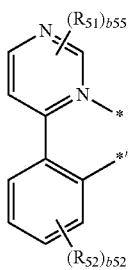
5-79 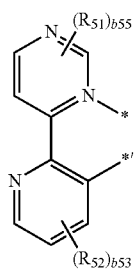
5-80 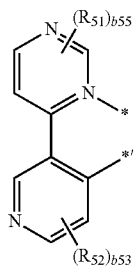
5-81 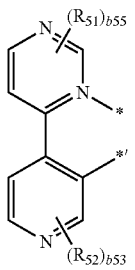
5-82 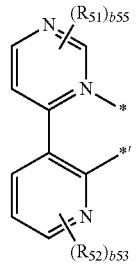
5-83 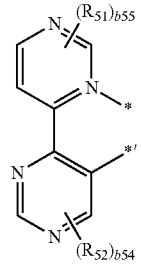
5-84 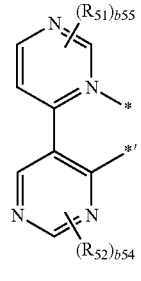
5-85 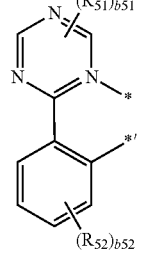
5-86 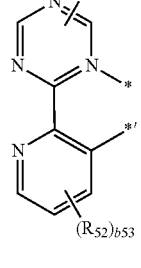
5-87 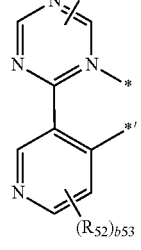

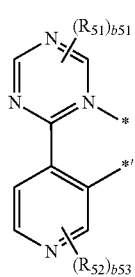
5-88
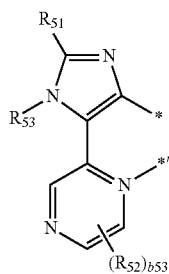
5-94
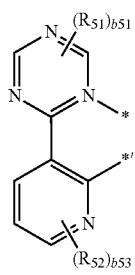
5-89
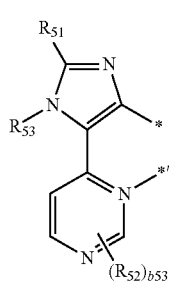
5-95
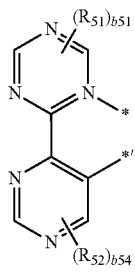
5-90
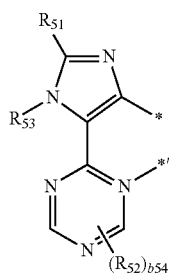
5-96
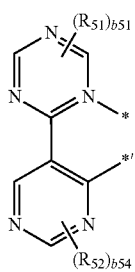
5-91
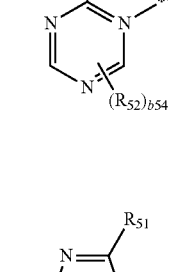
5-92
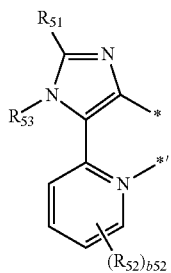
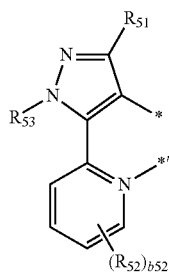
5-97
5-93
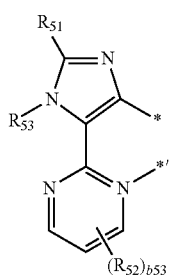
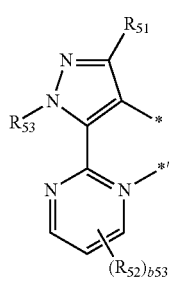
5-98

| | |
|---|---|
| 5-99 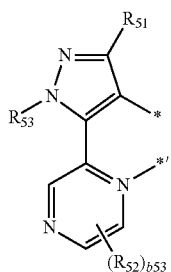 | 5-104 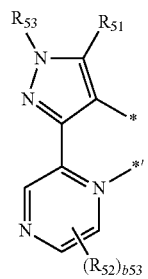 |
| 5-100 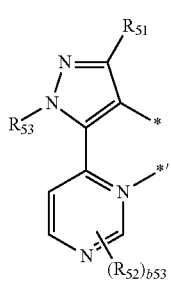 | 5-105 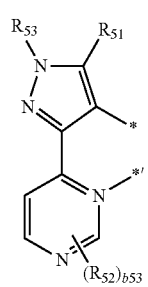 |
| 5-101 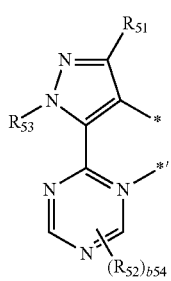 | 5-106 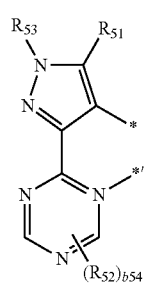 |
| 5-102 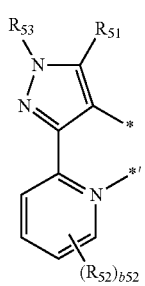 | 5-107 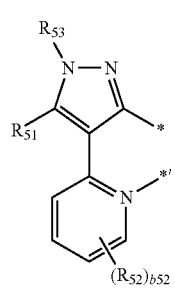 |
| 5-103 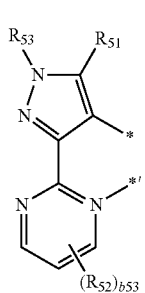 | 5-108 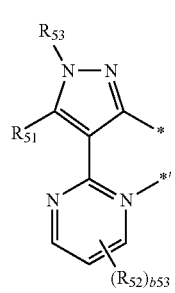 |

5-109 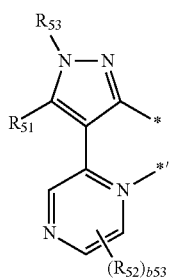

5-110 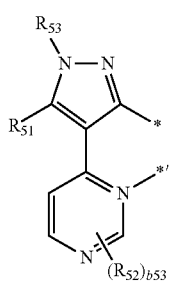

5-111 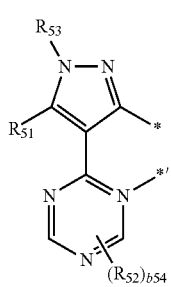

5-112 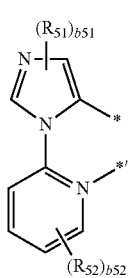

5-113 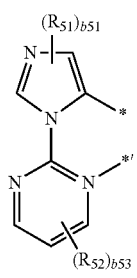

5-114 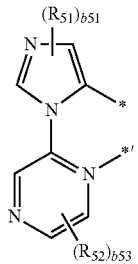

5-115 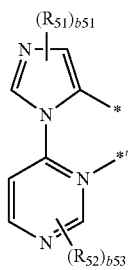

5-116 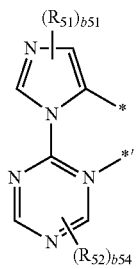

5-117 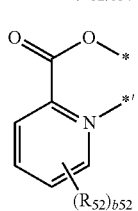

5-118 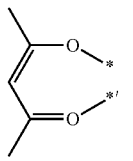

5-119 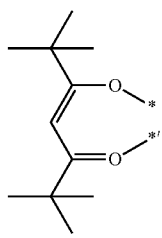

In Formulae 5-1 to 5-122, $R_{51}$ to $R_{57}$ may be each independently selected from a hydrogen, —F, a cyano group, a nitro group, a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group; a tert-hexyl group, an n-heptyl group, an iso-heptyl group, a sec-heptyl group, a tert-heptyl group, an n-octyl group, an iso-octyl group, a sec-octyl group; a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group; a naphthyl group, a pyridinyl group, a pyrimidinyl group, a triazinyl group, a dibenzofuranyl group, and a dibenzothiophenyl group, each substituted with at least one selected from —F, a cyano group, a nitro group, and a methyl group;

b51 and b54 may be each independently selected from 1 and 2;

b53 and b55 may be each independently an integer selected from 1 to 3;

b52 may be an integer selected from 1 to 4; and

* and *' may be each independently a binding site to $M_{11}$ in Formula 1.

In some embodiments, in Formula 1, $L_{11}$ may be selected from ligands represented by Formulae AN1 to AN5. However, embodiments are not limited thereto;

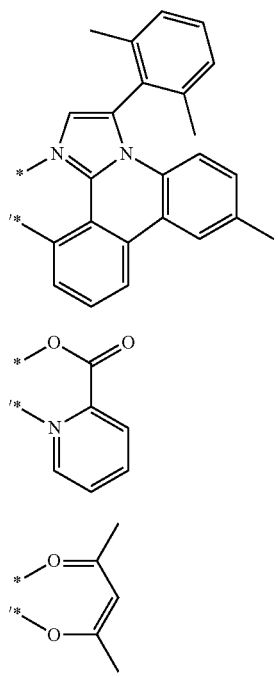

AN1

AN2

AN3

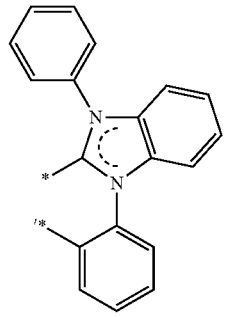

AN4

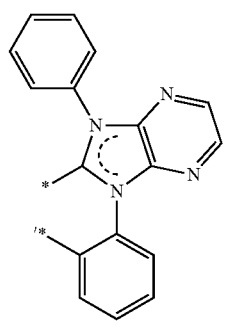

AN5

In Formulae AN1 to AN5, * and *' may be each independently a binding site to $M_{11}$ in Formula 1.

In Formula 1, m11 indicates the number of groups $L_{11}$, and m11 may be selected from 0, 1, 2, 3, and 4. When m11 is 2 or more, a plurality of groups $L_{11}$ may be identical to or different from each other. In some embodiments, in Formula 1, m11 may be selected from 0 and 1. However, embodiments are not limited thereto.

In Formula 1, n11 and m11 may be properly controlled based on the coordination number of Ir. For example, when n11 is 3, m11 may be 0. In some embodiments, when $L_{11}$ is a bidentate ligand with n11 being 2, m11 may be 1. In some embodiments, when $L_{11}$ is a bidentate ligand with n11 being 1, m11 may be 2.

In some embodiments, the moiety represented by

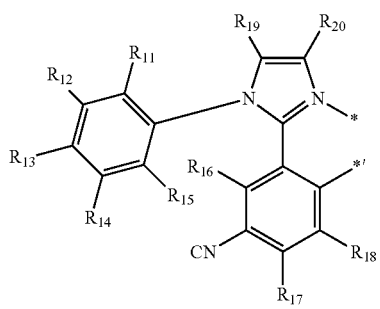

may be represented by one of Formulae 1-1 to 1-3. However, embodiments are not limited thereto:

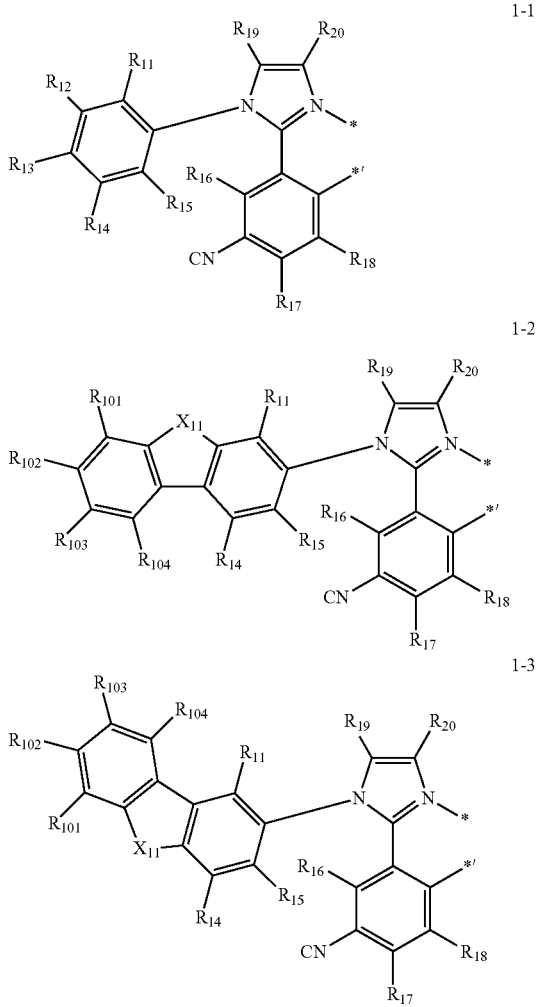

In Formulae 1-1 to 1-3, $X_{11}$ may be selected from O, S, and $N(R_{105})$;

$R_{11}$ to $R_{18}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{101}$ to $R_{105}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group;

at least one of $R_{11}$ to $R_{15}$ may be selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_5$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{19}$ and $R_{20}$ may be each independently selected from a hydrogen, a deuterium, $C_1$-$C_{30}$ alkyl group, and a deuterium substituted $C_1$-$C_{30}$ alkyl group; and at least one of $R_{11}$ to $R_{20}$ may be a deuterium-containing substituent.

For example, substituents in Formula 1-1 may be defined as in Table 1. However, embodiments are not limited thereto.

TABLE 1

| | | | | Formula 1-1 | | | | | | |
|---|---|---|---|---|---|---|---|---|---|---|
| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
| LM1 | X1 | H | X3 | H | X1 | H | H | H | H | D |
| LM2 | X1 | H | X3 | H | X1 | H | H | H | D | H |
| LM3 | X1 | H | X3 | H | X1 | H | H | H | D | D |
| LM4 | Y1 | H | X3 | H | Y1 | H | H | H | D | D |

TABLE 1-continued

Formula 1-1

| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM5 | Y2 | H | X3 | H | Y2 | H | H | H | D | D |
| LM6 | Y3 | H | X3 | H | Y3 | H | H | H | D | D |
| LM7 | Y3 | D | X3 | D | Y3 | H | H | H | D | D |
| LM8 | Y3 | D | X3 | D | Y3 | D | H | H | D | D |
| LM9 | Y3 | D | X3 | D | Y3 | D | D | H | D | D |
| LM10 | Y3 | D | X3 | D | Y3 | D | D | D | D | D |
| LM11 | Y3 | D | Y11 | D | Y3 | D | D | D | D | D |
| LM12 | Y3 | D | Y11 | D | Y3 | H | X1 | H | D | D |
| LM13 | Y3 | D | Y11 | D | Y3 | D | Y3 | D | D | D |
| LM14 | Y3 | D | Y11 | D | Y3 | H | X4 | H | D | D |
| LM15 | Y3 | D | Y11 | D | Y3 | D | Y12 | D | D | D |
| LM16 | X2 | H | X3 | H | X2 | H | H | H | H | D |
| LM17 | X2 | H | X3 | H | X2 | H | H | H | D | H |
| LM18 | X2 | H | X3 | H | X2 | H | H | H | D | D |
| LM19 | Y4 | H | X3 | H | Y4 | H | H | H | D | D |
| LM20 | Y5 | H | X3 | H | Y5 | H | H | H | D | D |
| LM21 | Y6 | H | X3 | H | Y6 | H | H | H | D | D |
| LM22 | Y7 | H | X3 | H | Y7 | H | H | H | D | D |
| LM23 | Y8 | H | X3 | H | Y8 | H | H | H | D | D |
| LM24 | Y9 | H | X3 | H | Y9 | H | H | H | D | D |
| LM25 | Y10 | H | X3 | H | Y10 | H | H | H | D | D |
| LM26 | Y10 | D | X3 | D | Y10 | H | H | H | D | D |
| LM27 | Y10 | D | X3 | D | Y10 | D | H | H | D | D |
| LM28 | Y10 | D | X3 | D | Y10 | D | D | H | D | D |
| LM29 | Y10 | D | X3 | D | Y10 | D | D | D | D | D |
| LM30 | Y10 | D | Y11 | D | Y10 | D | D | D | D | D |
| LM31 | Y10 | D | Y11 | D | Y10 | H | X1 | H | D | D |
| LM32 | Y10 | D | Y11 | D | Y10 | D | Y3 | D | D | D |
| LM33 | Y10 | D | Y11 | D | Y10 | H | X4 | H | D | D |
| LM34 | Y10 | D | Y11 | D | Y10 | D | Y12 | D | D | D |
| LM35 | X1 | H | X4 | H | X1 | H | H | H | H | D |
| LM36 | X1 | H | X4 | H | X1 | H | H | H | D | H |
| LM37 | X1 | H | X4 | H | X1 | H | H | H | D | D |
| LM38 | Y1 | H | X4 | H | Y1 | H | H | H | D | D |
| LM39 | Y2 | H | X4 | H | Y2 | H | H | H | D | D |
| LM40 | Y3 | H | X4 | H | Y3 | H | H | H | D | D |
| LM41 | Y3 | D | X4 | D | Y3 | H | H | H | D | D |
| LM42 | Y3 | D | X4 | D | Y3 | D | H | H | D | D |
| LM43 | Y3 | D | X4 | D | Y3 | D | D | H | D | D |
| LM44 | Y3 | D | X4 | D | Y3 | D | D | D | D | D |
| LM45 | Y3 | D | Y12 | D | Y3 | D | D | D | D | D |
| LM46 | Y3 | D | Y12 | D | Y3 | H | X1 | H | D | D |
| LM47 | Y3 | D | Y12 | D | Y3 | D | Y3 | D | D | D |
| LM48 | Y3 | D | Y12 | D | Y3 | H | X4 | H | D | D |
| LM49 | Y3 | D | Y12 | D | Y3 | D | Y12 | D | D | D |
| LM50 | X2 | H | X4 | H | X2 | H | H | H | H | D |
| LM51 | X2 | H | X4 | H | X2 | H | H | H | D | H |
| LM52 | X2 | H | X4 | H | X2 | H | H | H | D | D |
| LM53 | Y4 | H | X4 | H | Y4 | H | H | H | D | D |
| LM54 | Y5 | H | X4 | H | Y5 | H | H | H | D | D |
| LM55 | Y6 | H | X4 | H | Y8 | H | H | H | D | D |
| LM56 | Y7 | H | X4 | H | Y7 | H | H | H | D | D |
| LM57 | Y8 | H | X4 | H | Y8 | H | H | H | D | D |
| LM58 | Y9 | H | X4 | H | Y9 | H | H | H | D | D |
| LM59 | Y10 | H | X4 | H | Y10 | H | H | H | D | D |
| LM60 | Y10 | D | X4 | D | Y10 | H | H | H | D | D |
| LM61 | Y10 | D | X4 | D | Y10 | D | H | H | D | D |
| LM62 | Y10 | D | X4 | D | Y10 | D | D | H | D | D |
| LM63 | Y10 | D | X4 | D | Y10 | D | D | D | D | D |
| LM64 | Y10 | D | Y12 | D | Y10 | D | D | D | D | D |
| LM65 | Y10 | D | Y12 | D | Y10 | H | X1 | H | D | D |
| LM66 | Y10 | D | Y12 | D | Y10 | D | Y3 | D | D | D |
| LM67 | Y10 | D | Y12 | D | Y10 | H | X4 | H | D | D |
| LM68 | Y10 | D | Y12 | D | Y10 | D | Y12 | D | D | D |
| LM69 | X1 | H | X5 | H | X1 | H | H | H | H | D |
| LM70 | X1 | H | X5 | H | X1 | H | H | H | D | H |
| LM71 | X1 | H | X5 | H | X1 | H | H | H | D | D |
| LM72 | Y1 | H | X5 | H | Y1 | H | H | H | D | D |
| LM73 | Y2 | H | X5 | H | Y2 | H | H | H | D | D |
| LM74 | Y3 | H | X5 | H | Y3 | H | H | H | D | D |
| LM75 | Y3 | D | X5 | D | Y3 | H | H | H | D | D |
| LM76 | Y3 | D | X5 | D | Y3 | D | H | H | D | D |
| LM77 | Y3 | D | X5 | D | Y3 | D | D | H | D | D |
| LM78 | Y3 | D | X5 | D | Y3 | D | D | D | D | D |
| LM79 | Y3 | D | Y13 | D | Y3 | D | D | D | D | D |

TABLE 1-continued

Formula 1-1

| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM80 | Y3 | D | Y13 | D | Y3 | H | X1 | H | D | D |
| LM81 | Y3 | D | Y13 | D | Y3 | D | Y3 | D | D | D |
| LM82 | Y3 | D | Y13 | D | Y3 | H | X4 | H | D | D |
| LM83 | Y3 | D | Y13 | D | Y3 | D | Y12 | D | D | D |
| LM84 | X2 | H | X5 | H | X2 | H | H | H | H | D |
| LM85 | X2 | H | X5 | H | X2 | H | H | H | D | H |
| LM86 | X2 | H | X5 | H | X2 | H | H | H | D | D |
| LM87 | Y4 | H | X5 | H | Y4 | H | H | H | D | D |
| LM88 | Y5 | H | X5 | H | Y5 | H | H | H | D | D |
| LM89 | Y6 | H | X5 | H | Y6 | H | H | H | D | D |
| LM90 | Y7 | H | X5 | H | Y7 | H | H | H | D | D |
| LM91 | Y8 | H | X5 | H | Y8 | H | H | H | D | D |
| LM92 | Y9 | H | X5 | H | Y9 | H | H | H | D | D |
| LM93 | Y10 | H | X5 | H | Y10 | H | H | H | D | D |
| LM94 | Y10 | D | X5 | D | Y10 | H | H | H | D | D |
| LM95 | Y10 | D | X5 | D | Y10 | D | H | H | D | D |
| LM96 | Y10 | D | X5 | D | Y10 | D | D | H | D | D |
| LM97 | Y10 | D | X5 | D | Y10 | D | D | D | D | D |
| LM98 | Y10 | D | Y13 | D | Y10 | D | D | D | D | D |
| LM99 | Y10 | D | Y13 | D | Y10 | H | X1 | H | D | D |
| LM100 | Y10 | D | Y13 | D | Y10 | D | Y3 | D | D | D |
| LM101 | Y10 | D | Y13 | D | Y10 | H | X4 | H | D | D |
| LM102 | Y10 | D | Y13 | D | Y10 | D | Y12 | D | D | D |
| LM103 | X1 | H | X6 | H | X1 | H | H | H | H | D |
| LM104 | X1 | H | X6 | H | X1 | H | H | H | D | H |
| LM105 | X1 | H | X6 | H | X1 | H | H | H | D | D |
| LM106 | Y1 | H | X6 | H | Y1 | H | H | H | D | D |
| LM107 | Y2 | H | X6 | H | Y2 | H | H | H | D | D |
| LM108 | Y3 | H | X6 | H | Y3 | H | H | H | D | D |
| LM109 | Y3 | D | X6 | D | Y3 | H | H | H | D | D |
| LM110 | Y3 | D | X6 | D | Y3 | D | H | H | D | D |
| LM111 | Y3 | D | X6 | D | Y3 | D | D | H | D | D |
| LM112 | Y3 | D | X6 | D | Y3 | D | D | D | D | D |
| LM113 | Y3 | D | Y14 | D | Y3 | D | D | D | D | D |
| LM114 | Y3 | D | Y14 | D | Y3 | H | X1 | H | D | D |
| LM115 | Y3 | D | Y14 | D | Y3 | D | Y3 | D | D | D |
| LM116 | Y3 | D | Y14 | D | Y3 | H | X4 | H | D | D |
| LM117 | Y3 | D | Y14 | D | Y3 | D | Y12 | D | D | D |
| LM118 | X2 | H | X6 | H | X2 | H | H | H | H | D |
| LM119 | X2 | H | X6 | H | X2 | H | H | H | D | H |
| LM120 | X2 | H | X6 | H | X2 | H | H | H | D | D |
| LM121 | Y4 | H | X6 | H | Y4 | H | H | H | D | D |
| LM122 | Y5 | H | X6 | H | Y5 | H | H | H | D | D |
| LM123 | Y6 | H | X6 | H | Y6 | H | H | H | D | D |
| LM124 | Y7 | H | X6 | H | Y7 | H | H | H | D | D |
| LM125 | Y8 | H | X6 | H | Y8 | H | H | H | D | D |
| LM126 | Y9 | H | X6 | H | Y9 | H | H | H | D | D |
| LM127 | Y10 | H | X6 | H | Y10 | H | H | H | D | D |
| LM128 | Y10 | D | X6 | D | Y10 | H | H | H | D | D |
| LM129 | Y10 | D | X6 | D | Y10 | D | H | H | D | D |
| LM130 | Y10 | D | X6 | D | Y10 | D | D | H | D | D |
| LM131 | Y10 | D | X6 | D | Y10 | D | D | D | D | D |
| LM132 | Y10 | D | Y14 | D | Y10 | D | D | D | D | D |
| LM133 | Y10 | D | Y14 | D | Y10 | H | X1 | H | D | D |
| LM134 | Y10 | D | Y14 | D | Y10 | D | Y3 | D | D | D |
| LM135 | Y10 | D | Y14 | D | Y10 | H | X4 | H | D | D |
| LM136 | Y10 | D | Y14 | D | Y10 | D | Y12 | D | D | D |
| LM137 | X1 | H | X7 | H | X1 | H | H | H | H | D |
| LM138 | X1 | H | X7 | H | X1 | H | H | H | D | H |
| LM139 | X1 | H | X7 | H | X1 | H | H | H | D | D |
| LM140 | Y1 | H | X7 | H | Y1 | H | H | H | D | D |
| LM141 | Y2 | H | X7 | H | Y2 | H | H | H | D | D |
| LM142 | Y3 | H | X7 | H | Y3 | H | H | H | D | D |
| LM143 | Y3 | D | X7 | D | Y3 | H | H | H | D | D |
| LM144 | Y3 | D | X7 | D | Y3 | D | H | H | D | D |
| LM145 | Y3 | D | X7 | D | Y3 | D | D | H | D | D |
| LM146 | Y3 | D | X7 | D | Y3 | D | D | D | D | D |
| LM147 | Y3 | D | X8 | D | Y3 | D | D | D | D | D |
| LM148 | Y3 | D | Y16 | D | Y3 | D | D | D | D | D |
| LM149 | Y3 | D | Y17 | D | Y3 | D | D | D | D | D |
| LM150 | Y3 | D | Y18 | D | Y3 | D | D | D | D | D |
| LM151 | Y3 | D | Y15 | D | Y3 | D | D | D | D | D |
| LM152 | Y3 | D | Y15 | D | Y3 | H | X1 | H | D | D |
| LM153 | Y3 | D | Y15 | D | Y3 | D | Y3 | D | D | D |
| LM154 | Y3 | D | Y16 | D | Y3 | D | Y3 | D | D | D |

TABLE 1-continued

Formula 1-1

| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM155 | Y3 | D | Y17 | D | Y3 | D | Y3 | D | D | D |
| LM156 | Y3 | D | Y18 | D | Y3 | D | Y3 | D | D | D |
| LM157 | Y3 | D | Y15 | D | Y3 | H | X4 | H | D | D |
| LM158 | Y3 | D | Y15 | D | Y3 | D | Y12 | D | D | D |
| LM159 | Y3 | D | Y16 | D | Y3 | D | Y12 | D | D | D |
| LM160 | Y3 | D | Y17 | D | Y3 | D | Y12 | D | D | D |
| LM161 | Y3 | D | Y18 | D | Y3 | D | Y12 | D | D | D |
| LM162 | X2 | H | X7 | H | X2 | H | H | H | H | D |
| LM163 | X2 | H | X7 | H | X2 | H | H | H | D | H |
| LM164 | X2 | H | X7 | H | X2 | H | H | H | D | D |
| LM165 | Y4 | H | X7 | H | Y4 | H | H | H | D | D |
| LM166 | Y5 | H | X7 | H | Y5 | H | H | H | D | D |
| LM167 | Y6 | H | X7 | H | Y6 | H | H | H | D | D |
| LM168 | Y7 | H | X7 | H | Y7 | H | H | H | D | D |
| LM169 | Y8 | H | X7 | H | Y8 | H | H | H | D | D |
| LM170 | Y9 | H | X7 | H | Y9 | H | H | H | D | D |
| LM171 | Y10 | H | X7 | H | Y10 | H | H | H | D | D |
| LM172 | Y10 | D | X7 | D | Y10 | H | H | H | D | D |
| LM173 | Y10 | D | X7 | D | Y10 | D | H | H | D | D |
| LM174 | Y10 | D | X7 | D | Y10 | D | D | H | D | D |
| LM175 | Y10 | D | X7 | D | Y10 | D | D | D | D | D |
| LM176 | Y10 | D | X8 | D | Y10 | D | D | D | D | D |
| LM177 | Y10 | D | Y16 | D | Y10 | D | D | D | D | D |
| LM178 | Y10 | D | Y17 | D | Y10 | D | D | D | D | D |
| LM179 | Y10 | D | Y18 | D | Y10 | D | D | D | D | D |
| LM180 | Y10 | D | Y15 | D | Y10 | D | D | D | D | D |
| LM181 | Y10 | D | Y15 | D | Y10 | H | X1 | H | D | D |
| LM182 | Y10 | D | Y15 | D | Y10 | D | Y3 | D | D | D |
| LM183 | Y10 | D | Y16 | D | Y10 | D | Y3 | D | D | D |
| LM184 | Y10 | D | Y17 | D | Y10 | D | Y3 | D | D | D |
| LM185 | Y10 | D | Y18 | D | Y10 | D | Y3 | D | D | D |
| LM186 | Y10 | D | Y15 | D | Y10 | H | X4 | H | D | D |
| LM187 | Y10 | D | Y15 | D | Y10 | D | Y12 | D | D | D |
| LM188 | Y10 | D | Y16 | D | Y10 | D | Y12 | D | D | D |
| LM189 | Y10 | D | Y17 | D | Y10 | D | Y12 | D | D | D |
| LM190 | Y10 | D | Y18 | D | Y10 | D | Y12 | D | D | D |
| LM191 | X1 | X7 | H | H | X1 | H | H | H | H | D |
| LM192 | X1 | X7 | H | H | X1 | H | H | H | D | H |
| LM193 | X1 | X7 | H | H | X1 | H | H | H | D | D |
| LM194 | Y1 | X7 | H | H | Y1 | H | H | H | D | D |
| LM195 | Y2 | X7 | H | H | Y2 | H | H | H | D | D |
| LM196 | Y3 | X7 | H | H | Y3 | H | H | H | D | D |
| LM197 | Y3 | X7 | D | D | Y3 | H | H | H | D | D |
| LM198 | Y3 | X7 | D | D | Y3 | D | H | H | D | D |
| LM199 | Y3 | X7 | D | D | Y3 | D | D | H | D | D |
| LM200 | Y3 | X7 | D | D | Y3 | D | D | D | D | D |
| LM201 | Y3 | Y15 | D | D | Y3 | D | D | D | D | D |
| LM202 | Y3 | Y16 | D | D | Y3 | D | D | D | D | D |
| LM203 | Y3 | Y17 | D | D | Y3 | D | D | D | D | D |
| LM204 | Y3 | Y18 | D | D | Y3 | D | D | D | D | D |
| LM205 | Y3 | Y15 | D | D | Y3 | H | X1 | H | D | D |
| LM206 | Y3 | Y15 | D | D | Y3 | D | Y3 | D | D | D |
| LM207 | Y3 | Y16 | D | D | Y3 | D | Y3 | D | D | D |
| LM208 | Y3 | Y17 | D | D | Y3 | D | Y3 | D | D | D |
| LM209 | Y3 | Y18 | D | D | Y3 | D | Y3 | D | D | D |
| LM210 | Y3 | Y15 | D | D | Y3 | H | X4 | H | D | D |
| LM211 | Y3 | Y15 | D | D | Y3 | D | Y12 | D | D | D |
| LM212 | Y3 | Y16 | D | D | Y3 | D | Y12 | D | D | D |
| LM213 | Y3 | Y17 | D | D | Y3 | D | Y12 | D | D | D |
| LM214 | Y3 | Y18 | D | D | Y3 | D | Y12 | D | D | D |
| LM215 | X2 | X7 | H | H | X2 | H | H | H | H | D |
| LM216 | X2 | X7 | H | H | X2 | H | H | H | D | H |
| LM217 | X2 | X7 | H | H | X2 | H | H | H | D | D |
| LM218 | Y4 | X7 | H | H | Y4 | H | H | H | D | D |
| LM219 | Y5 | X7 | H | H | Y5 | H | H | H | D | D |
| LM220 | Y6 | X7 | H | H | Y6 | H | H | H | D | D |
| LM221 | Y7 | X7 | H | H | Y7 | H | H | H | D | D |
| LM222 | Y8 | X7 | H | H | Y8 | H | H | H | D | D |
| LM223 | Y9 | X7 | H | H | Y9 | H | H | H | D | D |
| LM224 | Y10 | X7 | H | H | Y10 | H | H | H | D | D |
| LM225 | Y10 | X7 | D | D | Y10 | H | H | H | D | D |
| LM226 | Y10 | X7 | D | D | Y10 | D | H | H | D | D |
| LM227 | Y10 | X7 | D | D | Y10 | D | D | H | D | D |
| LM228 | Y10 | X7 | D | D | Y10 | D | D | D | D | D |
| LM229 | Y10 | X8 | D | D | Y10 | D | D | D | D | D |

TABLE 1-continued

Formula 1-1

| Ligand name | $R_{11}$ | $R_{12}$ | $R_{13}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|
| LM230 | Y10 | Y16 | D | D | Y10 | D | D | D | D | D |
| LM231 | Y10 | Y17 | D | D | Y10 | D | D | D | D | D |
| LM232 | Y10 | Y18 | D | D | Y10 | D | D | D | D | D |
| LM233 | Y10 | Y15 | D | D | Y10 | D | D | D | D | D |
| LM234 | Y10 | Y15 | D | D | Y10 | H | X1 | H | D | D |
| LM235 | Y10 | Y15 | D | D | Y10 | D | Y3 | D | D | D |
| LM236 | Y10 | Y16 | D | D | Y10 | D | Y3 | D | D | D |
| LM237 | Y10 | Y17 | D | D | Y10 | D | Y3 | D | D | D |
| LM238 | Y10 | Y18 | D | D | Y10 | D | Y3 | D | D | D |
| LM239 | Y10 | Y15 | D | D | Y10 | H | X4 | H | D | D |
| LM240 | Y10 | Y15 | D | D | Y10 | D | Y12 | D | D | D |
| LM241 | Y10 | Y16 | D | D | Y10 | D | Y12 | D | D | D |
| LM242 | Y10 | Y17 | D | D | Y10 | D | Y12 | D | D | D |
| LM243 | Y10 | Y18 | D | D | Y10 | D | Y12 | D | D | D |

In Table 1, X1 to 10 and Y1 to Y18 may be represented by the following formulae.

-continued
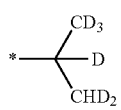
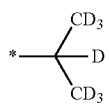
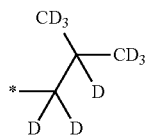
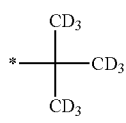
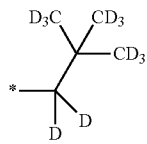
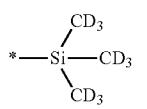
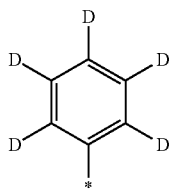
Y9
Y10 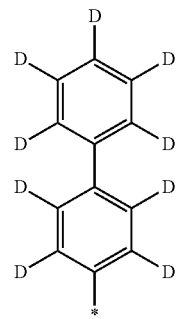
Y11
Y12
Y13 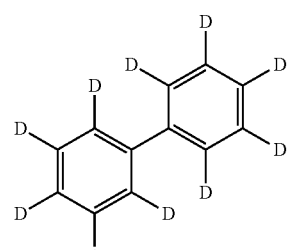
Y14
Y15 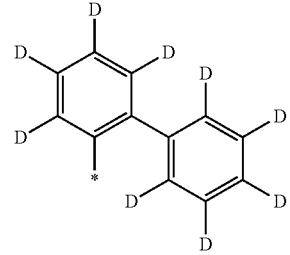
Y16
Y17
Y18
For example, substituents in Formula 1-2 may be defined as in Table 2. However, embodiments are not limited thereto.
TABLE 2
| | Formula 1-2 | | | | | | | | | | | | |
|---|---|---|---|---|---|---|---|---|---|---|---|---|---|
| Ligand name | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
| LFM1 | Y10 | N—Ph | D | D | D | D | D | Y10 | D | D | D | D | D |
| LFM2 | Y10 | S | D | D | D | D | D | Y10 | D | D | D | D | D |
| LFM3 | Y10 | O | D | D | D | D | D | Y10 | D | D | D | D | D |
| LFM4 | Y3 | O | D | D | D | D | D | Y3 | D | D | D | D | D |
| LFM5 | Y10 | O | D | D | D | D | D | Y10 | D | D | D | D | D |
| LFM6 | Y10 | O | D | D | D | D | D | Y10 | D | Y3 | D | D | D |
| LFM7 | Y10 | O | D | D | D | D | D | Y10 | D | Y12 | D | D | D |

In Table 2, "Ph" indicates a phenyl group, and X1 to X10 and Y1 to Y18 may be the same as those represented above in connection with Table 1.

For example, substituents in Formula 1-3 may be defined as in Table 3. However, embodiments are not limited thereto.

TABLE 3

Formula 1-3

| Ligand name | $R_{11}$ | $X_{11}$ | $R_{101}$ | $R_{102}$ | $R_{103}$ | $R_{104}$ | $R_{14}$ | $R_{15}$ | $R_{16}$ | $R_{17}$ | $R_{18}$ | $R_{19}$ | $R_{20}$ |
|---|---|---|---|---|---|---|---|---|---|---|---|---|---|
| LFP1 | Y10 | N—Ph | D | D | D | D | D | Y10 | D | D | D | D | D |
| LFP2 | Y10 | S | D | D | D | D | D | Y10 | D | D | D | D | D |
| LFP3 | Y10 | O | D | D | D | D | D | Y10 | D | D | D | D | D |
| LFP4 | Y3 | O | D | D | D | D | D | Y3 | D | D | D | D | D |
| LFP5 | Y10 | O | D | D | D | D | D | Y10 | D | D | D | D | D |
| LFP6 | Y10 | O | D | D | D | D | D | Y10 | D | Y3 | D | D | D |
| LFP7 | Y10 | O | D | D | D | D | D | Y10 | D | Y12 | D | D | D |

In Table 3, "Ph" indicates a phenyl group, and X1 to X10 and Y1 to Y18 may be the same as those represented above in connection with Table 1.

In some other embodiments, the organometallic compound of Formula 1 may be represented by one of Formulae 1-11 to 1-22. However, embodiments are not limited thereto.

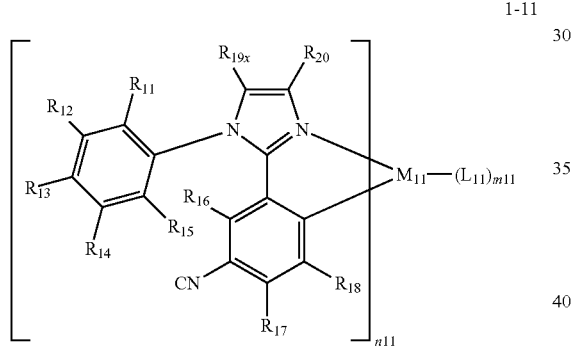

1-11

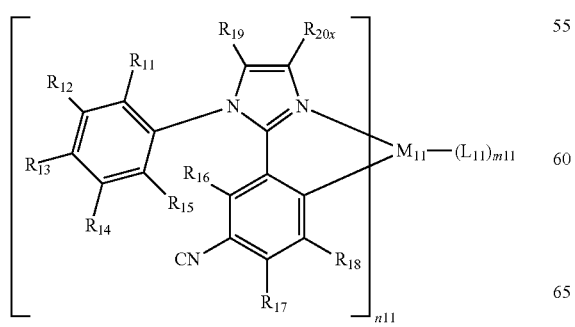

1-12

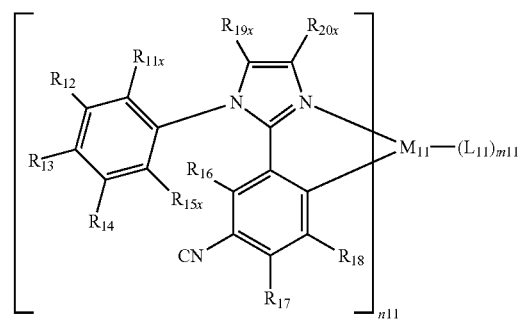

1-13

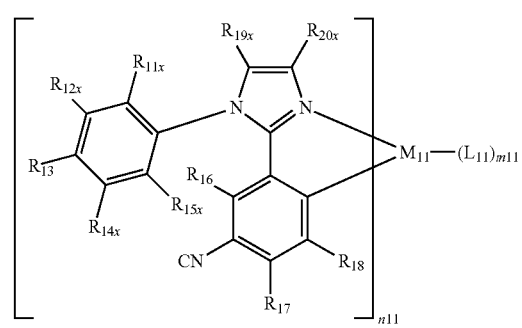

1-14

1-15

1-16
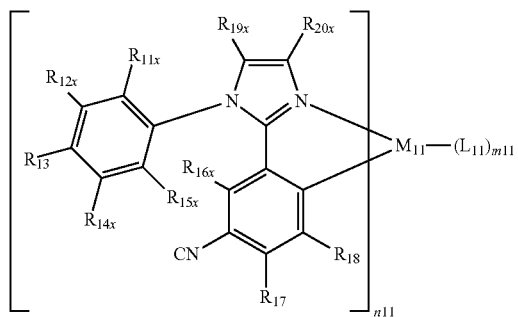

1-17
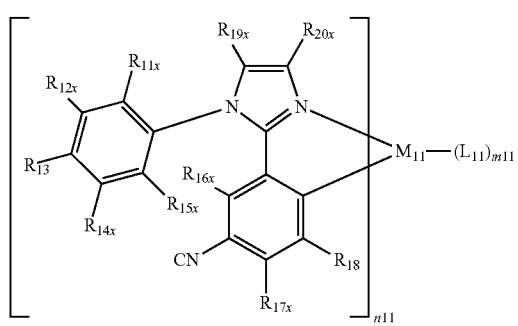

1-18
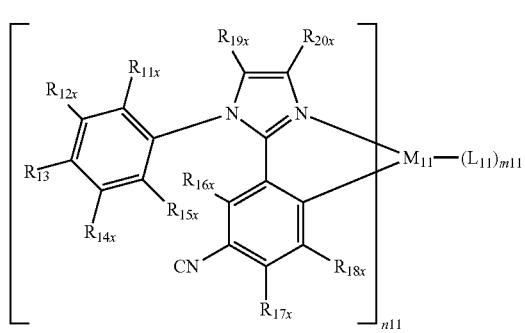

1-19
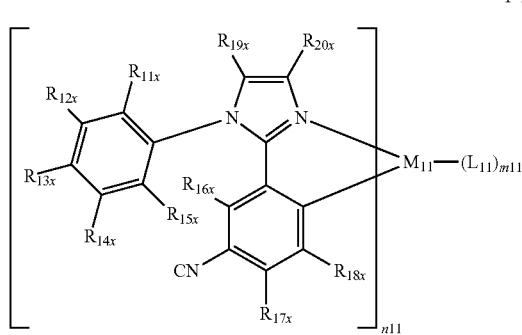

1-20
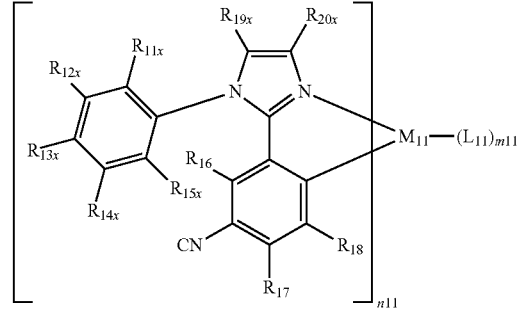

1-21
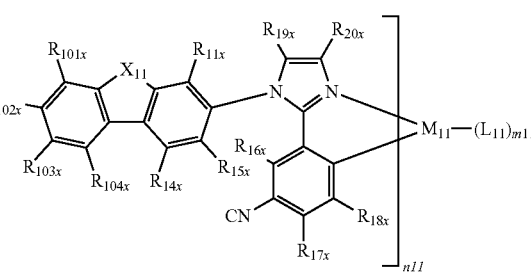

1-22
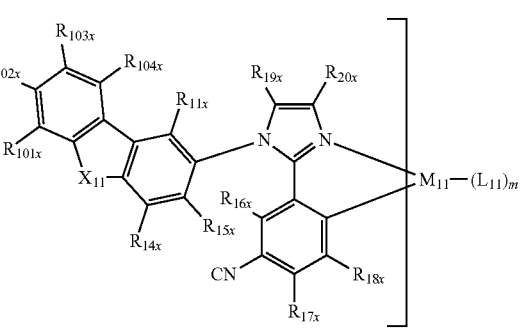

In Formulae 1-11 to 1-22, $M_{11}$, $R_{11}$ to $R_{20}$, n11, $L_{11}$, and m11 may be defined the same as those of Formula 1;

$X_{11}$ may be selected from O, S, and $N(R_{105})$;

$R_{101}$ to $R_{105}$ may be each independently selected from a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group; and $R_{11x}$, $R_{12x}$, $R_{13x}$, $R_{14x}$, $R_{15x}$, $R_{16x}$, $R_{17x}$, $R_{18x}$, $R_{19x}$, $R_{20x}$, $R_{101x}$, $R_{102x}$, $R_{103x}$, and $R_{104x}$ may be each independently a deuterium-containing substituent.

In some embodiments, the organometallic compound of Formula 1 may be represented by Formula 101. However, embodiments are not limited thereto.

$(L_{101})_{n101}\text{-}M_{101}\text{-}(L_{102})_{m101}$   Formula 101

In Formula 101, $L_{101}$, n101, $M_{101}$, $L_{102}$, and m101 may be defined as shown in Tables 4 to 6.

TABLE 4

| Compound name | $L_{101}$ | n101 | $M_{101}$ | $L_{102}$ | m101 |
|---|---|---|---|---|---|
| BD001 | LM1 | 3 | Ir | — | 0 |
| BD002 | LM2 | 3 | Ir | — | 0 |
| BD003 | LM3 | 3 | Ir | — | 0 |
| BD004 | LM4 | 3 | Ir | — | 0 |
| BD005 | LM5 | 3 | Ir | — | 0 |
| BD006 | LM6 | 3 | Ir | — | 0 |
| BD007 | LM7 | 3 | Ir | — | 0 |
| BD008 | LM8 | 3 | Ir | — | 0 |
| BD009 | LM9 | 3 | Ir | — | 0 |
| BD010 | LM10 | 3 | Ir | — | 0 |
| BD011 | LM11 | 3 | Ir | — | 0 |
| BD012 | LM12 | 3 | Ir | — | 0 |
| BD013 | LM13 | 3 | Ir | — | 0 |
| BD014 | LM14 | 3 | Ir | — | 0 |
| BD015 | LM15 | 3 | Ir | — | 0 |
| BD016 | LM16 | 3 | Ir | — | 0 |
| BD017 | LM17 | 3 | Ir | — | 0 |
| BD018 | LM18 | 3 | Ir | — | 0 |
| BD019 | LM19 | 3 | Ir | — | 0 |
| BD020 | LM20 | 3 | Ir | — | 0 |
| BD021 | LM21 | 3 | Ir | — | 0 |
| BD022 | LM22 | 3 | Ir | — | 0 |
| BD023 | LM23 | 3 | Ir | — | 0 |
| BD024 | LM24 | 3 | Ir | — | 0 |
| BD025 | LM25 | 3 | Ir | — | 0 |
| BD026 | LM26 | 3 | Ir | — | 0 |
| BD027 | LM27 | 3 | Ir | — | 0 |
| BD028 | LM28 | 3 | Ir | — | 0 |
| BD029 | LM29 | 3 | Ir | — | 0 |
| BD030 | LM30 | 3 | Ir | — | 0 |
| BD031 | LM31 | 3 | Ir | — | 0 |
| BD032 | LM32 | 3 | Ir | — | 0 |
| BD033 | LM33 | 3 | Ir | — | 0 |
| BD034 | LM34 | 3 | Ir | — | 0 |
| BD035 | LM35 | 3 | Ir | — | 0 |
| BD036 | LM36 | 3 | Ir | — | 0 |
| BD037 | LM37 | 3 | Ir | — | 0 |
| BD038 | LM38 | 3 | Ir | — | 0 |
| BD039 | LM39 | 3 | Ir | — | 0 |
| BD040 | LM40 | 3 | Ir | — | 0 |
| BD041 | LM41 | 3 | Ir | — | 0 |
| BD042 | LM42 | 3 | Ir | — | 0 |
| BD043 | LM43 | 3 | Ir | — | 0 |
| BD044 | LM44 | 3 | Ir | — | 0 |
| BD045 | LM45 | 3 | Ir | — | 0 |
| BD046 | LM46 | 3 | Ir | — | 0 |
| BD047 | LM47 | 3 | Ir | — | 0 |
| BD048 | LM48 | 3 | Ir | — | 0 |
| BD049 | LM49 | 3 | Ir | — | 0 |
| BD050 | LM50 | 3 | Ir | — | 0 |
| BD051 | LM51 | 3 | Ir | — | 0 |
| BD052 | LM52 | 3 | Ir | — | 0 |
| BD053 | LM53 | 3 | Ir | — | 0 |
| BD054 | LM54 | 3 | Ir | — | 0 |
| BD055 | LM55 | 3 | Ir | — | 0 |
| BD056 | LM56 | 3 | Ir | — | 0 |
| BD057 | LM57 | 3 | Ir | — | 0 |
| BD058 | LM58 | 3 | Ir | — | 0 |
| BD059 | LM59 | 3 | Ir | — | 0 |
| BD060 | LM60 | 3 | Ir | — | 0 |
| BD061 | LM61 | 3 | Ir | — | 0 |
| BD062 | LM62 | 3 | Ir | — | 0 |
| BD063 | LM63 | 3 | Ir | — | 0 |
| BD064 | LM64 | 3 | Ir | — | 0 |
| BD065 | LM65 | 3 | Ir | — | 0 |
| BD066 | LM66 | 3 | Ir | — | 0 |
| BD067 | LM67 | 3 | Ir | — | 0 |
| BD068 | LM68 | 3 | Ir | — | 0 |
| BD069 | LM69 | 3 | Ir | — | 0 |
| BD070 | LM70 | 3 | Ir | — | 0 |
| BD071 | LM71 | 3 | Ir | — | 0 |
| BD072 | LM72 | 3 | Ir | — | 0 |
| BD073 | LM73 | 3 | Ir | — | 0 |
| BD074 | LM74 | 3 | Ir | — | 0 |
| BD075 | LM75 | 3 | Ir | — | 0 |
| BD076 | LM76 | 3 | Ir | — | 0 |
| BD077 | LM77 | 3 | Ir | — | 0 |
| BD078 | LM78 | 3 | Ir | — | 0 |
| BD079 | LM79 | 3 | Ir | — | 0 |
| BD080 | LM80 | 3 | Ir | — | 0 |
| BD081 | LM81 | 3 | Ir | — | 0 |
| BD082 | LM82 | 3 | Ir | — | 0 |
| BD083 | LM83 | 3 | Ir | — | 0 |
| BD084 | LM84 | 3 | Ir | — | 0 |
| BD085 | LM85 | 3 | Ir | — | 0 |
| BD086 | LM86 | 3 | Ir | — | 0 |
| BD087 | LM87 | 3 | Ir | — | 0 |
| BD088 | LM88 | 3 | Ir | — | 0 |
| BD089 | LM89 | 3 | Ir | — | 0 |
| BD090 | LM90 | 3 | Ir | — | 0 |
| BD091 | LM91 | 3 | Ir | — | 0 |
| BD092 | LM92 | 3 | Ir | — | 0 |
| BD093 | LM93 | 3 | Ir | — | 0 |
| BD094 | LM94 | 3 | Ir | — | 0 |
| BD095 | LM95 | 3 | Ir | — | 0 |
| BD096 | LM96 | 3 | Ir | — | 0 |
| BD097 | LM97 | 3 | Ir | — | 0 |
| BD098 | LM98 | 3 | Ir | — | 0 |
| BD099 | LM99 | 3 | Ir | — | 0 |
| BD100 | LM100 | 3 | Ir | — | 0 |

TABLE 5

| Compound name | $L_{101}$ | n101 | $M_{101}$ | $L_{102}$ | m101 |
|---|---|---|---|---|---|
| BD101 | LM101 | 3 | Ir | — | 0 |
| BD102 | LM102 | 3 | Ir | — | 0 |
| BD103 | LM103 | 3 | Ir | — | 0 |
| BD104 | LM104 | 3 | Ir | — | 0 |
| BD105 | LM105 | 3 | Ir | — | 0 |
| BD106 | LM106 | 3 | Ir | — | 0 |
| BD107 | LM107 | 3 | Ir | — | 0 |
| BD108 | LM108 | 3 | Ir | — | 0 |
| BD109 | LM109 | 3 | Ir | — | 0 |
| BD110 | LM110 | 3 | Ir | — | 0 |
| BD111 | LM111 | 3 | Ir | — | 0 |
| BD112 | LM112 | 3 | Ir | — | 0 |
| BD113 | LM113 | 3 | Ir | — | 0 |
| BD114 | LM114 | 3 | Ir | — | 0 |
| BD115 | LM115 | 3 | Ir | — | 0 |
| BD116 | LM116 | 3 | Ir | — | 0 |
| BD117 | LM117 | 3 | Ir | — | 0 |
| BD118 | LM118 | 3 | Ir | — | 0 |
| BD119 | LM119 | 3 | Ir | — | 0 |
| BD120 | LM120 | 3 | Ir | — | 0 |
| BD121 | LM121 | 3 | Ir | — | 0 |
| BD122 | LM122 | 3 | Ir | — | 0 |
| BD123 | LM123 | 3 | Ir | — | 0 |
| BD124 | LM124 | 3 | Ir | — | 0 |
| BD125 | LM125 | 3 | Ir | — | 0 |
| BD126 | LM126 | 3 | Ir | — | 0 |
| BD127 | LM127 | 3 | Ir | — | 0 |
| BD128 | LM128 | 3 | Ir | — | 0 |
| BD129 | LM129 | 3 | Ir | — | 0 |
| BD130 | LM130 | 3 | Ir | — | 0 |
| BD131 | LM131 | 3 | Ir | — | 0 |
| BD132 | LM132 | 3 | Ir | — | 0 |
| BD133 | LM133 | 3 | Ir | — | 0 |
| BD134 | LM134 | 3 | Ir | — | 0 |
| BD135 | LM135 | 3 | Ir | — | 0 |
| BD136 | LM136 | 3 | Ir | — | 0 |
| BD137 | LM137 | 3 | Ir | — | 0 |
| BD138 | LM138 | 3 | Ir | — | 0 |
| BD139 | LM139 | 3 | Ir | — | 0 |
| BD140 | LM140 | 3 | Ir | — | 0 |

TABLE 5-continued

| Compound name | $L_{101}$ | n101 | $M_{101}$ | $L_{102}$ | m101 |
|---|---|---|---|---|---|
| BD141 | LM141 | 3 | Ir | — | 0 |
| BD142 | LM142 | 3 | Ir | — | 0 |
| BD143 | LM143 | 3 | Ir | — | 0 |
| BD144 | LM144 | 3 | Ir | — | 0 |
| BD145 | LM145 | 3 | Ir | — | 0 |
| BD146 | LM146 | 3 | Ir | — | 0 |
| BD147 | LM147 | 3 | Ir | — | 0 |
| BD148 | LM148 | 3 | Ir | — | 0 |
| BD149 | LM149 | 3 | Ir | — | 0 |
| BD150 | LM150 | 3 | Ir | — | 0 |
| BD151 | LM151 | 3 | Ir | — | 0 |
| BD152 | LM152 | 3 | Ir | — | 0 |
| BD153 | LM153 | 3 | Ir | — | 0 |
| BD154 | LM154 | 3 | Ir | — | 0 |
| BD155 | LM155 | 3 | Ir | — | 0 |
| BD156 | LM156 | 3 | Ir | — | 0 |
| BD157 | LM157 | 3 | Ir | — | 0 |
| BD158 | LM158 | 3 | Ir | — | 0 |
| BD159 | LM159 | 3 | Ir | — | 0 |
| BD160 | LM160 | 3 | Ir | — | 0 |
| BD161 | LM161 | 3 | Ir | — | 0 |
| BD162 | LM162 | 3 | Ir | — | 0 |
| BD163 | LM163 | 3 | Ir | — | 0 |
| BD164 | LM164 | 3 | Ir | — | 0 |
| BD165 | LM165 | 3 | Ir | — | 0 |
| BD166 | LM166 | 3 | Ir | — | 0 |
| BD167 | LM167 | 3 | Ir | — | 0 |
| BD168 | LM168 | 3 | Ir | — | 0 |
| BD169 | LM169 | 3 | Ir | — | 0 |
| BD170 | LM170 | 3 | Ir | — | 0 |
| BD171 | LM171 | 3 | Ir | — | 0 |
| BD172 | LM172 | 3 | Ir | — | 0 |
| BD173 | LM173 | 3 | Ir | — | 0 |
| BD174 | LM174 | 3 | Ir | — | 0 |
| BD175 | LM175 | 3 | Ir | — | 0 |
| BD176 | LM176 | 3 | Ir | — | 0 |
| BD177 | LM177 | 3 | Ir | — | 0 |
| BD178 | LM178 | 3 | Ir | — | 0 |
| BD179 | LM179 | 3 | Ir | — | 0 |
| BD180 | LM180 | 3 | Ir | — | 0 |
| BD181 | LM181 | 3 | Ir | — | 0 |
| BD182 | LM182 | 3 | Ir | — | 0 |
| BD183 | LM183 | 3 | Ir | — | 0 |
| BD184 | LM184 | 3 | Ir | — | 0 |
| BD185 | LM185 | 3 | Ir | — | 0 |
| BD186 | LM186 | 3 | Ir | — | 0 |
| BD187 | LM187 | 3 | Ir | — | 0 |
| BD188 | LM188 | 3 | Ir | — | 0 |
| BD189 | LM189 | 3 | Ir | — | 0 |
| BD190 | LM190 | 3 | Ir | — | 0 |
| BD191 | LM191 | 3 | Ir | — | 0 |
| BD192 | LM192 | 3 | Ir | — | 0 |
| BD193 | LM193 | 3 | Ir | — | 0 |
| BD194 | LM194 | 3 | Ir | — | 0 |
| BD195 | LM195 | 3 | Ir | — | 0 |
| BD196 | LM196 | 3 | Ir | — | 0 |
| BD197 | LM197 | 3 | Ir | — | 0 |
| BD198 | LM198 | 3 | Ir | — | 0 |
| BD199 | LM199 | 3 | Ir | — | 0 |
| BD200 | LM200 | 3 | Ir | — | 0 |

TABLE 6

| Compound name | $L_{101}$ | n101 | $M_{101}$ | $L_{102}$ | m101 |
|---|---|---|---|---|---|
| BD201 | LM201 | 3 | Ir | — | 0 |
| BD202 | LM202 | 3 | Ir | — | 0 |
| BD203 | LM203 | 3 | Ir | — | 0 |
| BD204 | LM204 | 3 | Ir | — | 0 |
| BD205 | LM205 | 3 | Ir | — | 0 |
| BD206 | LM206 | 3 | Ir | — | 0 |
| BD207 | LM207 | 3 | Ir | — | 0 |
| BD208 | LM208 | 3 | Ir | — | 0 |
| BD209 | LM209 | 3 | Ir | — | 0 |
| BD210 | LM210 | 3 | Ir | — | 0 |
| BD211 | LM211 | 3 | Ir | — | 0 |
| BD212 | LM212 | 3 | Ir | — | 0 |
| BD213 | LM213 | 3 | Ir | — | 0 |
| BD214 | LM214 | 3 | Ir | — | 0 |
| BD215 | LM215 | 3 | Ir | — | 0 |
| BD216 | LM216 | 3 | Ir | — | 0 |
| BD217 | LM217 | 3 | Ir | — | 0 |
| BD218 | LM218 | 3 | Ir | — | 0 |
| BD219 | LM219 | 3 | Ir | — | 0 |
| BD220 | LM220 | 3 | Ir | — | 0 |
| BD221 | LM221 | 3 | Ir | — | 0 |
| BD222 | LM222 | 3 | Ir | — | 0 |
| BD223 | LM223 | 3 | Ir | — | 0 |
| BD224 | LM224 | 3 | Ir | — | 0 |
| BD225 | LM225 | 3 | Ir | — | 0 |
| BD226 | LM226 | 3 | Ir | — | 0 |
| BD227 | LM227 | 3 | Ir | — | 0 |
| BD228 | LM228 | 3 | Ir | — | 0 |
| BD229 | LM229 | 3 | Ir | — | 0 |
| BD230 | LM230 | 3 | Ir | — | 0 |
| BD231 | LM231 | 3 | Ir | — | 0 |
| BD232 | LM232 | 3 | Ir | — | 0 |
| BD233 | LM233 | 3 | Ir | — | 0 |
| BD234 | LM234 | 3 | Ir | — | 0 |
| BD235 | LM235 | 3 | Ir | — | 0 |
| BD236 | LM236 | 3 | Ir | — | 0 |
| BD237 | LM237 | 3 | Ir | — | 0 |
| BD238 | LM238 | 3 | Ir | — | 0 |
| BD239 | LM239 | 3 | Ir | — | 0 |
| BD240 | LM240 | 3 | Ir | — | 0 |
| BD241 | LM241 | 3 | Ir | — | 0 |
| BD242 | LM242 | 3 | Ir | — | 0 |
| BD243 | LM243 | 3 | Ir | — | 0 |
| BD244 | LFM1 | 3 | Ir | — | 0 |
| BD245 | LFM2 | 3 | Ir | — | 0 |
| BD246 | LFM3 | 3 | Ir | — | 0 |
| BD247 | LFM4 | 3 | Ir | — | 0 |
| BD248 | LFM5 | 3 | Ir | — | 0 |
| BD249 | LFM8 | 3 | Ir | — | 0 |
| BD250 | LFM7 | 3 | Ir | — | 0 |
| BD251 | LFP1 | 3 | Ir | — | 0 |
| BD252 | LFP2 | 3 | Ir | — | 0 |
| BD253 | LFP3 | 3 | Ir | — | 0 |
| BD254 | LFP4 | 3 | Ir | — | 0 |
| BD255 | LFP5 | 3 | Ir | — | 0 |
| BD256 | LFP6 | 3 | Ir | — | 0 |
| BD257 | LFP7 | 3 | Ir | — | 0 |
| BD258 | LM47 | 2 | Ir | AN1 | 1 |
| BD259 | LM47 | 2 | Ir | AN2 | 1 |
| BD260 | LM47 | 2 | Ir | AN3 | 1 |
| BD261 | LM47 | 2 | Ir | AN4 | 1 |
| BD262 | LM47 | 2 | Ir | AN5 | 1 |
| BD263 | LM11 | 2 | Pt | — | 0 |
| BD264 | LM13 | 2 | Pt | — | 0 |
| BD265 | LM15 | 2 | Pt | — | 0 |
| BD266 | LM45 | 2 | Pt | — | 0 |
| BD267 | LM47 | 2 | Pt | — | 0 |
| BD268 | LM49 | 2 | Pt | — | 0 |
| BD269 | LM98 | 2 | Pt | — | 0 |
| BD270 | LM100 | 2 | Pt | — | 0 |
| BD271 | LM102 | 2 | Pt | — | 0 |
| BD272 | LM132 | 2 | Pt | — | 0 |
| BD273 | LM134 | 2 | Pt | — | 0 |
| BD274 | LM136 | 2 | Pt | — | 0 |
| BD275 | LM151 | 2 | Pt | — | 0 |
| BD276 | LM153 | 2 | Pt | — | 0 |
| BD277 | LM158 | 2 | Pt | — | 0 |
| BD278 | LM180 | 2 | Pt | — | 0 |
| BD279 | LM182 | 2 | Pt | — | 0 |
| BD280 | LM187 | 2 | Pt | — | 0 |
| BD281 | LM201 | 2 | Pt | — | 0 |
| BD282 | LM206 | 2 | Pt | — | 0 |
| BD283 | LM211 | 2 | Pt | — | 0 |
| BD284 | LM233 | 2 | Pt | — | 0 |
| BD285 | LM235 | 2 | Pt | — | 0 |

TABLE 6-continued
| Compound name | $L_{101}$ | n101 | $M_{101}$ | $L_{102}$ | m101 |
|---|---|---|---|---|---|
| BD286 | LM240 | 2 | Pt | — | 0 |
| BD287 | LFM5 | 2 | Pt | — | 0 |
| BD288 | LFM6 | 2 | Pt | — | 0 |
| BD289 | LFM7 | 2 | Pt | — | 0 |
| BD290 | LFP5 | 2 | Pt | — | 0 |
| BD291 | LFP6 | 2 | Pt | — | 0 |
| BD292 | LFP7 | 2 | Pt | — | 0 |
| BD293 | LM47 | 1 | Pt | AN1 | 1 |
| BD294 | LM47 | 1 | Pt | AN2 | 1 |
| BD295 | LM47 | 1 | Pt | AN3 | 1 |
| BD296 | LM47 | 1 | Pt | AN4 | 1 |
| BD297 | LM47 | 1 | Pt | AN5 | 1 |
In Tables 4 to 6, LM1 to LM243, LFM1 to LFM7, LFP1 to LFP7, and AN1 to AN5 may be understood based on those described above.
For example, some of compounds BD001 to BD297 may be represented as follows.
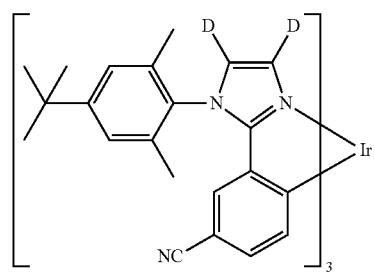
BD037
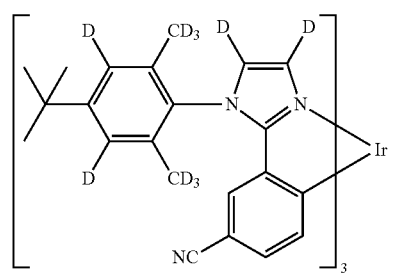
BD040
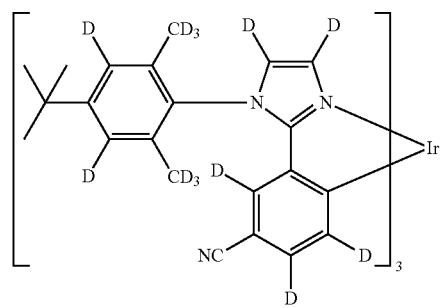
BD044
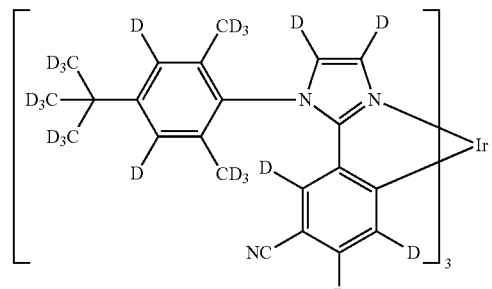
BD045
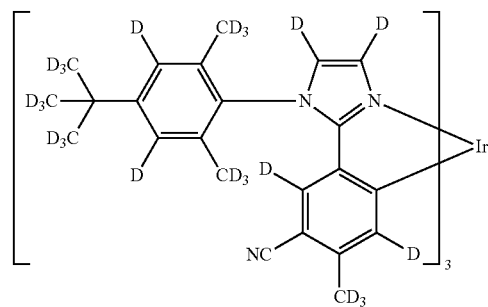
BD047
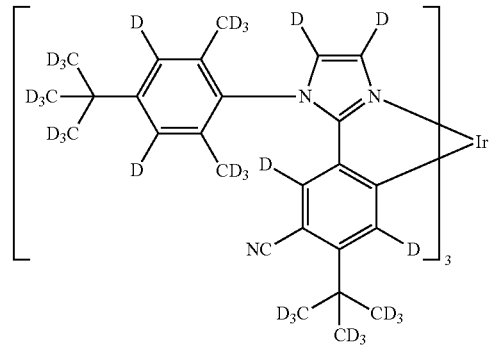
BD049
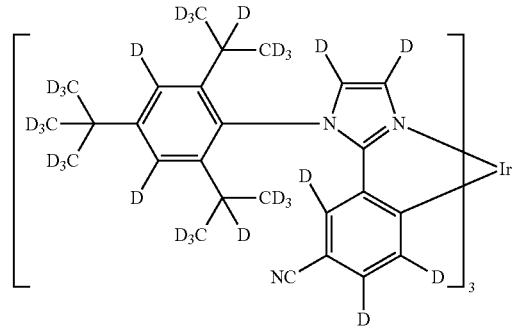
BD064

BD079
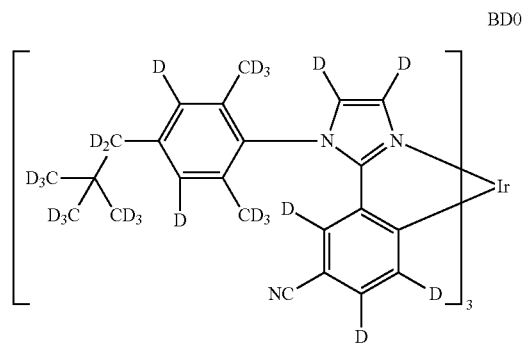
BD151
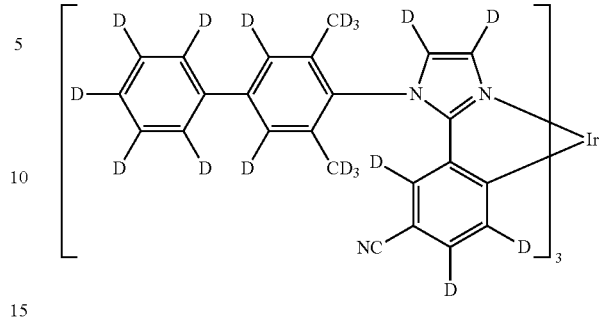
BD098
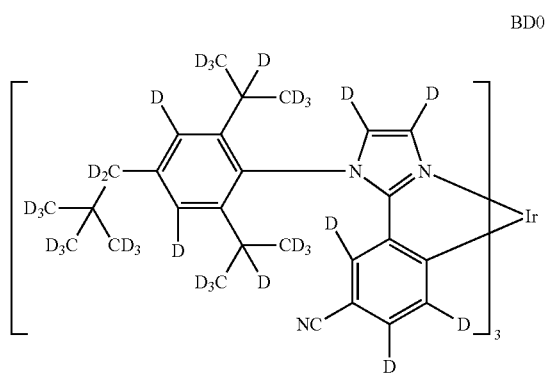
BD180
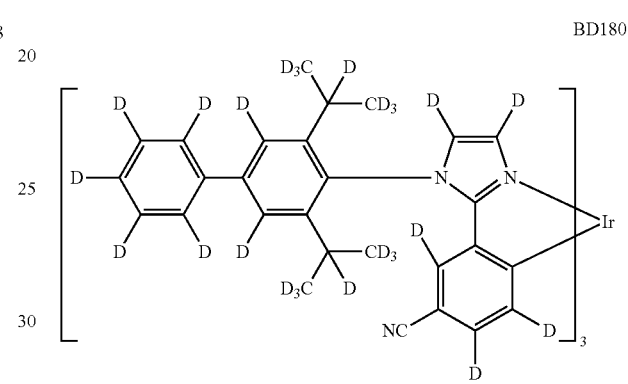
BD113
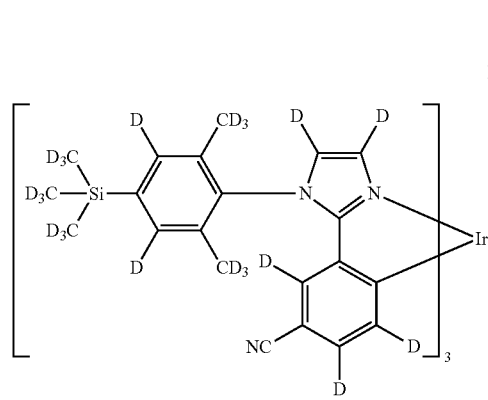
BD201
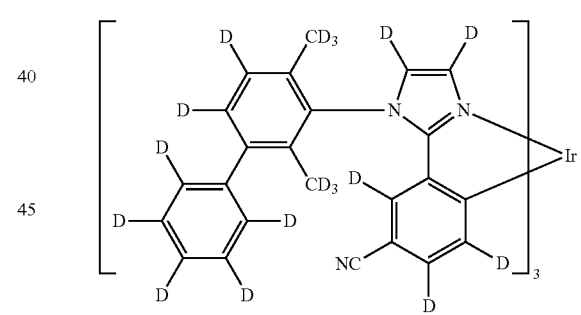
BD132
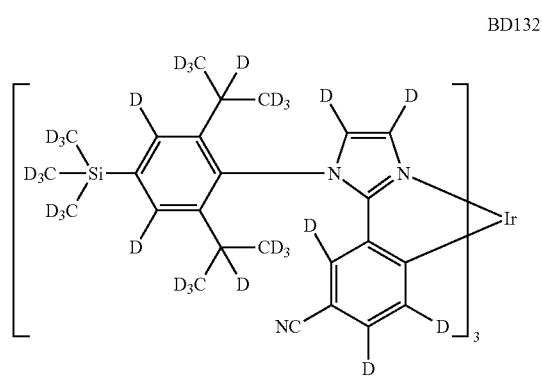
BD233
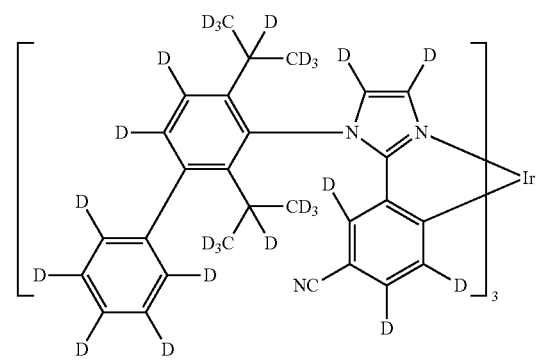

-continued

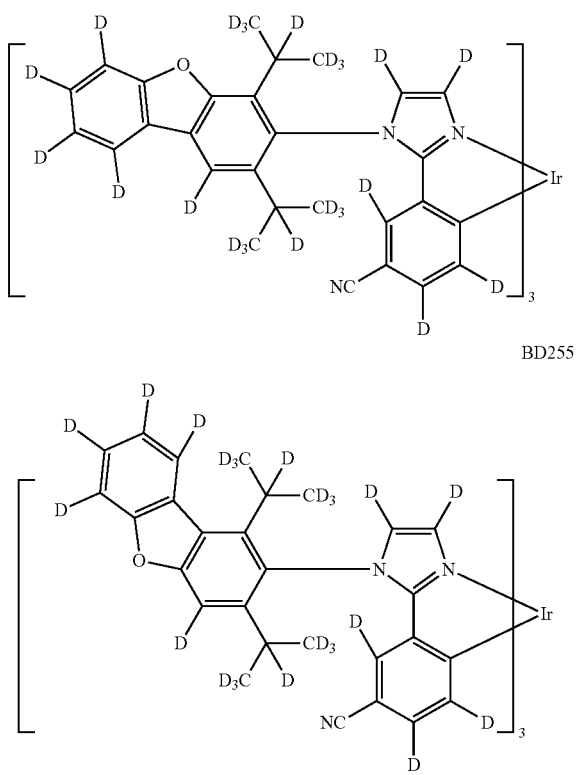

BD248

BD255

The organometallic compound of Formula 1 may have a maximum emission wavelength of about 420 nanometers (nm) to about 480 nm or less, and in some embodiments, about 440 nm to about 465 nm. When the organometallic compound has a maximum emission wavelength of 480 nm or less, an organic light-emitting device including the organometallic compound may have blue emission color. For example, when the organometallic compound has a maximum emission wavelength of 465 nm or less, an organic light-emitting device including the organometallic compound may have deep blue emission color.

The organometallic compound of Formula 1 may provide deep blue emission color when it includes "a cyano group" at a "certain position".

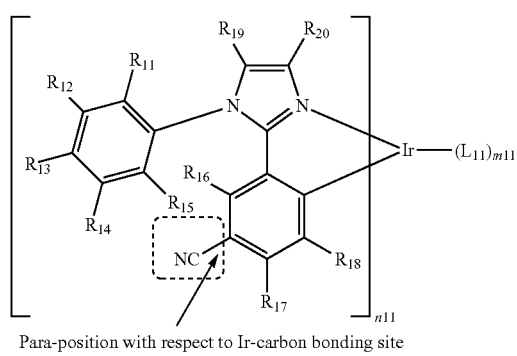

Formula 1'

Para-position with respect to Ir-carbon bonding site

As shown in Formula 1', when a cyano group is at a para position with respect to a Ir—C binding site, the organometallic compound of Formula 1 may have a deep highest occupied molecular orbital (HOMO) energy level. Accordingly, the organometallic compound of Formula 1 may have a high triplet energy level due to an increased band gap, and thus provide deep blue emission color.

The organometallic compound of Formula 1 essentially includes "deuterium", and thus may have improved thermal stability. In particular, a carbon-deuterium single bond has a stronger bond strength than a carbon-hydrogen single bond, and thus the amount of byproducts that may be produced due to radicalization and/or oxidation-reduction by heat and/or an electric field applied during the synthesis of the organometallic compound of Formula 1, a sublimation purification process, deposition in the manufacturing of an organic light-emitting device, and/or storage and/or operation of an organic light-emitting device may be considerably reduced. The organometallic compound of Formula 1 may suppress the generation of byproducts that are fatal to the lifespan of an organic light-emitting device. Therefore, an organic light-emitting device including the organometallic compound of Formula 1 may have an improved lifespan.

The organometallic compound represented by Formula 1 essentially includes a "bulky unit" such as a branched alkyl group, an aryl group, or the like, so that aggregation of the organometallic compound may be suppressed during deposition, and the organometallic compound may be deposited in a uniform ratio with respect to a host in an emission layer. Therefore, an organic light-emitting device including the organometallic compound of Formula 1 may prevent exciton quenching caused by aggregation, and thus may have improved efficiency and an improved lifespan.

In synthesizing the organometallic compound of Formula 1, when 100% deuteration does not occur in the organometallic compound, an organometallic compound that includes a hydrogen not substituted with deuterium may also be synthesized together with the organometallic compound of Formula 1.

In this regard, according to another aspect of the present disclosure, there is provided an organometallic compound-containing composition that includes the organometallic compound (also referred to as a "first organometallic compound") represented by Formula 1 and an organometallic compound (also referred to as a "second organometallic compound") represented by Formula 2,

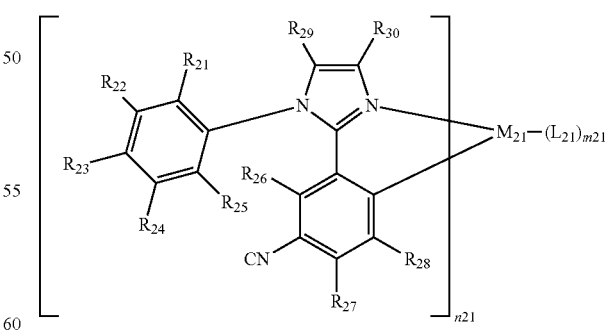

Formula 2

In Formula 2, $M_{21}$ may be selected from a first-row transition metal, a second-row transition metal, and a third-row transition metal.

For example, in Formula 2, $M_{21}$ may be selected from iridium (Ir), platinum (Pt), osmium (Os), ruthenium (Ru), rhodium (Rh), palladium (Pd), copper (Cu), silver (Ag), gold (Au), titanium (Ti), zirconium (Zr), hafnium (Hf), europium (Eu), terbium (Tb), and thulium (Tm). However, embodiments are not limited thereto.

In some embodiments, in Formula 2, $M_{21}$ may be selected from Ir, Pt, and Os. However, embodiments are not limited thereto.

In some other embodiments, in Formula 2, $M_{21}$ may be selected from Ir and Pt. However, embodiments are not limited thereto.

In Formula 2, $R_{21}$ to $R_{28}$ may be each independently selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group, wherein optionally, at least two of $R_{21}$ to $R_{25}$ may be linked to form a substituted or unsubstituted saturated ring, or a substituted or unsubstituted unsaturated ring.

For example, in Formula 2, $R_{21}$ to $R_{28}$ may be each independently selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group, wherein optionally, adjacent two of $R_{21}$ to $R_{25}$ may be linked to form a substructure represented by Formula 20. However, embodiments are not limited thereto.

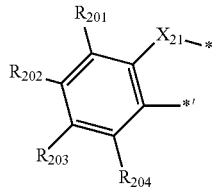

Formula 20

In Formula 20, $X_{21}$ may be selected from O, S, and $N(R_{205})$;

$R_{201}$ to $R_{205}$ may be each independently selected from a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and a substituted or unsubstituted $C_1$-$C_{30}$ alkylsilyl group; and

* and *' may be each independently a carbon atom to which adjacent two of $R_{21}$ to $R_{25}$ are bound.

In some embodiments, in Formula 2, $R_{21}$ to $R_{28}$ may be each independently selected from a hydrogen, —F, —Cl, —Br, —I, a cyano group, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group, wherein optionally, adjacent two of $R_{21}$ to $R_{25}$ may be linked to form a substructure represented by Formula 20. However, embodiments are not limited thereto.

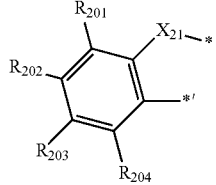

Formula 20

In Formula 20, $X_{21}$ may be selected from O, S, and $N(R_{205})$;

$R_{201}$ to $R_{205}$ may be each independently selected from a hydrogen, —F, —Cl, —Br, —I, a cyano group, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group; and

* and *' may be each independently a carbon atom to which adjacent two of $R_{21}$ to $R_{25}$ are bound, In some embodiments, in Formula 2, $R_{21}$ to $R_{28}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, and —Si($Q_1$)($Q_2$)($Q_3$), a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of —F, —Cl, —Br, —I, and a cyano group, and a phenyl group, a biphenyl group, a terphenyl group, a naphthyl group, a phenanthrenyl group, an anthracenyl group, a triphenylenyl group, a pyrenyl group, and a chrysenyl group, each substituted with at least one of —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, wherein $Q_1$ to $Q_3$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, wherein optionally, adjacent two of $R_{21}$ to $R_{25}$ may be linked to form a substructure represented by Formula 20. However, embodiments are not limited thereto.

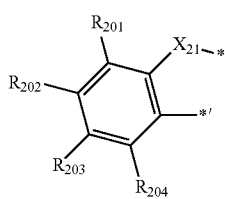

Formula 20

In Formula 20,
$X_{21}$ may be selected from O, S, and N($R_{205}$);
$R_{201}$ to $R_{205}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group; and

* and *' may be each independently a carbon atom to which adjacent two of $R_{21}$ to $R_{25}$ are bound.

In some embodiments, in Formula 2, $R_{21}$ to $R_{28}$ may be each independently selected from a hydrogen, —F, —Cl, —Br, —I, a cyano group, a methyl group, an iso-propyl group, an iso-butyl group, a tert-butyl group, a neo-pentyl group, a phenyl group, a biphenyl group, and —Si($Q_1$)($Q_2$)($Q_3$), a methyl group, an iso-propyl group, an iso-butyl group, a tert-butyl group, and a neo-pentyl group, each substituted with at least one of —F, —Cl, —Br, —I, and a cyano group, and a phenyl group and a biphenyl group, each substituted with at least one of —F, —Cl, —Br, —I, a cyano group, a methyl group, an iso-propyl group, an iso-butyl group, a tert-butyl group, and a neo-pentyl group;

$Q_1$ to $Q_3$ may be each independently selected from a methyl group, an iso-propyl group, an iso-butyl group, a tert-butyl group, and a neo-pentyl group; and optionally, $R_{22}$ and $R_{23}$ are linked to form a substructure represented by Formula 20. However, embodiments are not limited thereto:

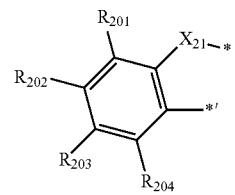

Formula 20

In Formula 20,
$X_{21}$ may be selected from O, S, and N($R_{205}$);
$R_{201}$ to $R_{205}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group; a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group; a phenanthrenyl group, an anthracenyl group; a triphenylenyl group, a pyrenyl group, and a chrysenyl group; and

* and *' may be each independently a carbon atom to which $R_{22}$ and $R_{23}$ are bound.

In some other embodiments; in Formula 2; $R_{21}$ to $R_{28}$ may be each independently selected from a hydrogen, a methyl group, an iso-propyl group, an iso-butyl group, a tert-butyl group, a neo-pentyl group, a phenyl group; a biphenyl group, and —Si(CH$_3$)$_3$; and optionally, $R_{22}$ and $R_{23}$ may be linked to form a substructure represented by Formula 20. However, embodiments are not limited thereto.

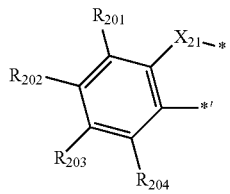

Formula 20

In Formula 20,
$X_{21}$ may be selected from O, S, and N($R_{205}$)
$R_{201}$ to $R_{235}$ may be each independently selected from a hydrogen, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, and a chrysenyl group; and

* and *' may be each independently a carbon atom to which $R_{22}$ to $R_{23}$ are bound.

In some embodiments, in Formula 2, at least one of $R_{21}$ to $R_{25}$ may be selected from a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group.

For example, in Formula 2, at least one of $R_{21}$ to $R_{25}$ may be selected from a substituted or unsubstituted $C_3$-$C_{30}$ branched alkyl group, a substituted or unsubstituted $C_6$-$C_{30}$ aryl group, a substituted or unsubstituted $C_1$-$C_{30}$ heteroaryl group, and a substituted or unsubstituted $C_1$-$C_{30}$ alkylsilyl group. However, embodiments are not limited thereto.

In some other embodiments, in Formula 2, at least one of $R_{21}$ to $R_{25}$ may be selected from a substituted or unsubstituted $C_3$-$C_{30}$ branched alkyl group, a substituted or unsubstituted $C_6$-$C_{30}$ aryl group, and a substituted or unsubstituted $C_1$-$C_{30}$ alkylsilyl group. However, embodiments are not limited thereto.

In some other embodiments, in Formula 2, at least one of $R_{21}$ to $R_{25}$ may be selected from an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, and —Si(Q$_1$)(Q$_2$)(Q$_3$), an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, and a tert-pentyl group, each substituted with at least one of —F, —Cl, —Br, —I, and a cyano group, and a phenyl group, a biphenyl group, a terphenyl group, a naphthyl group, a phenanthrenyl group, an anthracenyl group, a triphenylenyl group, a pyrenyl group, and a chrysenyl group, each substituted with at least one of —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, wherein $Q_1$ to $Q_3$ may be each independently selected from a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group. However, embodiments are not limited thereto.

In some embodiments, in Formula 2, at least one of $R_{21}$ to $R_{25}$ may be selected from an iso-propyl group, an iso-butyl group, a tert-butyl group, a neo-pentyl group, a phenyl group, a biphenyl group, and —Si(Q$_1$)(Q$_2$)(Q$_3$), an iso-propyl group, an iso-butyl group, a tert-butyl group, and a neo-pentyl group, each substituted with at least one of —F, —Cl, —Br, —I, and a cyano group, and a phenyl group, and a biphenyl group, each substituted with at least one of —F, —Cl, —Br, —I, a cyano group, a methyl group, an iso-propyl group, an iso-butyl group, a tert-butyl group, and a neo-pentyl group, wherein $Q_1$ to $Q_3$ may be each independently selected from a methyl group, an iso-propyl group, an iso-butyl group, a tert-butyl group, and a neo-pentyl group. However, embodiments are not limited thereto.

In some embodiments, in Formula 2, at least one of $R_{21}$ to $R_{25}$ may be selected from an iso-propyl group, an iso-butyl group, a tert-butyl group, a neo-pentyl group, a phenyl group, a biphenyl group, and —Si(Q$_1$)(Q$_2$)(Q$_3$), an iso-propyl group, an iso-butyl group, a tert-butyl group, and a neo-pentyl group, each substituted with at least one of —F, —Cl, —Br, —I, and a cyano group, and a phenyl group and a biphenyl group, each substituted with at least one of —F, —Cl, —Br, —I, a cyano group, a methyl group, an iso-propyl group, an iso-butyl group, a tert-butyl group, and a neo-pentyl group, wherein $Q_1$ to $Q_3$ may be each independently selected from a methyl group, an iso-propyl group, an iso-butyl group, a tert-butyl group, and a neo-pentyl group. However, embodiments are not limited thereto.

In some other embodiments, in Formula 2, at least one of $R_{21}$ to $R_{25}$ may be selected from an iso-propyl group, an iso-butyl group, a tert-butyl group, a neo-pentyl group, a phenyl group, a biphenyl group, and —Si(CH$_3$)$_3$. However, embodiments are not limited thereto.

In some embodiments, in Formula 2, $R_{21}$ and $R_{22}$, $R_{22}$ and $R_{23}$, $R_{23}$ and $R_{24}$, or $R_{24}$ and $R_{25}$ may be optionally linked to each other to form a condensed ring, but embodiments are not limited thereto.

In some embodiments, in Formula 2, $R_{25}$ and $R_{26}$ may be optionally linked to each other via a single bond, but embodiments are not limited thereto.

In Formula 2, $R_{29}$ and $R_{30}$ may be each independently selected from a hydrogen and a $C_1$-$C_{30}$ alkyl group.

In some embodiments, in Formula 2, $R_{29}$ and $R_{30}$ may be each independently selected from a hydrogen, a methyl group, an ethyl group, an n-propyl group, an iso-propyl group, an n-butyl group, a sec-butyl group, an iso-butyl group, and a tert-butyl group, but embodiments are not limited thereto.

In some embodiments, in Formula 2, $R_{29}$ and $R_{30}$ may be both a hydrogen, but embodiments are not limited thereto.

In Formula 2, $R_{21}$ to $R_{30}$ may be each independently a deuterium-non-containing substituent.

As used herein, the term "deuterium-non-containing substituent" may refer to a substituent no hydrogen is substituted with deuterium.

In Formula 2, a moiety represented by

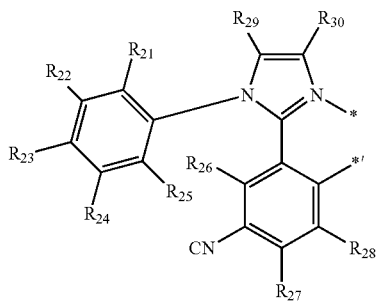

(wherein * and *' each indicate a binding site to $M_{21}$ in Formula 2) may not include a deuterium. For example, the organometallic compound-containing composition that includes the first organometallic compound and the second organometallic compound may have a deuteration rate, which is represented by Equation 2, of 50% or more, but embodiments are not limited thereto:

$$\text{Deuteration rate } (\%) = n_{D2}/(n_{H2}+n_{D2}) \times 100 \qquad \text{Equation 2}$$

In Equation 2, $n_{H2}$ represents a sum of a total number of hydrogens in the deuterium-containing substituents and a total number of hydrogens in substituents that are equivalent to the deuterium-containing substituents; and $n_{D2}$ represents a total number of deuterium atoms in the deuterium-containing substituents.

If a substituent in the dashed region in Compound 1' is a deuterium-containing substituent, the "substituents that are equivalent to the deuterium-containing substituents" used herein may include a substituent in the dashed region in Compound 1". That is, substituents bound at the same carbon location in two compounds that are the same except for having or not having an isotope thereof are defined as "equivalent" substituents.

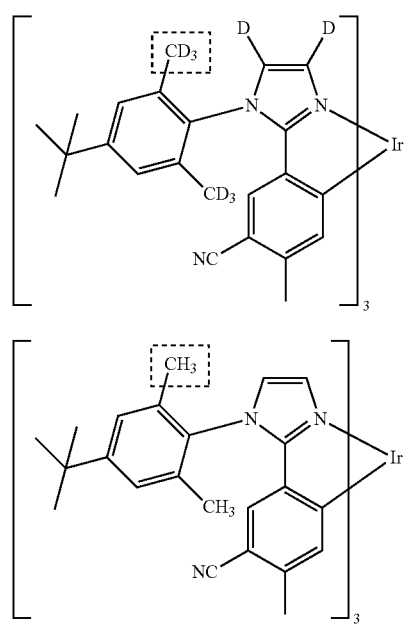

For example, when the first organometallic compound includes two deuterium-containing substituents, $n_{D2}$ indicates the total number of deuterium atoms included in the two deuterium-containing substituents. In addition, $n_{H2}$ indicates the total number of hydrogens included in the two deuterium-containing substituents and the total number of hydrogens included in substituents corresponding to the two deuterium-containing substituents.

In some embodiments, the deuteration rate may be 70% or more, 90% or more, 95% or more, 96% or more, 97% or more, 98% or more, or 99% or more, but embodiments are not limited thereto.

A method of synthesizing the organometallic compound represented by Formula 1 may be obvious to one of ordinary skill in the art by referring to Synthesis Examples used herein. The organometallic compound-containing composition may be obtained as a result of imperfect deuteration during the synthesis of the organometallic compound represented by Formula 1, not by further adding at least one second organometallic compound, The organometallic compound of Formula 1 or the organometallic compound-containing composition may be appropriate for use as a material for an organic layer of an organic light-emitting device, for example, as a dopant of an EML.

According to another aspect of the present disclosure, an organic light-emitting device includes:

a first electrode, a second electrode, and an organic layer that is disposed between the first electrode and the second electrode, wherein the organic layer includes an EML and an organometallic compound of Formula 1 or an organometallic compound-containing composition according to any of the above-described embodiments.

Due to the inclusion of the organic layer that includes an organometallic compound of Formula 1 or an organometallic compound-containing composition according to any of the above-described embodiments, the organic light-emitting device may have improved efficiency, lifespan, and color purity characteristics.

The organometallic compound of Formula 1 or the organometallic compound-containing composition may be used between a pair of electrodes of an organic light-emitting device. For example, the organometallic compound of Formula 1 or the organometallic compound-containing composition may be included in the EML. In this regard, the organometallic compound of Formula 1 may serve as a dopant in the EML, and the EML may further include a host. The EML may emit red light, green light, or blue light.

As used herein, "(for example, the organic layer) including an organometallic compound" means that "(the organic layer) including an organometallic compound of Formula 1 above, or at least two different organometallic compounds of Formula 1 above".

For example, the organic layer of the organic light-emitting device may include only Compound 1 as the organometallic compound. For example, Compound 1 may be included in the EML of the organic light-emitting device. In some embodiments, the organic layer of the organic light-emitting device may include Compounds 1 and 2 as the organometallic compound. For example, Compounds 1 and 2 may be included both in the EML.

The first electrode may be an anode as a hole injection electrode, and the second electrode may be a cathode as an electron injection electrode. In some embodiments, the first electrode may be a cathode as an electron injection electrode, and the second electrode may be an anode as a hole injection electrode.

For example, the first electrode may be an anode, the second electrode may be a cathode, and the organic layer may include:

i) a hole transport region disposed between the first electrode and the emission layer, wherein the hole transport region includes at least one of a hole injection layer, a hole transport layer, and an electron blocking layer; and ii) an electron transport region disposed between the emission layer and the second electrode, wherein the electron transport region includes at least one of a hole blocking layer, an electron transport layer, and an electron injection layer.

The term "organic layer" as used herein refers to a single layer and/or a plurality of layers disposed between the first and second electrodes of the organic light-emitting device. The "organic layer" may include, for example, an organic compound or an organometallic complex including a metal.

FIG. 1 is a schematic view of an organic light-emitting device 10 according to an embodiment of the present disclosure. Hereinafter, a structure of an organic light-emitting device according to an embodiment of the present disclosure and a method of manufacturing the same will now be described with reference to FIG. 1. Referring to FIG. 1, the organic light-emitting device 10 has a structure in which a first electrode 11, an organic layer 15, and a second electrode 19 are sequentially stacked in this order on a substrate (not shown).

The substrate (not shown) may be disposed under the first electrode 11 or on the second electrode 19 in FIG. 1. The substrate may be any substrate that is used in conventional organic light-emitting devices. In some embodiments the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate. The first electrode 11 may be an anode. A material having a high work function may be selected as a material for the first electrode 11 to facilitate hole injection. The first electrode 11 may be a reflective electrode, a semi-transmissive electrode, or a transmissive electrode. For example, the material for the first electrode 11 may be indium tin oxide (ITO), indium zinc oxide (IZO), tin oxide ($SnO_2$), or zinc oxide (ZnO). In some embodiments, the material for the first electrode 11 may be metals, for example, magnesium (Mg), aluminum (Al), aluminum-lithium (Al—Li), calcium (Ca), magnesium-indium (Mg—In), magnesium-silver (Mg—Ag), or the like.

The first electrode 11 may have a single-layer structure or a multi-layer structure including at least two layers. For example, the first electrode 11 may have, but not limited to, a three-layered structure including ITO, Ag, and ITO layers.

The organic layer 15 may be disposed on the first electrode 11.

The organic layer 15 may include at least one a hole transport region; an EML, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may only include the HIL or the HTL. In some embodiments, the electron transport region may have a structure including a HIL/HTL or a HIL/HTL/EBL, wherein the layers forming the structure of the electron transport region may be sequentially stacked on the first electrode 10 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like.

When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100 t to about 500° C., a pressure of about $10^{-8}$ torr to about $10^{-3}$ torr, and a deposition rate of about 0.01 to about 100 Angstroms per second (Å/sec). However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C. However, the coating conditions are not limited thereto.

Conditions for forming the HTL and the EBL may be the same as those for the HIL described above.

In some embodiments, the hole transport region may include at least one of m-MTDATA, TDATA, 2-TNATA, methylated NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate)(PEDOTIPSS), polyaniline/camphor sulfonic acid (Pani/CSA), polyaniline/poly(4-styrenesulfonate) (PANUPSS), a compound represented by Formula 201, and a compound represented by Formula 202.

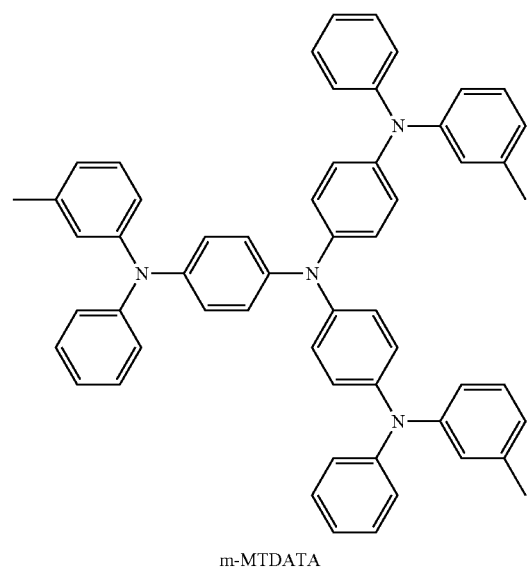

m-MTDATA

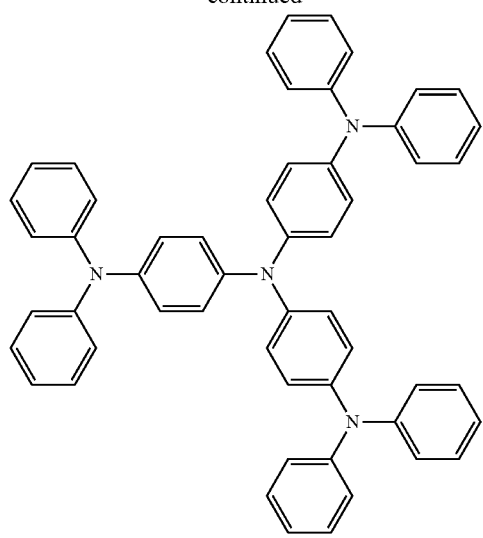
TDATA
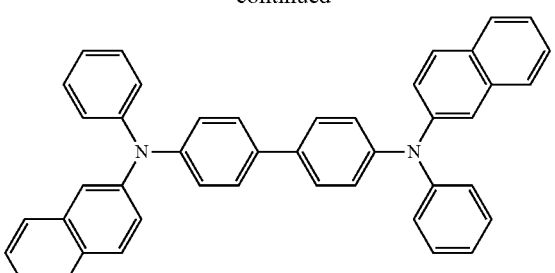
β-NPB
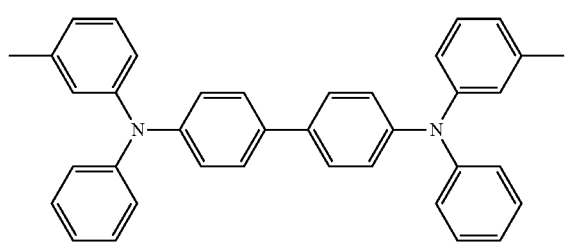
TPD
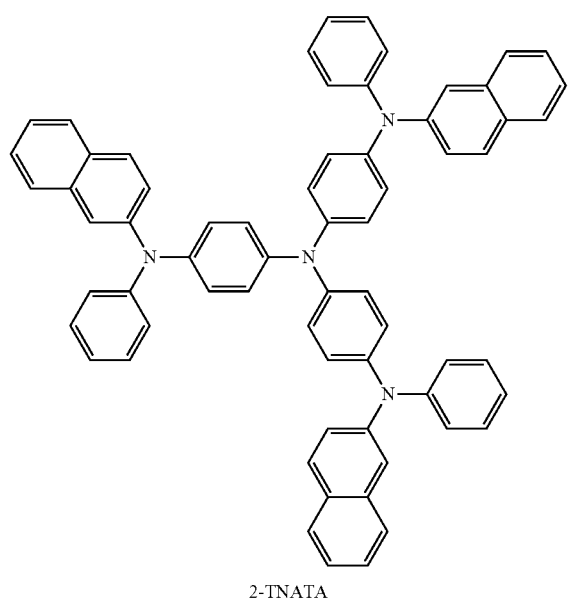
2-TNATA
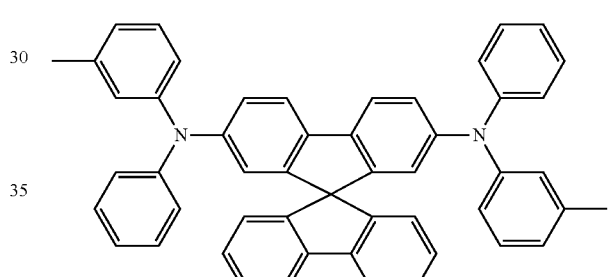
Spiro-TPD
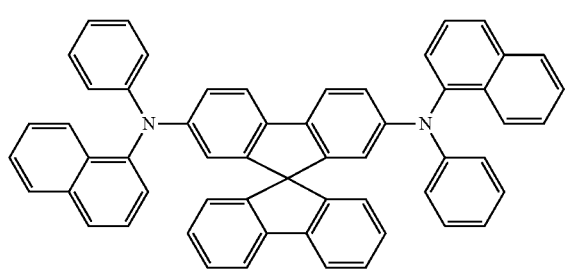
Spiro-NPB
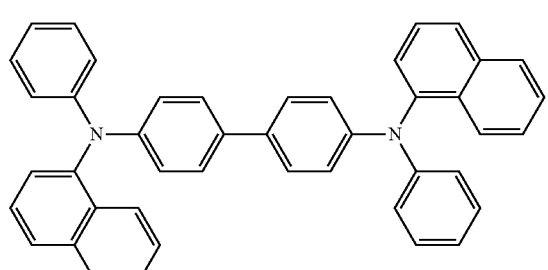
NPB
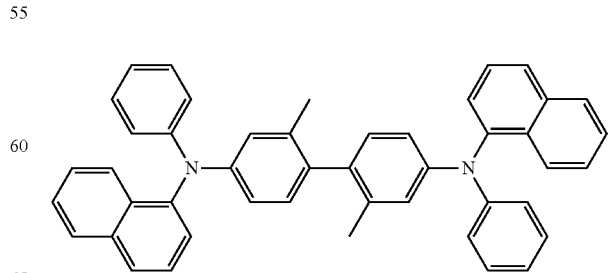
methylated NPB -continued

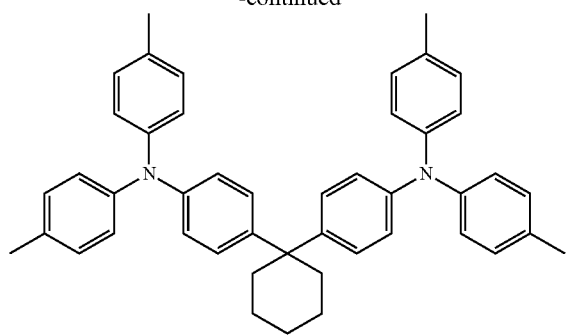

TAPC

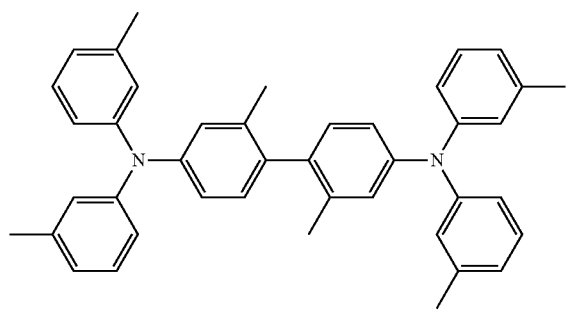

HMTPD

Formula 201

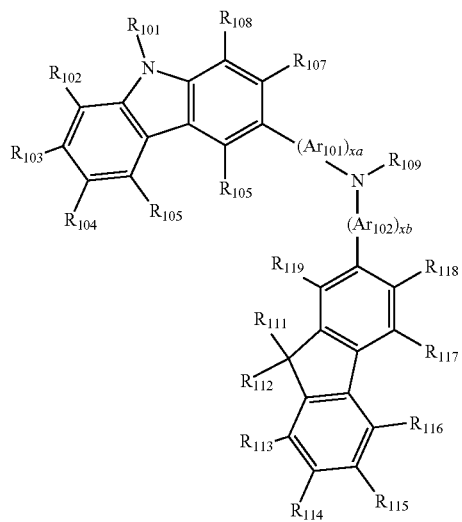

Formula 202

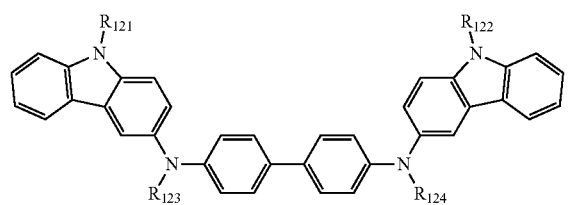

In Formula 201 $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_2$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group, and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be selected from
a phenyl group, a naphthyl group, an anthracenyl group, and a pyridinyl group, or
a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group, In some embodiments, the compound of Formula 201 may be a compound represented by Formula 201A, but is not limited thereto:

Formula 201A

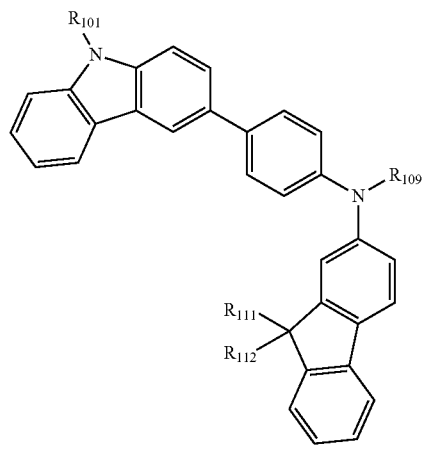

In Formula 201A, $R_{101}$, $R_{111}$, $R_{112}$, and $R_{109}$ may be defined the same as described above, For example, the compound of Formula 201 and the compound of Formula 202 may be Compounds HT1 to HT20, but are not limited thereto:

HT1

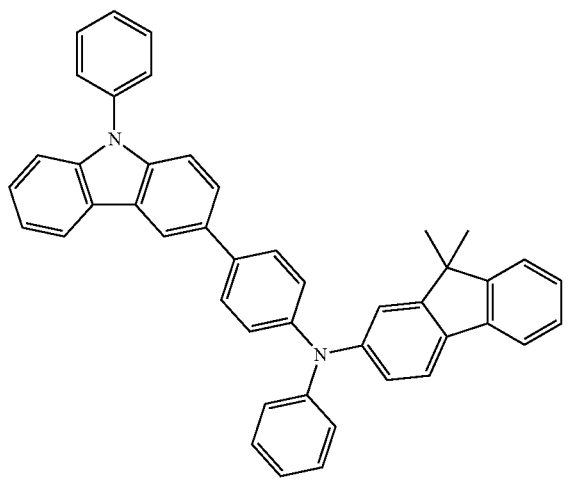

HT2

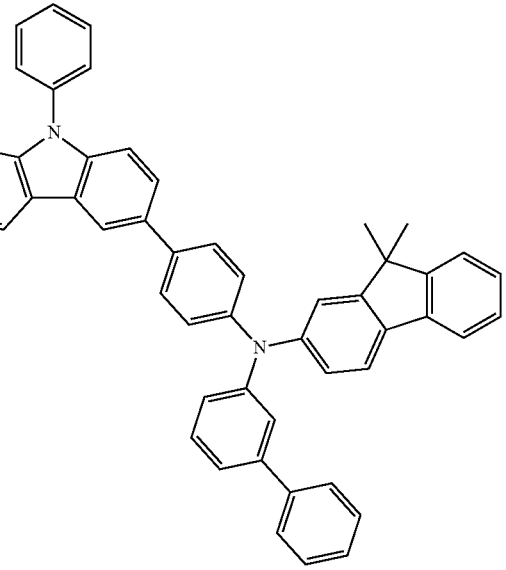

HT3

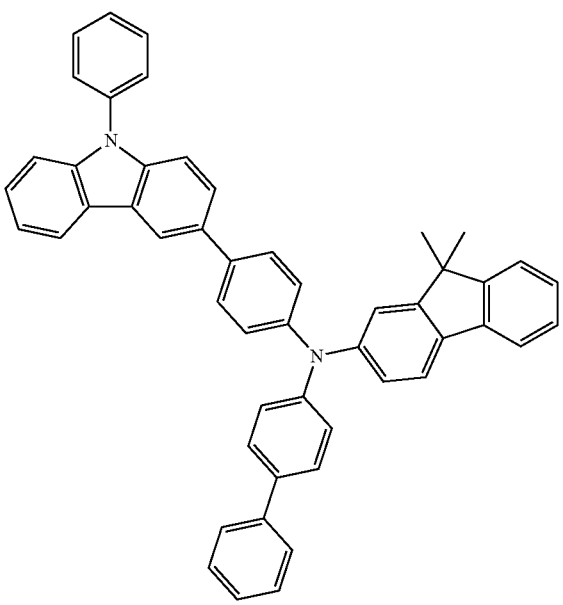

HT4
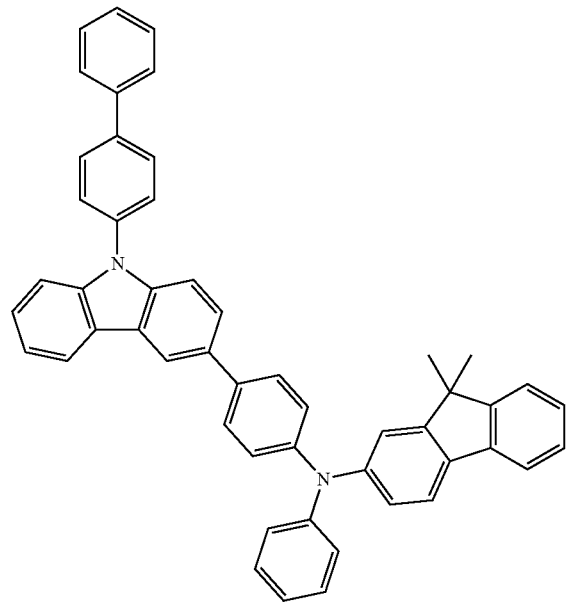
HT5
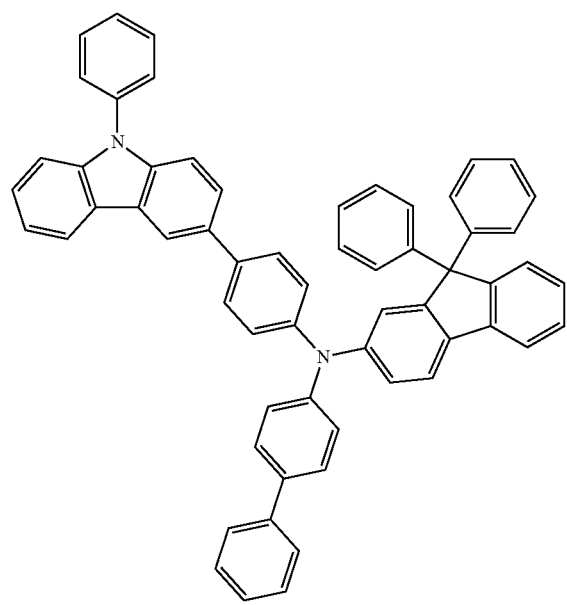
HT6
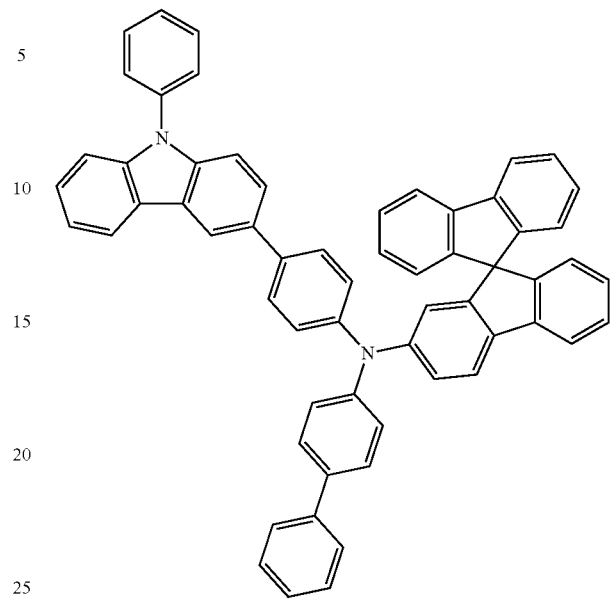
HT7
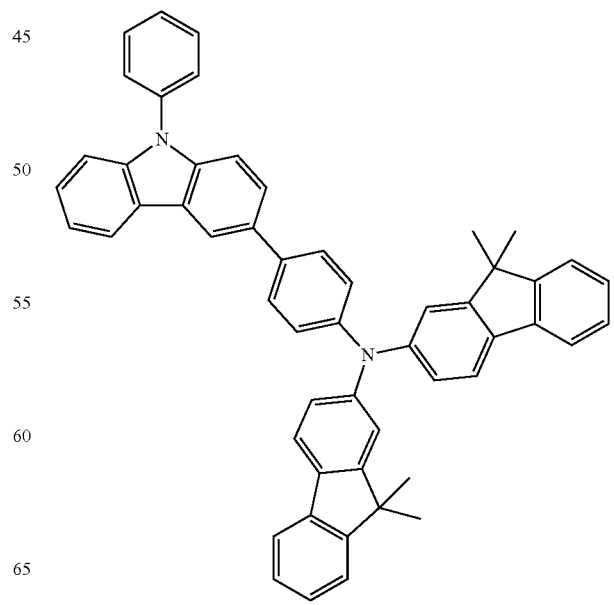

HT8
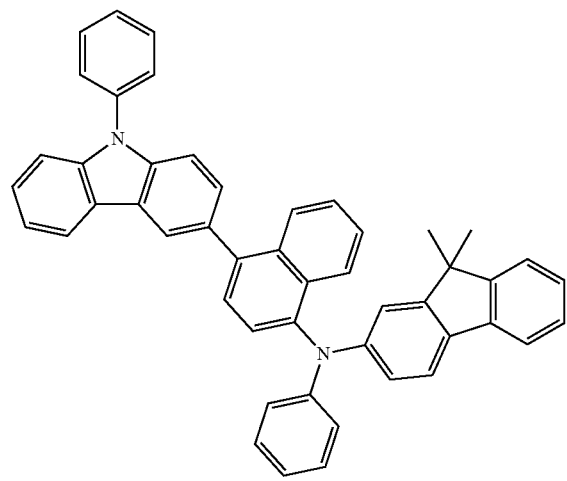
HT9
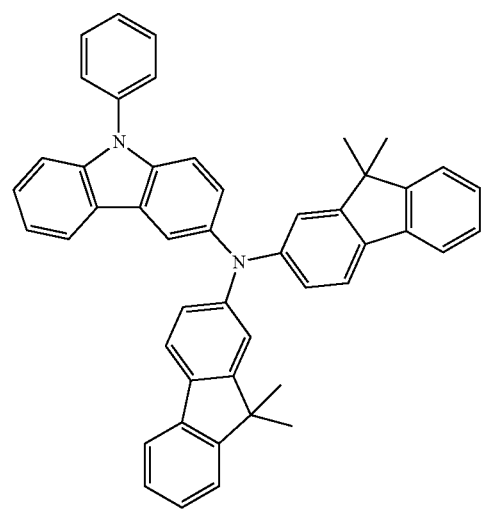
HT10
HT11
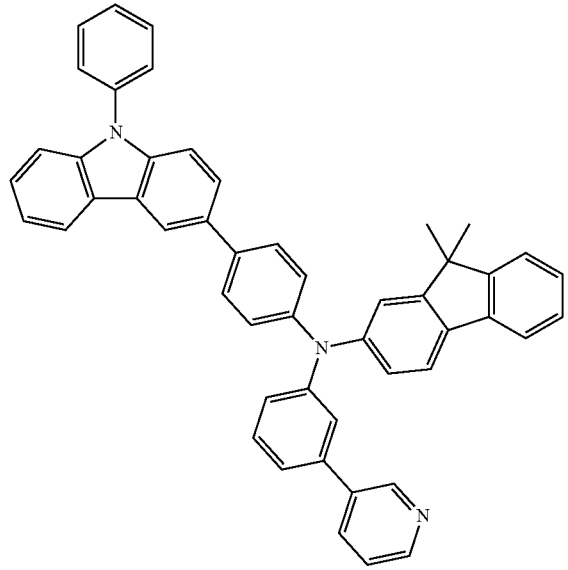
HT12
HT13
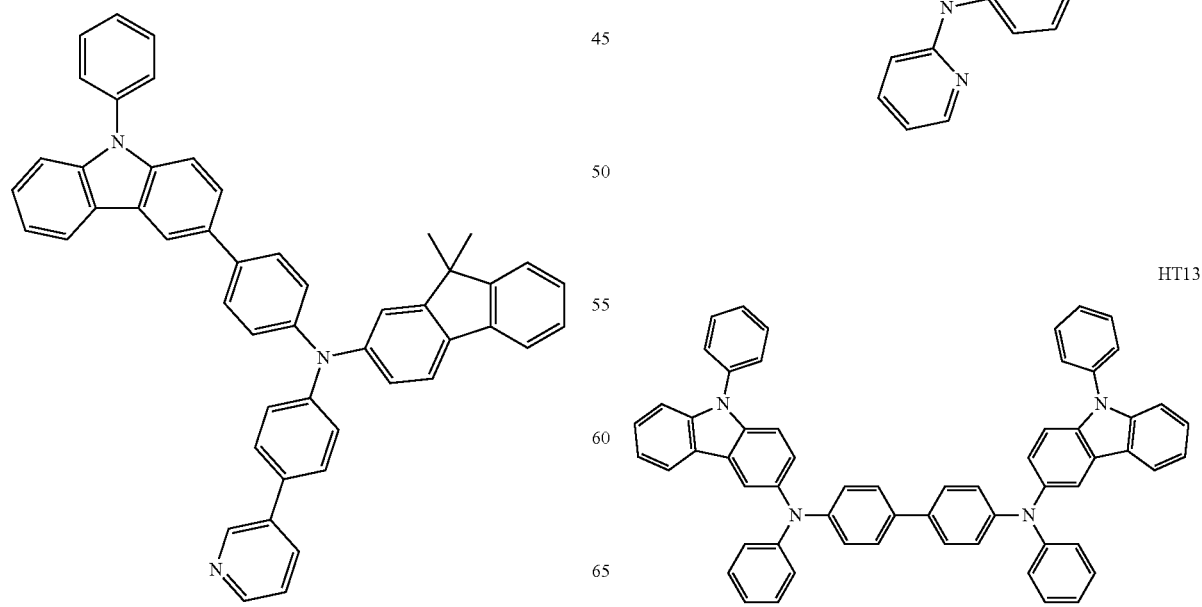

HT14
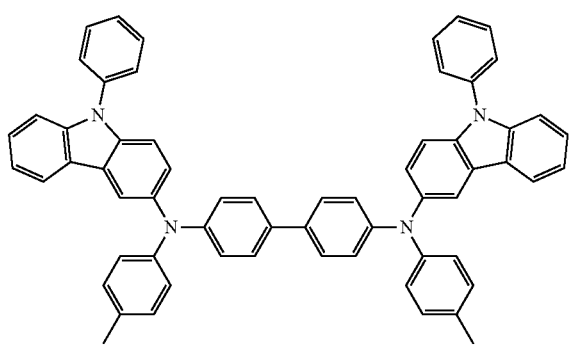

HT15
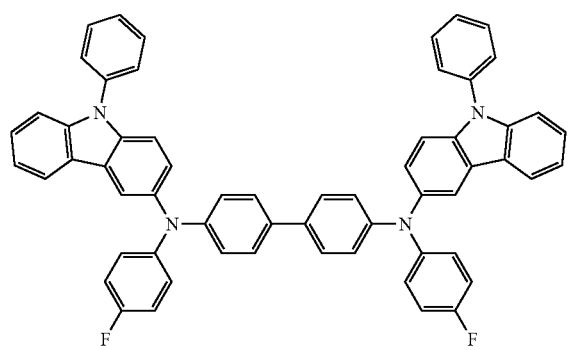

HT16
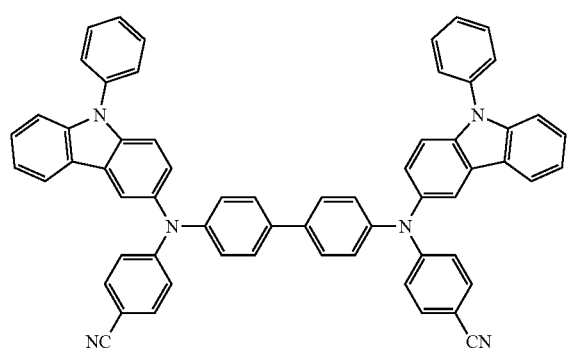

HT17
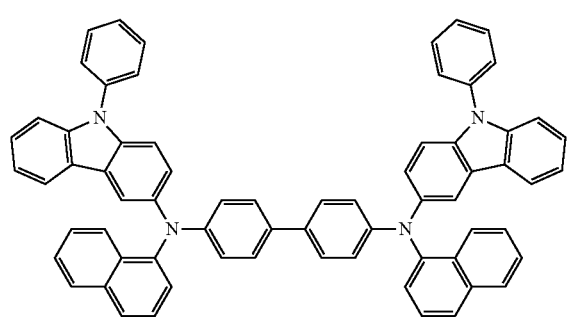

HT18
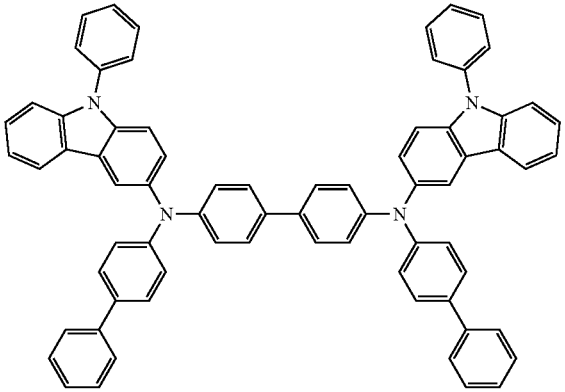

HT19
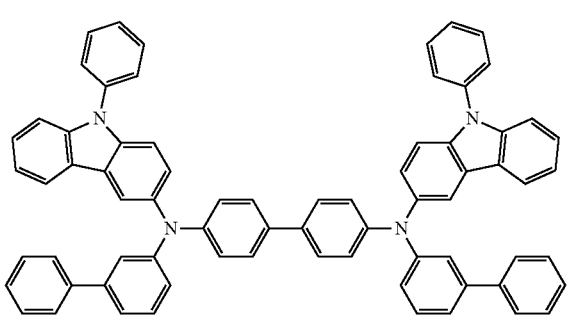

HT20

The thickness of the hole transport region may be from about 100 Angstroms (Å) to about 10,000 Å, and in some embodiments, from about 100 Å to about 1,000 Å. When the hole transport region includes a HIL and a HTL, a thickness of the NIL may be from about 100 Å to about 10,000 Å, and in some embodiments, from about 100 Å to about 1,000 Å, and the thickness of the HTL may be from about 50 Å to about 2,000 Å, and in some embodiments, from about 100 Å to about 1,500 Å. While not wishing to be bound by theory, it is believed that when the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound HT-D1, Compound HT-D2, and the like.

Compound HT-D1

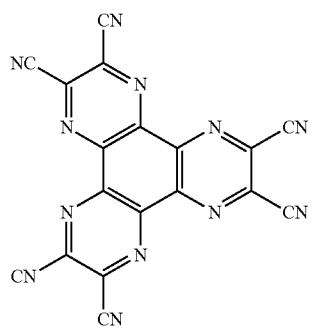

F4-TCNQ

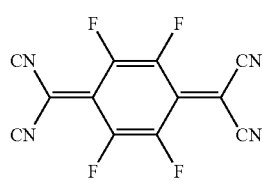

Compound HT-D2

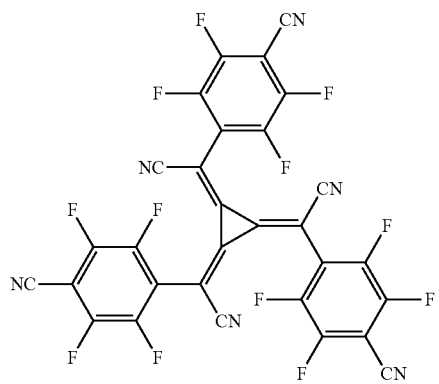

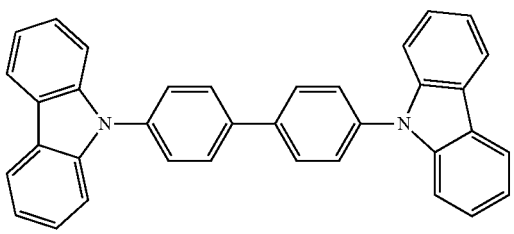

CBP

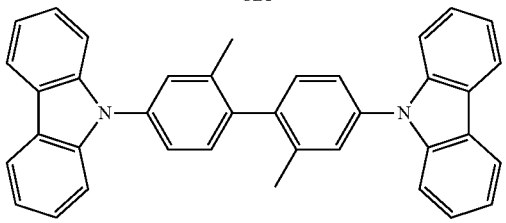

CDBP

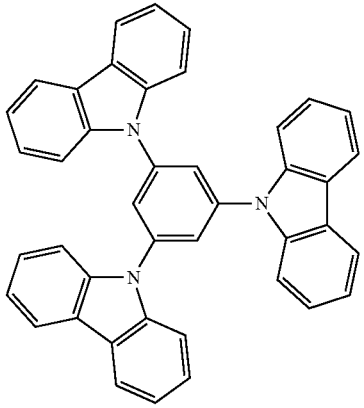

TCP

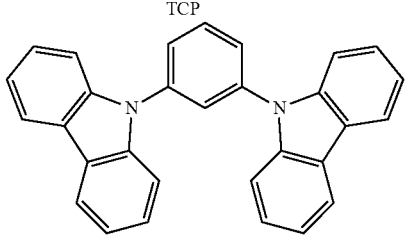

mCP

The hole transport region may further include a buffer layer.

The buffer layer may compensate for an optical resonance distance of light according to a wavelength of the light emitted from the EML, and thus may increase efficiency.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

The EML may include a host and a dopant.

The host may include at least one of CBP, CDBP, TCP, and mCP.

When the organic light-emitting device is a full color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto.

The EML may include the organometallic compound of Formula 1 as a dopant.

When the EML includes both a host and a dopant, the amount of the dopant may be from about 0.01 to about 20 parts by weight based on 100 parts by weight of the host. However, the amount of the dopant is not limited to this range.

The thickness of the EML may be about 100 Å to about 1000 Å, and in some embodiments, may be from about 200

Å to about 600 Å. When the thickness of the EML is within these ranges, the EML may have improved light-emitting ability without a substantial increase in driving voltage.

Next, the electron transport region may be formed on the EML.

The electron transport region may include at least one of a HBL, an ETL, and an EIL.

In some embodiments, the electron transport region may have a structure including a HBL/ETL/EIL, or an ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different materials.

Conditions for forming the HBL, ETL, and EIL of the electron transport region may be the same as those for the NIL described above.

When the electron transport region includes the HBL, the HBL may include at least one of BCP and Bphen. However, embodiments of the present disclosure are not limited thereto.

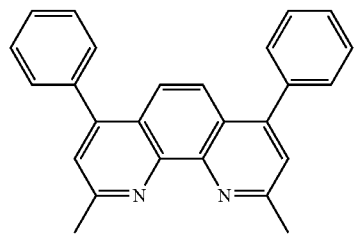

BCP

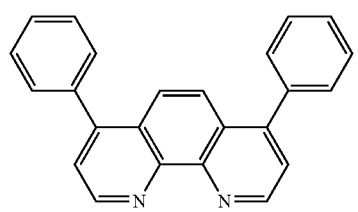

Bphen

The thickness of the HBL may be from about 20 Å to about 1,000 Å, and in some embodiments, from about 30 Å to about 300 Å. While not wishing to be bound by theory, it is believed that when the thickness of the HBL is within these ranges, the HBL may have improved hole blocking ability without a substantial increase in driving voltage.

The ETL may further include at least one of $Alq_3$, Balq, TAZ, and NTAZ, in addition to BCP and Bphen described above.

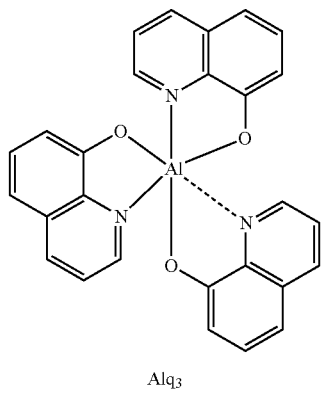

$Alq_3$

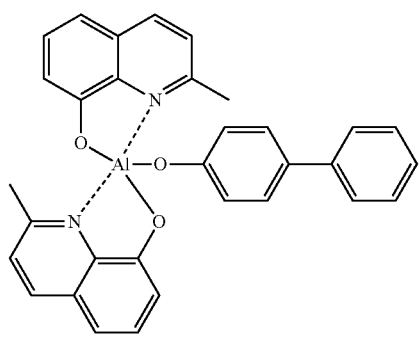

BAlq

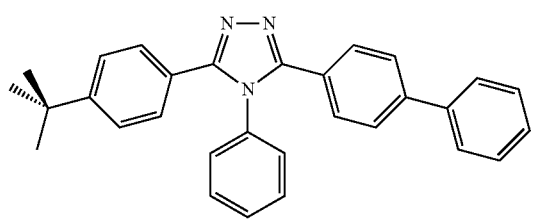

TAZ

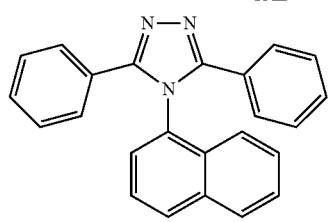

NTAZ

In some embodiments, the ETL may include at least one of Compounds ET1 to ET19, but is not limited thereto.

ET1
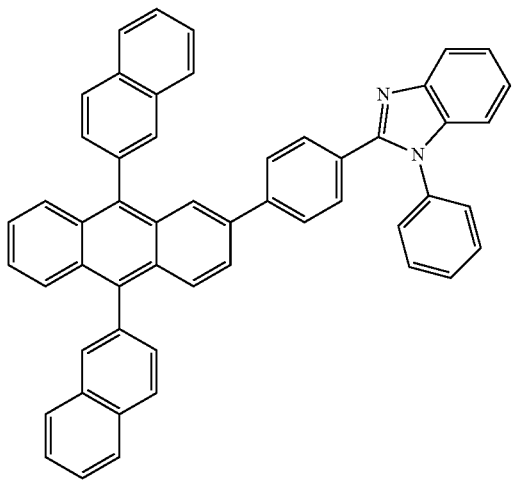
ET4
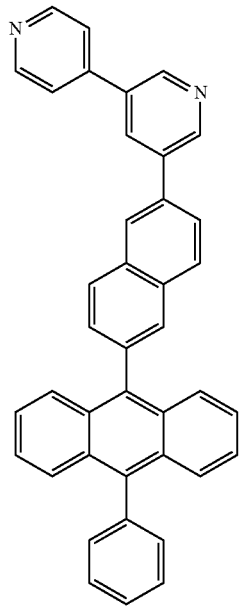
ET2
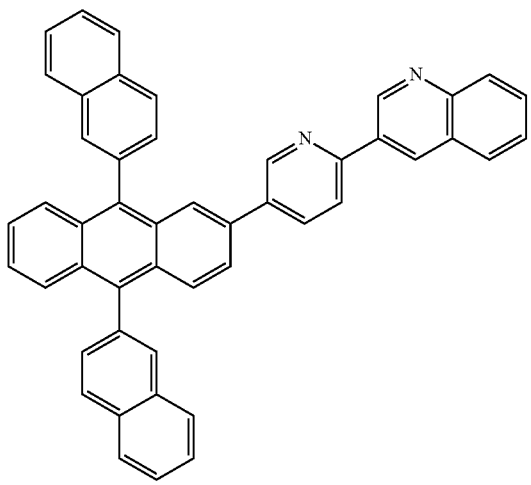
ET5
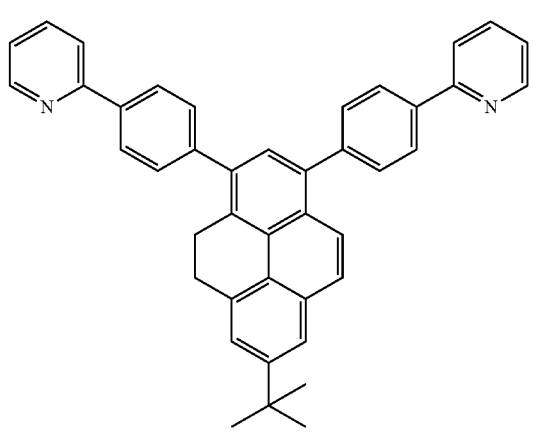
ET3
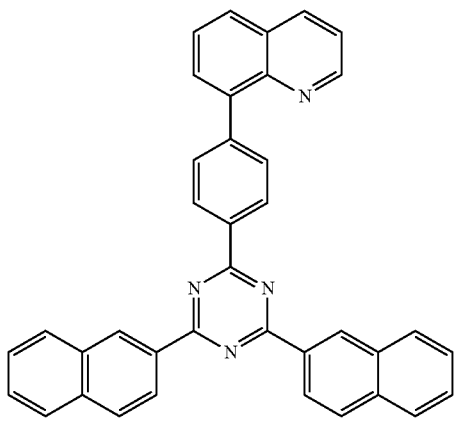
ET6
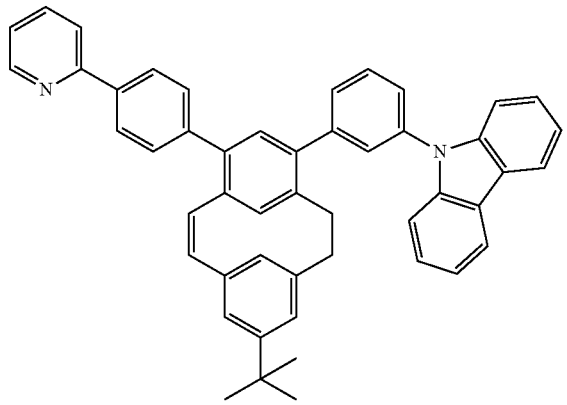

ET7
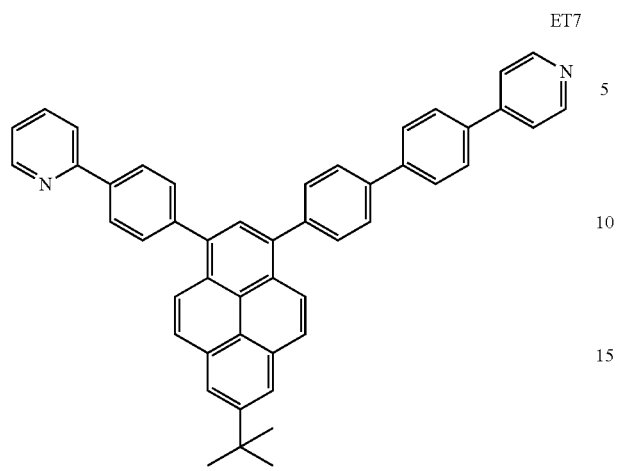
ET10
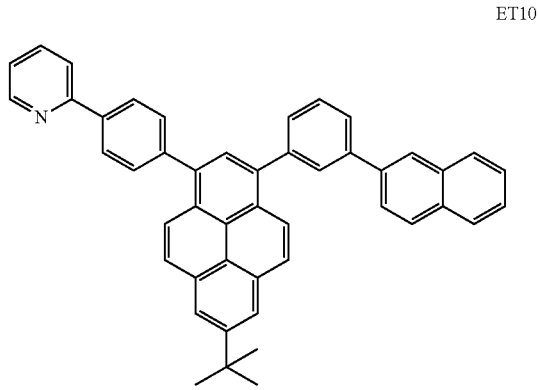
ET11
ET8
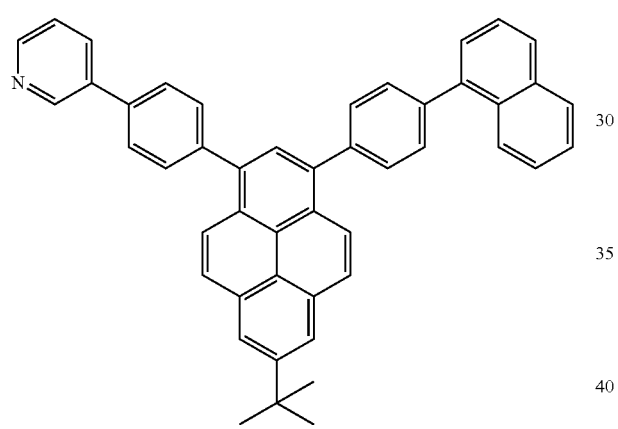
ET12
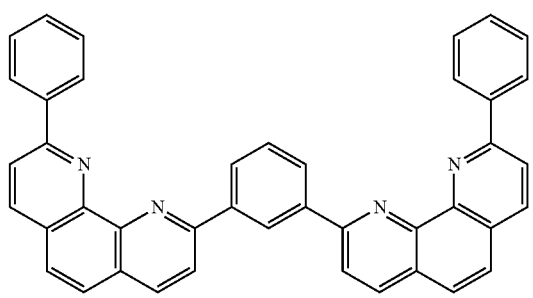
ET13
ET9
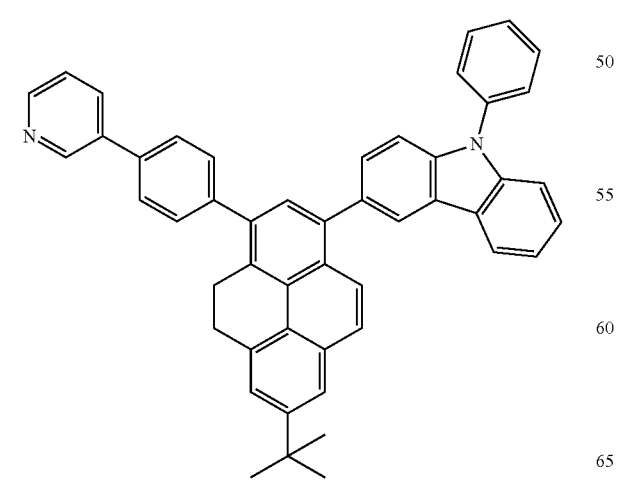
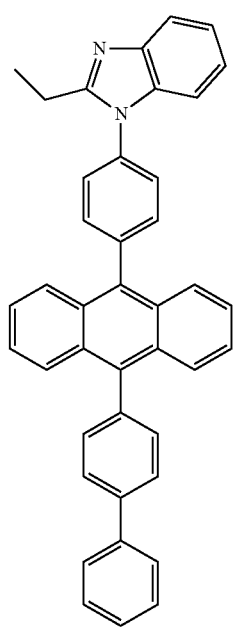

ET14
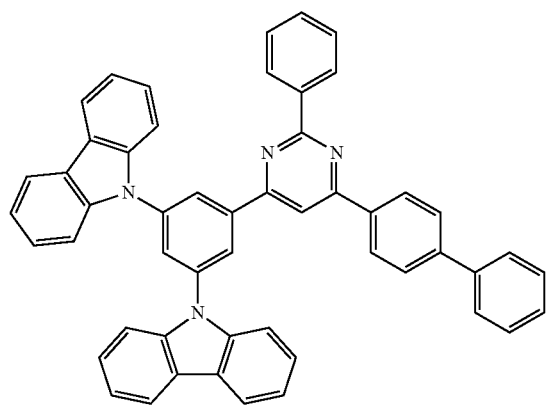
ET17
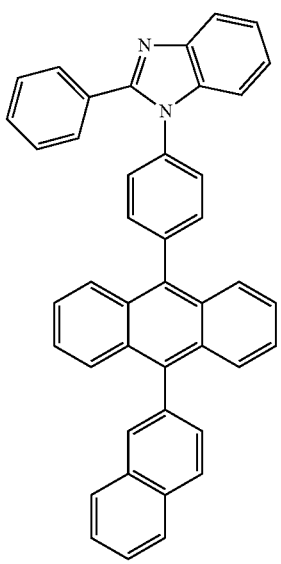
ET15
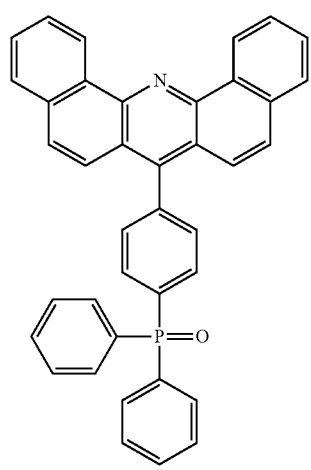
ET18
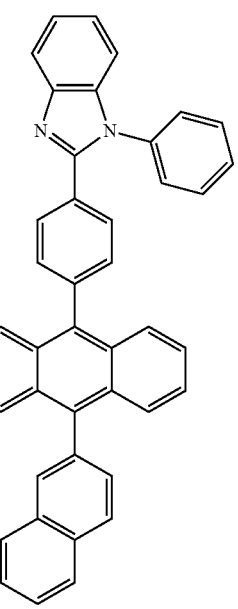
ET16
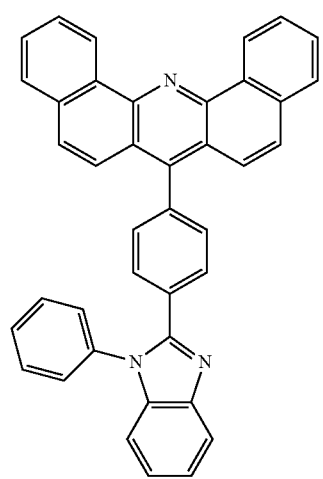
ET19
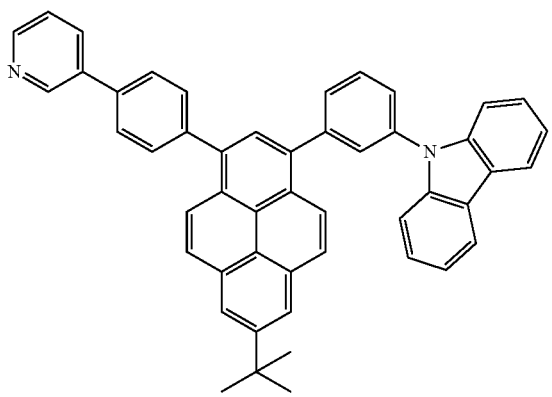
The thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage, In some embodiments the ETL may further include a metal-containing material, in addition to the above-described materials.

The metal-containing material may include a lithium (Li) complex. Non-limiting examples of the Li complex are compound ET-D1 (lithium quinolate (LiQ)), or compound ET-D2.

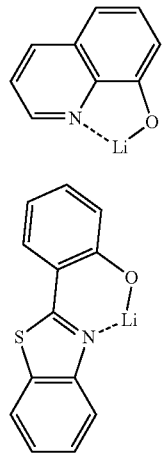

ET-D1

ET-D2

The electron transport region may include an EIL that may facilitate injection of electrons from the second electrode 19. The EIL may include at least one selected from LiF, NaCl, CsF, $Li_2O$, and BaO. The thickness of the EIL may be from about 1 Angstrom (Å) to about 100 Å and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that has a low work function, or a combination thereof. Non-limiting examples of the material for the second electrode 19 are lithium (Li), magnesium (Mg), aluminum (Al), aluminum (Al)-lithium (Li), calcium (Ca), magnesium (Mg)-indium (In), magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device 10 of FIG. 1 is described above, embodiments of the present disclosure are not limited thereto, As used herein, a $C_1$-$C_{30}$ alkyl group refers to a linear or branched aliphatic hydrocarbon monovalent group having 1 to 30 carbon atoms. Non-limiting examples of the $C_1$-$C_{60}$ alkyl group are a methyl group, an ethyl group, a propyl group, an isobutyl group, a sec-butyl group, a tert-butyl group, a pentyl group, an iso-amyl group, and a hexyl group.

As used herein, a $C_1$-$C_{30}$ alkoxy group refers to a monovalent group represented by —$OA_{101}$ (where $A_{101}$ is a $C_1$-$C_{30}$ alkyl group as described above). Non-limiting examples of the $C_1$-$C_{30}$ alkoxy group are a methoxy group, an ethoxy group, and an isopropyloxy group.

As used herein, a $C_2$-$C_{30}$ alkenyl group refers to a structure including at least one carbon double bond in the middle or terminal of the $C_2$-$C_{30}$ alkyl group. Non-limiting examples of the $C_2$-$C_{30}$ alkenyl group are an ethenyl group, a propenyl group, and a butenyl group.

As used herein, a $C_2$-$C_{30}$ alkynyl group refers to a structure including at least one carbon triple bond in the middle or terminal of the $C_2$-$C_{30}$ alkyl group. Non-limiting examples of the $C_2$-$C_{30}$ alkynyl group are an ethynyl group, and a propynyl group.

As used herein, a $C_3$-$C_{10}$ cycloalkyl group refers to a monovalent monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group.

As used herein, a $C_1$-$C_{10}$ heterocycloalkyl group refers to a monovalent monocyclic group having 1 to 10 carbon atoms in which at least one heteroatom selected from N, O, P, and S is included as a ring-forming atom. Non-limiting examples of the $C_1$-$C_{10}$ heterocycloalkyl group are a tetrahydrofuranyl group, and a tetrahydrothiophenyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group.

As used herein, a $C_1$-$C_{10}$ heterocycloalkenyl group used herein refers to a monovalent monocyclic group having 1 to 10 carbon atoms that includes at least one double bond in the ring and in which at least one heteroatom selected from N, O, P, and S is included as a ring-forming atom. Non-limiting examples of the $C_1$-$C_{10}$ heterocycloalkenyl group are a 2,3-dihydrofuranyl group, and a 2,3-dihydrothiophenyl group.

As used herein, a $C_6$-$C_{30}$ aryl group refers to a monovalent, aromatic carbocyclic aromatic group having 6 to 30 carbon atoms. Non-limiting examples of the $C_6$-$C_{30}$ aryl group are a phenyl group, a naphthyl group, an anthracenyl group, a phenanthrenyl group, a pyrenyl group, and a chrysenyl group. When the $C_6$-$C_{60}$ aryl group includes at least two rings, the rings may be fused to each other.

As used herein, a $C_1$-$C_{30}$ heteroaryl group refers to a monovalent, aromatic carbocyclic aromatic group having 1 to 30 carbon atoms in which at least one heteroatom selected from N, O, P, and S is included as a ring-forming atom. Non-limiting examples of the $C_1$-$C_{30}$ heteroaryl group are a pyridinyl group, a pyrimidinyl group, a pyrazinyl group, a pyridazinyl group, a triazinyl group, a quinolinyl group, and an isoquinolinyl group. When a $C_1$-$C_{30}$ heteroaryl group has at least two rings, the rings may be fused to each other.

A $C_6$-$C_{30}$ aryloxy group as used herein indicates —$OA_{102}$ (wherein $A_{102}$ is the $C_6$-$C_{30}$ aryl group), a $C_6$-$C_{30}$ arylthio group as used herein indicates —$SA_{103}$ (wherein $A_{103}$ is the $C_6$-$C_{30}$ aryl group), and a $C_7$-$C_{30}$ arylalkyl group as used herein indicates -$A_{104}A_{105}$ (wherein $A_{104}$ is the $C_6$-$C_{30}$ aryl group and $A_{105}$ is the $C_1$-$C_{30}$ alkyl group).

A $C_2$-$C_{30}$ heteroaryloxy group as used herein indicates —$OA_{106}$ (wherein $A_{106}$ is the $C_2$-$C_{30}$ heteroaryl group), a $C_2$-$C_{30}$ heteroarylthio group as used herein indicates —$SA_{107}$ (wherein $A_{107}$ is the $C_2$-$C_{30}$ heteroaryl group), and a $C_3$-$C_{30}$ heteroarylalkyl group as used herein indicates -$A_{108}A_{109}$ (wherein $A_{108}$ is the $C_2$-$C_{30}$ heteroaryl group and $A_{109}$ is the $C_1$-$C_{30}$ alkyl group).

As used herein, a monovalent non-aromatic condensed polycyclic group refers to a monovalent group having at least two rings condensed to each other, in which only carbon atoms are exclusively included as ring-forming atoms and the entire molecule has non-aromaticity. A non-limiting example of the monovalent non-aromatic condensed polycyclic group is a fluorenyl group.

As used herein, a monovalent non-aromatic condensed heteropolycyclic group refers to a monovalent group having at least two rings condensed to each other, in which carbon atoms and a heteroatom selected from N, O, P, and S are included as ring-forming atoms and the entire molecule has non-aromaticity. A non-limiting example of the monovalent non-aromatic condensed heteropolycyclic group is a carbazolyl group.

As used herein, a $C_1$-$C_{30}$ alkylsilyl group refers to —Si$(A_{102})(A_{103})(A_{104})$ (where $A_{102}$ to $A_{104}$ may be each independently a $C_1$-$C_{30}$ alkyl group as described above).

As used herein, at least one substituent of the substituted $C_1$-$C_{30}$ alkyl group, the substituted $C_3$-$C_{30}$ branched alkyl group, the substituted $C_2$-$C_{30}$ alkenyl group, the substituted $C_2$-$C_{30}$ alkynyl group, the substituted $C_1$-$C_{30}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{30}$ aryl group, the substituted $C_6$-$C_{30}$ aryloxy group, the substituted $C_6$-$C_{30}$ arylthio group, the substituted $C_7$-$C_{30}$ arylalkyl group, the substituted $C_1$-$C_{30}$ heteroaryl group, the substituted $C_2$-$C_{30}$ heteroaryloxy group, the substituted $C_2$-$C_{30}$ heteroarylthio group, the substituted $C_3$-$C_{30}$ heteroarylalkyl group, the substituted monovalent non-aromatic condensed polycyclic group, the substituted monovalent non-aromatic condensed heteropolycyclic group, and the substituted $C_1$-$C_{30}$ alkylsilyl group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group, a $C_1$-$C_{60}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, —N$(Q_{11})(Q_{12})$, —Si$(Q_{13})(Q_{14})(Q_{15})$, and —B$(Q_{16})(Q_{17})$, a $C_3$-$C_{10}$ cycloalkyl group, a $C_1$-$C_{10}$ heterocycloalkyl group, a $C_{3-10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, and a monovalent non-aromatic condensed heteropolycyclic group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, —N$(Q_{21})(Q_{22})$, —Si$(Q_{23})(Q_{24})(Q_{25})$ and —B$(Q_{26})(Q_{27})$, and —N$(Q_{31})(Q_{32})$, —Si$(Q_{33})(Q_{34})(Q_{35})$, and —B$(Q_{36})(Q_{37})$.

In some embodiments, $Q_{11}$ to $Q_{17}$ and $Q_{31}$ to $Q_{37}$ herein may be each independently selected from a hydrogen, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, and a monovalent non-aromatic condensed heteropolycyclic group.

For example, at least one substituent of the substituted $C_1$-$C_{60}$ alkylene group, the substituted $C_2$-$C_{30}$ alkenylene group, the substituted $C_2$-$C_{30}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{30}$ arylene group, the substituted $C_1$-$C_{30}$ heteroarylene group, the substituted divalent non-aromatic condensed polycyclic group, the substituted divalent non-aromatic condensed heteropolycyclic group, the substituted $C_1$-$C_{30}$ alkyl group, the substituted $C_2$-$C_{30}$ alkenyl group, the substituted $C_2$-$C_{30}$ alkynyl group, the substituted $C_3$-$C_{10}$ cycloalkyl group, the substituted $C_1$-$C_{10}$ heterocycloalkyl group, the substituted $C_3$-$C_{11}$ cycloalkenyl group, the substituted $C_1$-$C_{10}$ heterocycloalkenyl group, the substituted $C_6$-$C_{30}$ aryl group, the substituted $C_6$-$C_{30}$ aryloxy group, the substituted $C_6$-$C_{30}$ arylthio group, the substituted $C_7$-$C_{30}$ arylalkyl group, the substituted $C_1$-$C_{30}$ heteroaryl group, the substituted $C_2$-$C_{30}$ heteroaryloxy group, the substituted $C_2$-$C_{30}$ heteroarylthio group, the substituted $C_3$-$C_{30}$ heteroarylalkyl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group, a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_3$© heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group that are each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group, a $C_3$-$C_{10}$ cycloalkyl group, a $C_1$-$C_{11}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$, wherein $Q_{11}$ to $Q_{17}$ and $Q_{31}$ to $Q_{37}$ may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a hydrogen, a $C_1$-$C_{30}$ alkyl group, a $C_2$-$C_{30}$ alkenyl group, a $C_2$-$C_{30}$ alkynyl group, a $C_1$-$C_{30}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group. However, embodiments are not limited thereto.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{10}$ alkyl" refers to a $C_1$-$C_{30}$ alkyl group substituted with $C_6$-$C_{60}$ aryl group, the total number of carbon atoms in the resulting aryl substituted alkyl group is $C_7$-$C_{90}$.

Hereinafter, the present inventive concept will be described in detail with reference to the following synthesis examples and other examples of compounds and organic light-emitting devices. However, these examples are for illustrative purposes only and are not intended to limit the scope of the present inventive concept. In the following synthesis examples, the expression that "'B' instead of 'A' was used" means that the amounts of 'B' and 'A' were the same in equivalent amounts.

EXAMPLES

Synthesis Example 1

Synthesis of Compound 1

Reaction Scheme 1

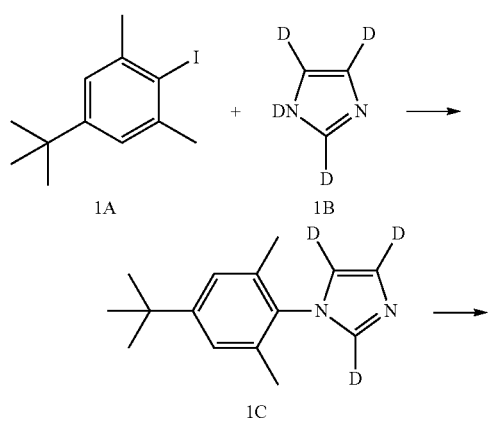

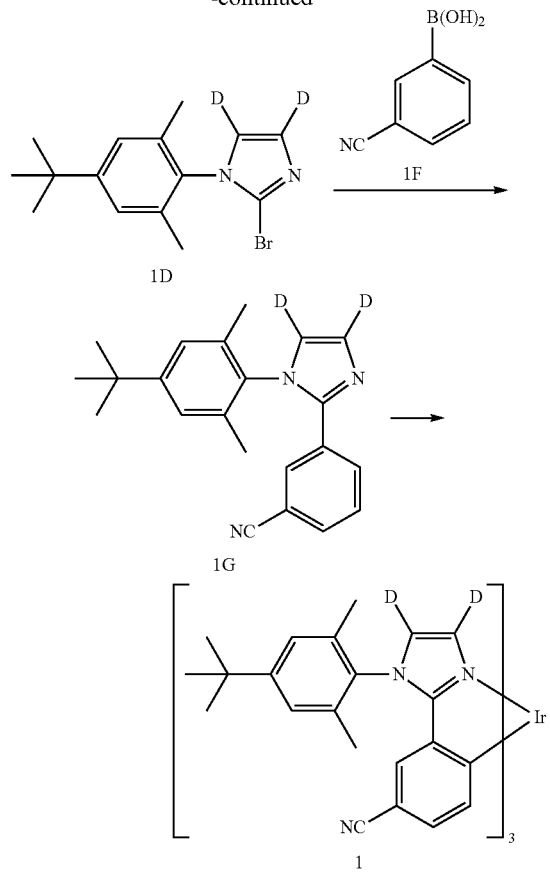

(1) Synthesis of Intermediate 37C 34.70 millimoles (mmol) of Compound 37A, 41.64 mmol of Compound B, mmol of $K_2CO_3$, 1.74 mmol of CuI, 3.47 mmol of 1,10-phenanthroline, and 500 milliliters (mL) of dimethylformamide (DMF) were placed into a 1 liter (L)-reaction container, and refluxed under a nitrogen atmosphere for about 12 hours. After the reaction finished, the resulting reaction product was cooled down to room temperature, dichloromethane and distilled water were added thereto, and the organic phase was separated therefrom. After the separated organic phase was washed with distilled water twice and dried using $MgSO_4$, the solvent was removed to obtain a crude product. The crude product was purified by silica gel column chromatography (using ethyl acetate and n-hexane as an eluent) to thereby obtain 26.37 mmol of Intermediate 37C. This intermediate 37C was identified by liquid chromatography-mass spectroscopy (LC-MS).

LC-MS (m/z): 232.47 [M+1]

(2) Synthesis of Intermediate 37D 26.37 mmol of Compound 37C and tetrahydrofuran (THF) were placed into a reaction container, and cooled to about −78° C. under a nitrogen atmosphere. 27.69 mmol of 2.5 molar (M) n-BuLi (in n-hexane) was slowly added thereto at the same temperature and stirred for about 1 hour, and 52.74 mmol of $Br_2$ was slowly added thereto at the same temperature. After 30 minutes, the cooling by the cooler was stopped to allow a natural temperature to rise to room temperature, at which the resulting product was then stirred for about 6 hours. After the reaction finished, dichloromethane and distilled water were added thereto, and the organic phase was separated therefrom. After the separated organic phase was washed with distilled water twice and dried using MgSO$_4$, the solvent was removed to obtain a crude product. The crude product was purified by silica gel column chromatography (using ethyl acetate and n-hexane as an eluent) to thereby obtain 18.72 mmol of Intermediate 37D. This intermediate 37D was identified by LC-MS.

LC-MS (m/z): 310.18 [M+1]

(3) Synthesis of Intermediate LM037

18.72 mmol of Compound 37D, 28.08 mmol of Compound 1E, 1.87 mmol of Pd(PPh$_3$)$_4$, 210.63 mmol of K$_2$CO$_3$, and a mixture of THF and distilled water (2:1) were placed into a reaction container and refluxed under a nitrogen atmosphere for about 12 hours. After the reaction finished, the resulting reaction product was cooled down to room temperature, dichloromethane and distilled water were added thereto, and the organic phase was separated therefrom. After the separated organic phase was washed with distilled water twice and dried using MgSO$_4$, the solvent was removed to obtain a crude product. The crude product was purified by silica gel column chromatography (using ethyl acetate and n-hexane as an eluent) to thereby obtain 16.47 mmol of Intermediate LM037. This intermediate LM037 was identified by LC-MS.

LC-MS (m/z): 332.58 [M+1]

(4) Synthesis of Compound BD037

3.29 mmol of Ir(acac)$_3$, 16.47 mmol of Compound LM037, and glycerol were placed into a reaction container together and refluxed under a nitrogen atmosphere for about 12 hours. After the reaction finished, the resulting reaction product was cooled down to room temperature, dichloromethane and distilled water were added thereto, and the organic phase was separated therefrom. After the separated organic phase was washed with distilled water twice and dried using MgSO$_4$, the solvent was removed to obtain a crude product. The crude product was purified by silica gel column chromatography (using ethyl acetate and n-hexane as an eluent) to thereby obtain 0.49 mmol of Compound BD037. This Compound BD037 was identified by matrix assisted laser desorption/ionization time-of-flight mass spectrometry (MALDI-TOF MS)

MALDI-TOF(m/z): 1183.57 [M]+

Synthesis Example 2

Synthesis of Compound BD040

Compound BD040 was synthesized in the same manner as in Reaction Scheme 1, except that Intermediate 40A represented by a formula below, instead of Compound 37A used in the synthesis of Compound BD037 according to Reaction Scheme 1, was used.

MALDI-TOF(m/z): 1201.66 [M]+

Synthesis Example 3

Synthesis of Compound BD044

Compound BD044 was synthesized in the same manner as in Reaction Scheme 1, except that Intermediates 44A and 2E represented by formulae below, instead of Compounds 37A and 1E used in the synthesis of Compound BD037 according to Reaction Scheme 1, were used. This Compound BD044 was identified by MALDI-TOF.

MALDI-TOF(m/z): 1216.71 [M]+

Synthesis Example 4

Synthesis of Compound BD045

Compound BD045 was synthesized in the same manner as in Reaction Scheme 1, except that Intermediates 45A and 2E represented by formulae below, instead of Compounds 37A and 1E used in the synthesis of Compound BD037 according to Reaction Scheme 1, were used. This Compound BD045 was identified by MALDI-TOF.

MALDI-TOF(m/z): 1243.88 [M]+

Synthesis Example 5

Synthesis of Compound BD047

Compound BD047 was synthesized in the same manner as in Reaction Scheme 1, except that Intermediates 45A and 3E represented by formulae below, instead of Compounds 37A and 1E used in the synthesis of Compound BD037 according to Reaction Scheme 1, were used. This Compound BD047 was identified by MALDI-TOF.

MALDI-TOF(m/z): 1292.05 [M]+

Synthesis Example 6

Synthesis of Compound BD049

Compound BD049 was synthesized in the same manner as in Reaction Scheme 1, except that Intermediates 45A and 4E represented by formulae below, instead of Compounds 37A and 1E used in the synthesis of Compound BD037 according to Reaction Scheme 1, were used. This Compound BD049 was identified by MALDI-TOF.

MALDI-TOF(m/z): 1436.22 [M]+

Synthesis Example 7

Synthesis of Compound BD064

Compound BD064 was synthesized in the same manner as in Reaction Scheme 1, except that Intermediates 64A and 2E represented by formulae below, instead of Compounds 37A and 1E used in the synthesis of Compound BD037 according to Reaction Scheme 1, were used. This Compound BD046 was identified by MALDI-TOF.

MALDI-TOF(m/z): 1446.28 [M]+

Synthesis Example 8

Synthesis of Compound BD079

Compound BD079 was synthesized in the same manner as in Reaction Scheme 1, except that Intermediates 79A and 2E represented by formulae below, instead of Compounds 37A and 1E used in the synthesis of Compound BD037 according to Reaction Scheme 1, were used. This Compound BD079 was identified by MALDI-TOF.

MALDI-TOF(m/z): 1292.01 [M]+

Synthesis Example 9

Synthesis of Compound BD079

Compound BD098 was synthesized in the same manner as in Reaction Scheme 1, except that Intermediates 98A and 2E represented by formulae below, instead of Compounds 37A and 1E used in the synthesis of Compound BD037 according to Reaction Scheme 1, were used. This Compound BD079 was identified by MALDI-TOF.

MALDI-TOF(m/z): 1484.26 [M]+

Synthesis Example 10

Synthesis of Compound BD113

Compound BD113 was synthesized in the same manner as in Reaction Scheme 1, except that Intermediates 113A and 2E represented by formulae below, instead of Compounds 37A and 1E used in the synthesis of Compound BD037 according to Reaction Scheme 1, were used. This Compound BD113 was identified by MALDI-TOF.

MALDI-TOF(m/z): 1291.82 [M]+

Synthesis Example 11

Synthesis of Compound BD132

Compound BD132 was synthesized in the same manner as in Reaction Scheme 1, except that Intermediates 132A and 2E represented by formulae below, instead of Compounds 37A and 1E used in the synthesis of Compound BD132 according to Reaction Scheme 1, were used. This Compound BD132 was identified by MALDI-TOF.

MALDI-TOF(m/z): 1484.11 [M]+

Synthesis Example 12

Synthesis of Compound BD151

Compound BD151 was synthesized in the same manner as in Reaction Scheme 1, except that Intermediates 151A and 2E represented by formulae below, instead of Compounds 37A and 1E used in the synthesis of Compound BD037 according to Reaction Scheme 1, were used. This Compound BD151 was identified by MALDI-TOF.

MALDI-TOF(m/z): 1291.61 [M]+

Synthesis Example 13

Synthesis of Compound BD180

Compound BD180 was synthesized in the same manner as in Reaction Scheme 1, except that Intermediates 180A and 2E represented by formulae below, instead of Compounds 37A and 1E used in the synthesis of Compound BD037 according to Reaction Scheme 1, were used. This Compound BD180 was identified by MALDI-TOF.

MALDI-TOF(m/z): 1484.05 [M]+

Synthesis Example 14

Synthesis of Compound BD201

Compound BD201 was synthesized in the same manner as in Reaction Scheme 1 except that Intermediates 201A and 2E represented by formulae below, instead of Compounds 37A and 1E used in the synthesis of Compound BD037 according to Reaction Scheme 1, were used. This Compound BD201 was identified by MALDI-TOF.

MALDI-TOF(m/z): 1291.65 [M]+

Synthesis Example 15

Synthesis of Compound BD233

Compound BD233 was synthesized in the same manner as in Reaction Scheme 1 except that Intermediates 233A and 2E represented by formulae below, instead of Compounds 37A and 1E used in the synthesis of Compound BD037 according to Reaction Scheme 1, were used. This Compound BD233 was identified by MALDI-TOF.

MALDI-TOF(m/z): 1484.05 [M]+

Synthesis Example 16

Synthesis of Compound BD248

Compound BD248 was synthesized in the same manner as in Reaction Scheme 1 except that Intermediates 248A and 2E represented by formulae below, instead of Compounds 37A and 1E used in the synthesis of Compound BD037 according to Reaction Scheme 1, were used. This Compound BD248 was identified by MALDI-TOF.

MALDI-TOF(m/z): 1519.95 [M]+

Synthesis Example 17

Synthesis of Compound BD255

Compound BD255 was synthesized in the same manner as in Reaction Scheme 1, except that Intermediates 255A and 2E represented by formulae below, instead of Compounds 37A and 1E used in the synthesis of Compound BD037 according to Reaction Scheme 1, were used. This Compound BD255 was identified by MALDI-TOF.

MALDI-TOF(m/z): 1519.93 [M]+

Formulae of Intermediates

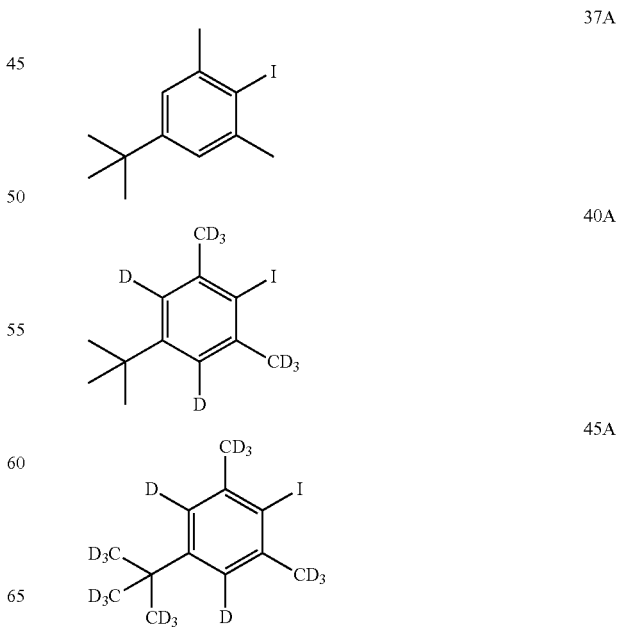

119
-continued
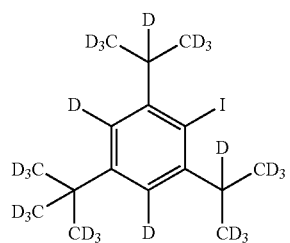
64A
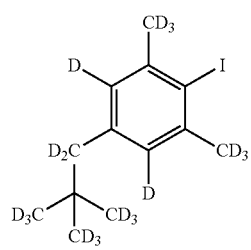
79A
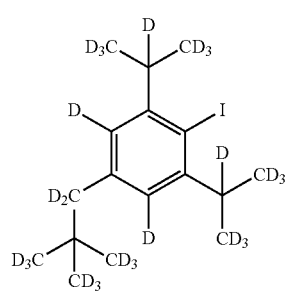
98A
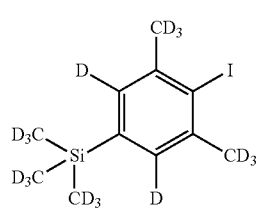
113A
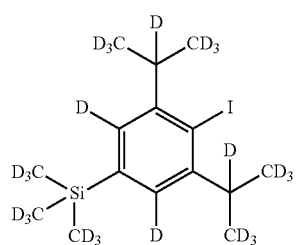
132A
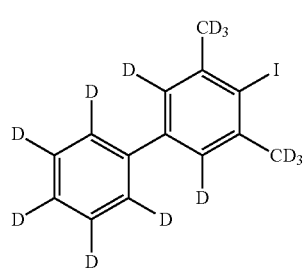
151A
120
-continued
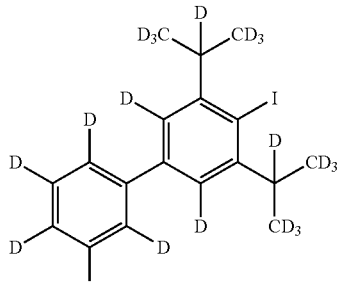
180A
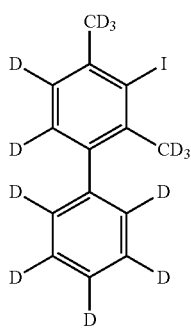
201A
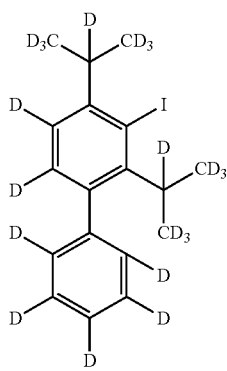
233A
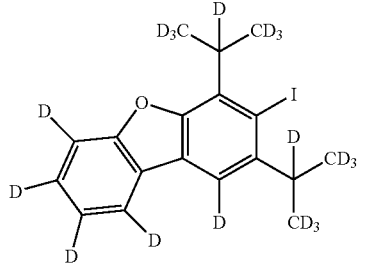
248A

255A

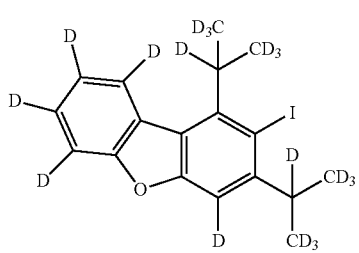

1E

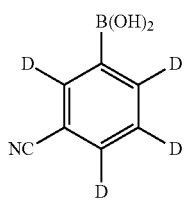

2E

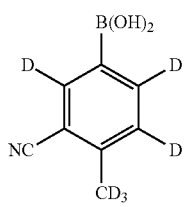

3E

4E

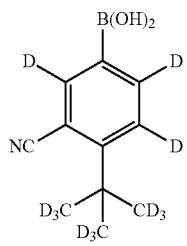

Evaluation Example 1

Evaluation on HOMO, LUMO, and Triplet (T1) Energy Levels

Highest occupied molecular orbital (HOMO), lowest unoccupied molecular orbital (LUMO), triplet (T1) energy levels, and $\lambda_{max}$ of Compounds BD037, BD040, BD044, BD045, BD047, BD049, BD064, BD079, BD098, BD113, BD132, BD151, BD180, BD201, BD233, BD248, BD255, and A were evaluated according to the methods described in Table 7. The results are shown in Table 8,

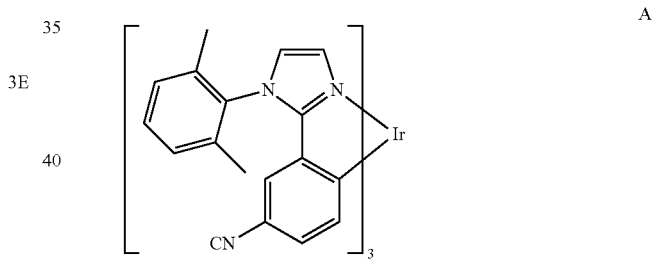

A

TABLE 7

| | |
|---|---|
| HOMO energy level evaluation method | A potential (V)-current (A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)). Then, from reduction onset of the graph, a HOMO energy level of a compound was calculated. |
| LUMO energy level evaluation method | Each compound was diluted at a concentration of $1 \times 10^{-5}$M in CHCl$_3$, and a UV absorption spectrum thereof was measured at room temperature by using a Shimadzu UV-350 spectrometer. Then a LUMO energy level thereof was calculated by using an optical band gap (Eg) from an edge of the absorption spectrum. |
| T1 energy level and $\lambda_{max}$ evaluation method | Each compound was diluted with CH$_2$Cl$_2$ to a concentration 10 millimolar (mM), and loaded into a ISC PC1 spectrofluorometer equipped with a xenon lamp to measure a photoluminescence (PL) spectrum at room temperature. The obtained maximum absorption peak ($\lambda_{max}$) was converted to energy in electron volts (eV). |

TABLE 8

| Compound | HOMO (eV) | LUMO (eV) | T1 (eV) | $\lambda_{max}$ (nm) |
|---|---|---|---|---|
| A | −5.35 | −2.43 | 2.68 | 461 |
| BD037 | −5.32 | −2.41 | 2.68 | 461 |
| BD040 | −5.32 | −2.41 | 2.68 | 461 |
| BD044 | −5.32 | −2.41 | 2.68 | 461 |
| BD045 | −5.32 | −2.41 | 2.68 | 461 |
| BD047 | −5.21 | −2.24 | 2.72 | 456 |
| BD049 | −5.23 | −2.25 | 2.72 | 456 |
| BD064 | −5.31 | −2.41 | 2.68 | 461 |
| BD079 | −5.32 | −2.40 | 2.68 | 461 |
| BD098 | −5.32 | −2.40 | 2.68 | 461 |
| BD113 | −5.29 | −2.38 | 2.68 | 461 |
| BD132 | −5.29 | −2.38 | 2.68 | 461 |
| BD151 | −5.29 | −2.44 | 2.67 | 463 |
| BD180 | −5.29 | −2.43 | 2.68 | 462 |
| BD201 | −5.30 | −2.36 | 2.67 | 463 |
| BD233 | −5.31 | −2.37 | 2.68 | 462 |
| BD248 | −5.26 | −2.18 | 2.68 | 461 |
| BD255 | −5.28 | −2.22 | 2.68 | 461 |

Referring to Table 8, compounds BD037, BD040; BD044, BD045, BD047, BD049, BD064, BD079, BD098, BD113, BD132, BD151, BD180, BD201, BD233, BD248, and BD255 were found to have suitable electric characteristics for use as materials for organic light-emitting devices.

Evaluation Example 2

Purity Analysis of Compound after Deposition as Thin Film

Each of compounds BD037, BD040, BD044, BD045, BD047, BD049, BD064, BD079, BD098, BD113, BD132, BD151, BD180, BD201, BD233, BD248, BD255, and A was vacuum-deposited to form a thin film. Purities of the compounds before and after the vacuum deposition were analyzed by high-performance liquid chromatography (HPLC). The results are shown in Table 9.

TABLE 9

| Compound | Before vacuum deposition (%) | After vacuum deposition (%) | Purity difference between before and after vacuum deposition (%) |
|---|---|---|---|
| BD037 | 98.57 | 97.70 | −0.87 |
| BD040 | 98.45 | 97.65 | −0.80 |
| BD044 | 99.05 | 98.36 | −0.69 |
| BD045 | 99.53 | 98.91 | −0.62 |
| BD047 | 99.28 | 98.06 | −1.22 |
| BD049 | 99.51 | 98.53 | −0.98 |
| BD064 | 99.68 | 99.50 | −0.18 |
| BD079 | 99.42 | 98.71 | −0.71 |
| BD098 | 99.35 | 99.01 | −0.34 |
| BD113 | 99.23 | 98.64 | −0.59 |
| BD132 | 99.42 | 99.06 | −0.36 |
| BD151 | 99.75 | 99.04 | −0.71 |
| BD180 | 99.88 | 99.47 | −0.41 |
| BD201 | 99.70 | 99.05 | −0.65 |
| BD233 | 99.73 | 99.35 | −0.38 |
| BD248 | 99.35 | 98.66 | −0.69 |
| BD255 | 99.43 | 98.87 | −0.56 |
| A | 99.57 | 95.75 | −3.82 |

Referring to Table 9, compounds BD037, BD040, BD044, BD045, BD047, BD049, BD064, BD079, BD098, BD113, BD132, BD151, BD180, BD201, BD233, BD248, and BD255 were found to have less purity difference between before and after vacuum deposition, compared to Compound A. Based on the results in Table 9, the organometallic compound of Formula 1 is found to have good thermal stability due to the substitution with deuterium.

Example 1

A glass substrate with a 1,500 Angstrom (Å)-thick indium tin oxide (ITO) electrode (first electrode, anode) thereon was ultrasonically washed with distilled water and then with isopropyl alcohol, acetone, and methanol. After being dried, the glass substrate was cleaned using oxygen plasma in a plasma-cleaning system for about 5 minutes, and then mounted into a vacuum deposition device.

Compound HT3 was vacuum-deposited on the ITO anode of the glass substrate to form a first hole injection layer (HIL) having a thickness of 3,500 Å, and Compound HT-D1 was vacuum-deposited on the first HIL to form a second HIL having a thickness of about 300 Å. Subsequently, TAPC was vacuum-deposited on the second HIL to form an electron blocking layer (EBL) having a thickness of about 100 Å, thereby forming a hole transport region.

Next, mCP (as a host) and Compound BD037 (as a dopant, 7 percent by weight (wt %)) were co-deposited on the hole transport region to form an emission layer (EML) having a thickness of about 300 Å.

After Compound ET3 was vacuum-deposited on the EML to form an electron transport layer (ETL) having a thickness of about 250 Å, ET-D1 was deposited on the ETL to form an electron injection layer (EIL) having a thickness of about 5 Å, followed by forming an electron transport region.

An aluminum (Al) second electrode (cathode) having a thickness of about 1,000 Å was then formed on the electron transport region thereby manufacturing an organic light-emitting device.

Example 2

An organic light-emitting device was manufactured in the same manner as in Example 1, except that Compound BD040, instead of Compound BD037, was used as a dopant in forming the EML.

Example 3

An organic light-emitting device was manufactured in the same manner as in Example 1 except that Compound BD044, instead of Compound BD037, was used as a dopant in forming the EML.

Example 4

An organic light-emitting device was manufactured in the same manner as in Example 1, except that Compound BD045, instead of Compound BD037, was used as a dopant in forming the EML.

Example 5

An organic light-emitting device was manufactured in the same manner as in Example 1 except that Compound BD047, instead of Compound BD037, was used as a dopant in forming the EML.

Example 6

An organic light-emitting device was manufactured in the same manner as in Example 1, except that Compound BD049, instead of Compound BD037, was used as a dopant in forming the EML.

Example 7

An organic light-emitting device was manufactured in the same manner as in Example 1, except that Compound BD064, instead of Compound BD037, was used as a dopant in forming the EML.

Example 8

An organic light-emitting device was manufactured in the same manner as in Example 1 except that Compound BD079, instead of Compound BD037, was used as a dopant in forming the EML.

Example 9

An organic light-emitting device was manufactured in the same manner as in Example 1, except that Compound BD098, instead of Compound BD037, was used as a dopant in forming the EML.

Example 10

An organic light-emitting device was manufactured in the same manner as in Example 1, except that Compound BD113, instead of Compound BD037, was used as a dopant in forming the EML.

Example 11

An organic light-emitting device was manufactured in the same manner as in Example 1, except that Compound BD132, instead of Compound BD037, was used as a dopant in forming the EML.

Example 12

An organic light-emitting device was manufactured in the same manner as in Example 1, except that Compound BD151, instead of Compound BD037, was used as a dopant in forming the EML.

Example 1

An organic light-emitting device was manufactured in the same manner as in Example 1, except that Compound BD180, instead of Compound BD037, was used as a dopant in forming the EML.

Example 14

An organic light-emitting device was manufactured in the same manner as in Example 1, except that Compound BD201, instead of Compound BD037, was used as a dopant in forming the EML.

Example 15

An organic light-emitting device was manufactured in the same manner as in Example 1, except that Compound BD233, instead of Compound BD037, was used as a dopant in forming the EML.

Example 16

An organic light-emitting device was manufactured in the same manner as in Example 1 except that Compound BD248, instead of Compound BD037, was used as a dopant in forming the EML.

Example 17

An organic light-emitting device was manufactured in the same manner as in Example 1, except that Compound BD255, instead of Compound BD037, was used as a dopant in forming the EML.

Comparative Example 1

An organic light-emitting device was manufactured in the same manner as in Example 1, except that Compound A, instead of Compound BD037, was used as a dopant in forming the EML.

Evaluation Example 3

Evaluation of Characteristics of Organic Light-Emitting Devices

Current density values, luminance values, efficiency values, lifespan values and color coordinates of the organic light-emitting devices of Examples 1 to 17 and Comparative Example 1 were evaluated using the following methods. The results are shown in Table 10.

(1) Measurement of Current Density Changes with Respect to Voltage

While increasing a voltage applied to each of the organic light-emitting devices from 0 volts (V) to about 10 V, a current flowing through each organic light-emitting device was measured using a current voltmeter (Keithley 2400), followed by dividing the current value by the area of the organic light-emitting device to obtain a current density.

(2) Measurement of Luminance Changes with Respect to Voltage

While increasing a voltage applied to each of the organic light-emitting devices from about 0 V to about 10 V, luminances of the organic light-emitting devices were measured using a luminance meter (Minolta Cs-1000A).

(3) Measurement of Current Efficiencies

Current efficiencies (candelas per ampere, cd/A) of the organic light-emitting devices at the same current density of 10 milliamperes per square centimeter ($mA/cm^2$) were calculated based on the measured luminances, current densities, and voltages in Sections (1) and (2).

(4) Measurement of Lifespan $T_{50}$, which indicates a period of time taken till an initial luminance (assumed as 100%) measured in Section (2) is reduced to 50%, was calculated. $T_{50}$ in Table 10 is a relative lifetime $T_{50}$ to that of the organic light-emitting device of Comparative Example 1.

(5) Measurement of CIE Color Coordinate

CIE color coordinates of the organic light-emitting devices at a luminance of about 500 candelas per square meter ($cd/m^2$) were measured using a luminance meter (Minolta Cs-1000A).

TABLE 10

| Example | Host | Dopant | Driving voltage (V) | Current Efficiency (cd/A) | Luminance (cd/m$^2$) | T$_{50}$ (as relative lifetime) (%) | Color coordinates CIE x | CIE y |
|---|---|---|---|---|---|---|---|---|
| Example 1 | mCP | BD037 | 5.1 | 33.4 | 500 | 312 | 0.17 | 0.26 |
| Example 2 | mCP | BD040 | 5.1 | 33.7 | 500 | 326 | 0.17 | 0.26 |
| Example 3 | mCP | BD044 | 5.1 | 33.5 | 500 | 334 | 0.17 | 0.26 |
| Example 4 | mCP | BD045 | 5.1 | 34.8 | 500 | 350 | 0.17 | 0.26 |
| Example 5 | mCP | BD047 | 5.0 | 32.0 | 500 | 182 | 0.15 | 0.21 |
| Example 6 | mCP | BD049 | 5.1 | 32.4 | 500 | 220 | 0.15 | 0.21 |
| Example 7 | mCP | BD064 | 5.1 | 34.3 | 500 | 341 | 0.17 | 0.26 |
| Example 8 | mCP | BD079 | 5.1 | 34.1 | 500 | 325 | 0.17 | 0.26 |
| Example 9 | mCP | BD098 | 5.1 | 34.0 | 500 | 323 | 0.17 | 0.26 |
| Example 10 | mCP | BD113 | 5.2 | 34.6 | 500 | 339 | 0.17 | 0.26 |
| Example 11 | mCP | BD132 | 5.1 | 33.9 | 500 | 334 | 0.17 | 0.26 |
| Example 12 | mCP | BD151 | 5.1 | 36.5 | 500 | 440 | 0.17 | 0.28 |
| Example 13 | mCP | BD180 | 5.1 | 36.9 | 500 | 455 | 0.17 | 0.27 |
| Example 14 | mCP | BD201 | 5.1 | 36.7 | 500 | 445 | 0.17 | 0.27 |
| Example 15 | mCP | BD233 | 5.0 | 36.9 | 500 | 453 | 0.17 | 0.27 |
| Example 16 | mCP | BD248 | 5.2 | 35.2 | 500 | 378 | 0.17 | 0.27 |
| Example 17 | mCP | BD255 | 5.2 | 35.7 | 500 | 385 | 0.17 | 0.26 |
| Comparative Example 1 | mCP | A | 5.2 | 31.1 | 500 | 100 | 0.17 | 0.26 |

Referring to Table 10, the organic light-emitting devices of Examples 1 to 17 were found to have similar color purity, lower driving voltage, higher current efficiency, and longer lifespans, compared to those of the organic light-emitting device of Comparative Example 1.

As described above, according to the one or more of the above embodiments of the present disclosure, an organometallic compound represented by Formula 1 may have improved optical characteristics, electrical characteristics, and thermal stability. Accordingly, an organic light-emitting device that includes the organometallic compound of Formula 1 or a composition containing the organometallic compound of Formula 1 may have a reduced driving voltage, and improved efficiency, lifespan, and color purity characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present inventive concept have been described with reference to the figures, it will be understood by those of ordinary skill in the art that various changes in form and details may be made therein without departing from the spirit and scope of the present inventive concept as defined by the following claims.

What is claimed is:
1. An organometallic compound represented by Formula 1:

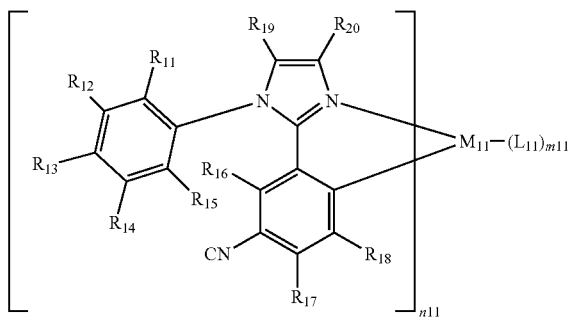

Formula 1 wherein, in Formula 1,
$M_{11}$ is a first-row transition metal, a second-row transition metal, or a third-row transition metal;
$R_{11}$ to $R_{18}$ are each independently a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, or a substituted or unsubstituted $C_1$-$C_{30}$ alkylsilyl group;

optionally, adjacent two of $R_{11}$ to $R_{15}$ are linked to form a substituted or unsubstituted saturated ring, or a substituted or unsubstituted unsaturated ring;

at least one of $R_{11}$ to $R_{15}$ is selected from the group consisting of a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{19}$ and $R_{20}$ are each independently a hydrogen, a deuterium, a $C_1$-$C_{30}$ alkyl group, or a deuterium-substituted $C_1$-$C_{30}$ alkyl group;

at least one of $R_{11}$ to $R_{20}$ is a deuterium-containing substituent;

n11 is 1, 2, or 3;

$L_{11}$ is a monodentate ligand or a bidentate ligand selected from the group consisting of an oxalate, an acetylacetonate, a picolinic acid, a 1,2-bis(diphenylphosphino)ethane, a 1,1-bis(diphenylphosphino)methane, a glycinate, an ethylenediamine, and ligands represented by Formulae 4-1 to 4-4:

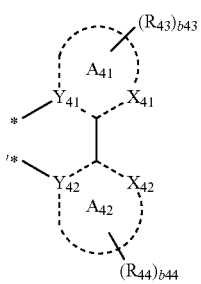

4-1

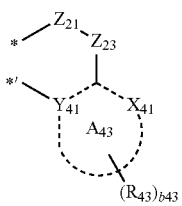

4-2

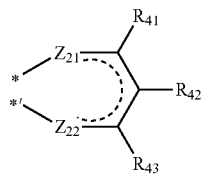

4-3

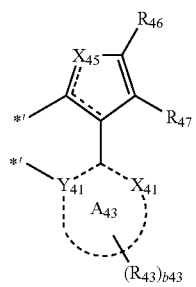

4-4 wherein, in Formulae 4-1 to 4-4, $X_{41}$ is $CR_{41}$ or a nitrogen atom (N);

$X_{42}$ is $CR_{42}$ or N;

$X_{45}$ is O, S, or $N(R_{45})$;

$Y_{41}$ and $Y_{42}$ are each independently C or N;

$Z_{21}$ and $Z_{22}$ are each independently N, O, $N(R_{48})$, $P(R_{48})(R_{49})$, or $As(R_{48})(R_{49})$;

$Z_{23}$ is CO or $CH_2$;

$A_{41}$ to $A_{43}$ are each independently a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, or a non-aromatic condensed heteropolycycle, wherein a bond between $A_{41}$ and $A_{42}$ in Formula 4-1 is a carbon-carbon bond;

$R_{41}$ to $R_{49}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{30}$ arylalkyl group, a substituted or unsubstituted $C_1$-$C_{60}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, or —Si($Q_{41}$)($Q_{42}$)($Q_{43}$);

optionally, adjacent two of $R_{41}$ to $R_{44}$ are linked to form a substituted or unsubstituted saturated ring, or a substituted or unsubstituted unsaturated ring;

optionally, $R_{46}$ and $R_{47}$ are linked to form a substituted or unsubstituted saturated ring or a substituted or unsubstituted unsaturated ring;

b43 and b44 are each independently an integer of 1 to 5;

$Q_{41}$ to $Q_{43}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, a monovalent non-aromatic condensed polycyclic group, or a monovalent non-aromatic condensed heteropolycyclic group; and

* and *′ are each independently a binding site to $M_{11}$ in Formula 1; and m11 is 0, 1, 2, 3, or 4.

2. The organometallic compound of claim 1, wherein $M_{11}$ is Ir or Pt.

3. The organometallic compound of claim 1, wherein $R_{11}$ to $R_{18}$ are each independently a hydrogen, a deuterium, —F, —Cl, —Br, —I, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, or a substituted or unsubstituted $C_1$-$C_{30}$ alkylsilyl group, wherein optionally, adjacent two of $R_{11}$ to $R_{15}$ are linked to form a substructure represented by Formula 10:

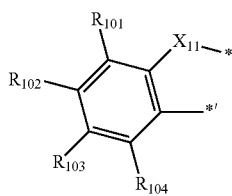

Formula 10 wherein, in Formula 10, $X_{11}$ is O, S, or N($R_{105}$);

$R_{101}$ to $R_{105}$ are each independently a hydrogen, a deuterium, —F, —Cl, —Br, —I, a cyano group, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, or a substituted or unsubstituted $C_1$-$C_{30}$ alkylsilyl group; and

* and *′ are each independently a carbon atom to which adjacent two of $R_{11}$ to $R_{15}$ are bound.

4. The organometallic compound of claim 1, wherein $R_{11}$ to $R_{18}$ are each independently a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, —Si($Q_1$)($Q_2$)($Q_3$), a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, a cyano group, a phenyl group, a biphenyl group, a terphenyl group, a naphthyl group, a phenanthrenyl group, an anthracenyl group, a triphenylenyl group, a pyrenyl group, and a chrysenyl group, each substituted with at least one of a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, or —Si($Q_4$)($Q_5$)($Q_6$), wherein $Q_1$ to $Q_3$ are each independently a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, or a tert-pentyl group; and $Q_4$ to $Q_6$ are each independently a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, or a tert-pentyl group, each substituted with at least one selected from the group consisting of a deuterium, —F, —Cl, —Br, —I, and a cyano group, wherein at least one of $Q_4$ to $Q_6$ is selected from the group consisting of a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, and a cyano group; and optionally, adjacent two of $R_{11}$ to $R_{15}$ are linked to form a substructure represented by Formula 10:

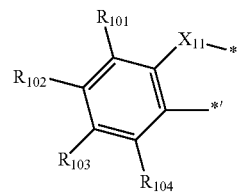

Formula 10 wherein, in Formula 10, $X_{11}$ is O, S, or $N(R_{105})$;

$R_{101}$ to $R_{105}$ are each independently a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, or a chrysenyl group; and

* and *' are each independently a carbon atom to which adjacent two of $R_{11}$ to $R_{15}$ are bound.

5. The organometallic compound of claim 1, wherein at least one of $R_{11}$ to $R_{15}$ is selected from the group consisting of a substituted or unsubstituted $C_3$-$C_{30}$ branched alkyl group, a substituted or unsubstituted $C_6$-$C_{30}$ aryl group, a substituted or unsubstituted $C_1$-$C_{30}$ heteroaryl group, and a substituted or unsubstituted $C_1$-$C_{30}$ alkylsilyl group, and optionally, adjacent two of $R_{11}$ to $R_{15}$ are linked to form a substructure represented by Formula 10:

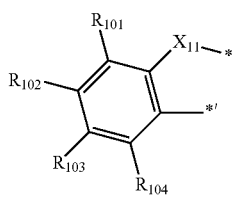

Formula 10 wherein, in Formula 10, $X_{11}$ is O, S, or $N(R_{105})$;

$R_{101}$ to $R_{105}$ are each independently a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_1$-$C_{30}$ heteroaryl group, or a substituted or unsubstituted $C_1$-$C_{30}$ alkylsilyl group;

* and *' are each independently a carbon atom to which adjacent two of $R_{11}$ to $R_{15}$ are bound.

6. The organometallic compound of claim 1, wherein at least one of $R_{11}$ to $R_{15}$ is selected from the group consisting of an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, —Si($Q_1$)($Q_2$)($Q_3$), an iso-propyl group, a sec-butyl group, an iso-butyl group, a tert-butyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I, a cyano group, a phenyl group, a biphenyl group, a terphenyl group, a naphthyl group, a phenanthrenyl group, an anthracenyl group, a triphenylenyl group, a pyrenyl group, and a chrysenyl group, each substituted with at least one of a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, and —Si($Q_4$)($Q_5$)($Q_6$), wherein $Q_1$ to $Q_3$ are each independently a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, or a tert-pentyl group;

$Q_4$ to $Q_6$ are each independently a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, each substituted with at least one selected from the group consisting of a deuterium, —F, —Cl, —Br, —I, and a cyano group;

at least one of $Q_4$ to $Q_6$ is selected from the group consisting of a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, —I and a cyano group; and optionally, adjacent two of $R_{11}$ to $R_{15}$ are linked to form a substructure represented by Formula 10:

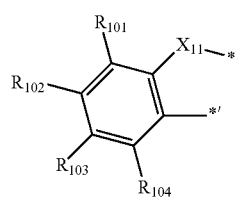

Formula 10 wherein, in Formula 10, $X_{11}$ is O, S, or $N(R_{105})$;

$R_{101}$ to $R_{105}$ are each independently a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, or a chrysenyl group;

* and *' are each independently a carbon atom to which adjacent two of $R_{11}$ to $R_{15}$ are bound.

7. The organometallic compound of claim 1, wherein at least one of $R_{11}$ to $R_{15}$ is selected from the group consisting of an iso-propyl group, an iso-butyl group, a tert-butyl group, a neo-pentyl group, a phenyl group, a biphenyl group, —Si(CH$_3$)$_3$, an iso-propyl group, an iso-butyl group, a tert-butyl group, a neo-pentyl group, each substituted with a deuterium, a phenyl group, a biphenyl group, each substituted with a deuterium, and Si(CD$_3$)$_3$, and optionally, $R_{12}$ and $R_{13}$ are linked to form a substructure represented by Formula 10:

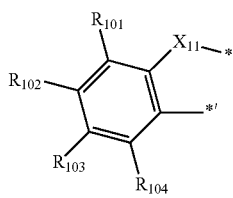

Formula 10 wherein, in Formula 10, $X_{11}$ is O, S, or N($R_{105}$);

$R_{101}$ to $R_{105}$ are each independently a hydrogen, a deuterium, —F, —Cl, —Br, —I, a cyano group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, or a chrysenyl group; and

* and *' are each independently a carbon atom to which adjacent two of $R_{11}$ to $R_{15}$ are bound.

8. The organometallic compound of claim 1, wherein $R_{19}$ is a deuterium and $R_{20}$ is a hydrogen; $R_{19}$ is a hydrogen and $R_{20}$ is a deuterium; or $R_{19}$ and $R_{20}$ are both deuterium.

9. The organometallic compound of claim 1, wherein the deuterium-containing substituent is a deuterium, or a $C_1$-$C_{30}$ alkyl group, a $C_3$-$C_{30}$ branched alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_7$-$C_{30}$ arylalkyl group, a $C_1$-$C_{30}$ heteroaryl group, a $C_2$-$C_{30}$ heteroaryloxy group, a $C_2$-$C_{30}$ heteroarylthio group, a $C_3$-$C_{30}$ heteroarylalkyl group, a monovalent non-aromatic condensed polycyclic group, a monovalent non-aromatic condensed heteropolycyclic group, or a $C_1$-$C_{30}$ alkylsilyl group, each substituted with a deuterium.

10. The organometallic compound of claim 1, wherein the deuterium-containing substituent is a deuterium, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a phenyl group, a biphenyl group, a terphenyl group, a naphthyl group, a phenanthrenyl group, an anthracenyl group, a triphenylenyl group, a pyrenyl group, a chrysenyl group, each substituted with a deuterium, or —Si(Q$_4$)(Q$_5$)(Q$_6$), wherein $Q_4$ to $Q_6$ are each independently a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, a tert-pentyl group, a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with at least one of a deuterium, —F, —Cl, —Br, or a cyano group; and at least one of $Q_4$ to $Q_6$ is selected from the group consisting of a methyl group, an ethyl group, an n-propyl group, an iso-propyl group, an n-butyl group, a sec-butyl group, an iso-butyl group, a tert-butyl group, an n-pentyl group, an iso-pentyl group, a 1-methylbutyl group, a 2-methylbutyl group, a neo-pentyl group, a 1,2-dimethylpropyl group, and a tert-pentyl group, each substituted with a deuterium.

11. The organometallic compound of claim 1, wherein the deuterium-containing substituent is -D, —CH$_2$D, —CHD$_2$, —CD$_3$, —CH$_2$CH$_2$D, —CH$_2$CHD$_2$, —CH$_2$CD$_3$, —CHDCH$_3$, —CHDCH$_2$D, —CHDCHD$_2$, —CHDCD$_3$, —CD$_2$CH$_3$, —CD$_2$CH$_2$D, —CD$_2$CHD$_2$, —CD$_2$CD$_3$, —CH$_2$CH$_2$CH$_2$D, —CH$_2$CH$_2$CHD$_2$, —CH$_2$CH$_2$CD$_3$, —CH$_2$CHDCH$_3$, —CH$_2$CHDCH$_2$D, —CH$_2$CHDCHD$_2$, —CH$_2$CHDCD$_3$, —CH$_2$CD$_2$CH$_3$, —CH$_2$CD$_2$CH$_2$D, —CH$_2$CD$_2$CHD$_2$, —CH$_2$CD$_2$CD$_3$, —CHDCH$_2$CH$_3$, —CHDCH$_2$CHD$_2$, —CHDCH$_2$CD$_3$, —CHDCHDCH$_3$, —CHDCHDCH$_2$D, —CHDCHDCHD$_2$, —CHDCHDCD$_3$, —CHDCD$_2$CH$_3$, —CHDCD$_2$CH$_2$D, —CHDCD$_2$CHD$_2$, —CHDCD$_2$CD$_3$, —CD$_2$CH$_2$CH$_2$D, —CD$_2$CH$_2$CHD$_2$, —CD$_2$CH$_2$CD$_3$, —CD$_2$CHDCH$_3$, —CD$_2$CHDCH$_2$D, —CD$_2$CHDCHD$_2$, —CD$_2$CHDCD$_3$, —CD$_2$CD$_2$CH$_3$, —CD$_2$CD$_2$CH$_2$D, —CD$_2$CD$_2$CHD$_2$, —CD$_2$CD$_2$CD$_3$, —CH(CH$_3$)(CH$_2$D), —CH(CH$_3$)(CHD$_2$), —CH(CH$_2$D)$_2$, —CH(CH$_3$)(CD$_3$), —CH(CHD)(CHD$_2$), —CH(CH$_2$D)(CD$_3$), —CH(CHD$_2$)$_2$, —CH(CHD$_2$)(CD$_3$), —CH(CD$_3$)$_2$, —CD(CH$_3$)$_2$, —CD(CH$_3$)(CH$_2$D), —CD(CH$_3$)(CHD$_2$), —CD(CH$_2$D)(CH$_2$D), —CD(CH$_3$)(CD$_3$), —CD(CH$_2$D)(CHD$_2$), —CD(CH$_2$D)(CD$_3$), —CD(CHD$_2$)$_2$, —CD(CHD$_2$)(CD$_3$), —CD(CD$_3$)$_2$, —CD$_2$CD(CD$_3$)$_2$, —C(CD$_3$)$_3$, —CD$_2$C(CD$_3$)$_3$, or a group represented by any one of Formulae 3-1 to 3-5:

3-1
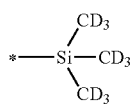

3-2
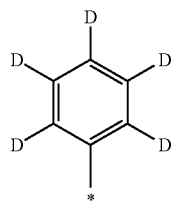

3-3
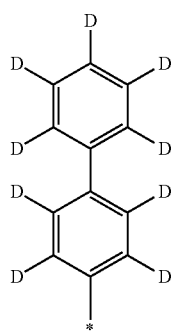

3-4
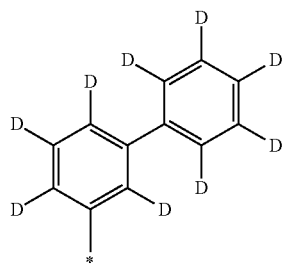

3-5
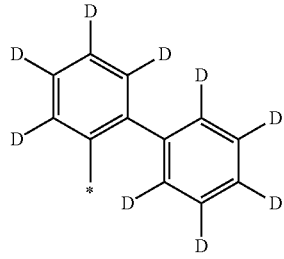

wherein, in Formulae 3-1 to 3-5, * is a binding site to an adjacent atom.

12. The organometallic compound of claim 1, wherein $L_{11}$ is a bidentate ligand.

13. The organometallic compound of claim 1, wherein $M_{11}$ is iridium (Ir); and n11 is 2 or 3.

14. The organometallic compound of claim 1, wherein $M_{11}$ is platinum (Pt); and n11 is 1 or 2.

15. The organometallic compound of claim 1, wherein the organometallic compound of Formula 1 is a compound represented by one of Formulae 1-11 to 1-22:

1-11
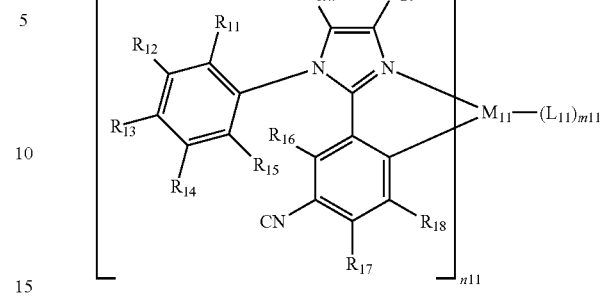

1-12
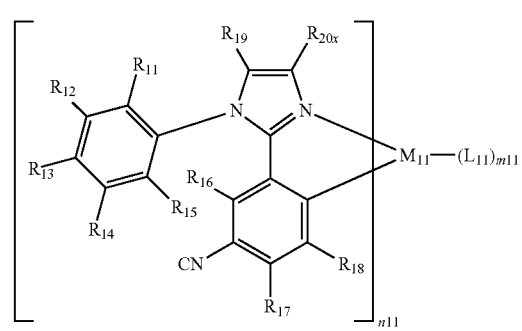

1-13
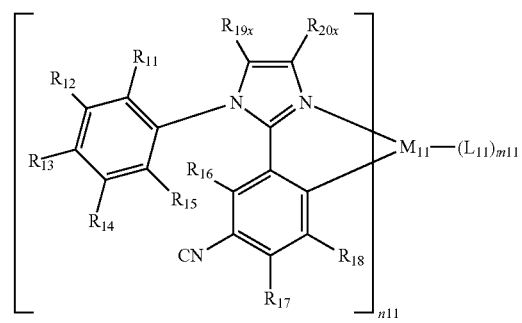

1-14
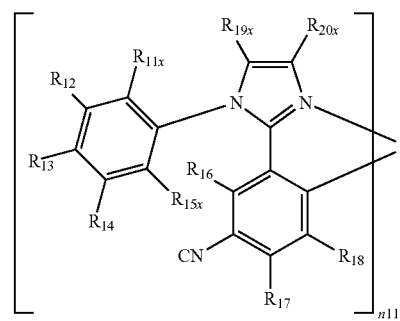

1-15

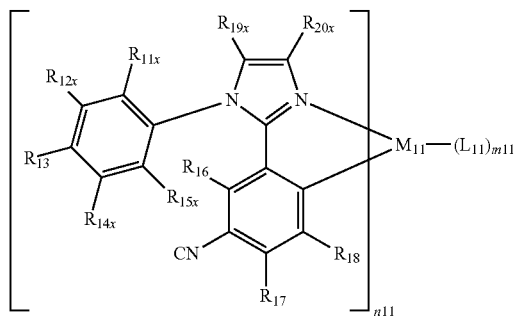

1-16

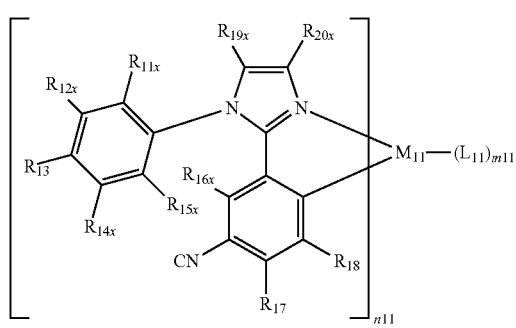

1-17

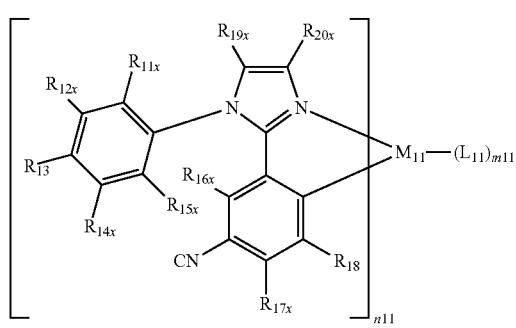

1-18

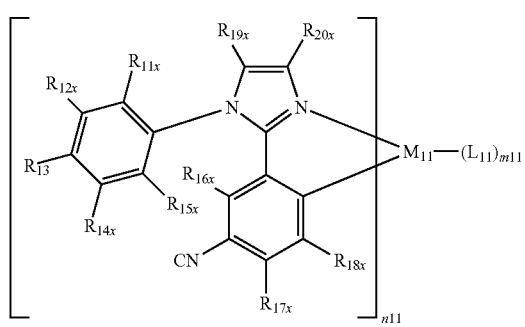

1-19

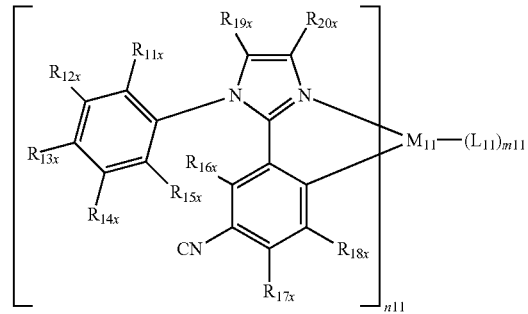

1-20

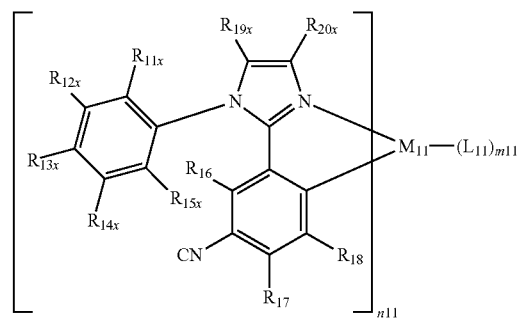

1-21

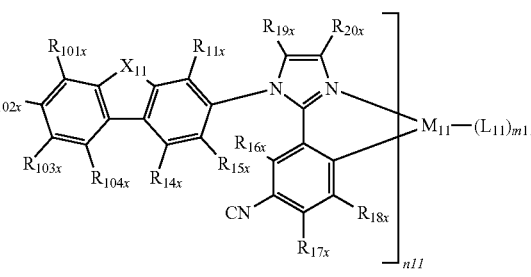

1-22

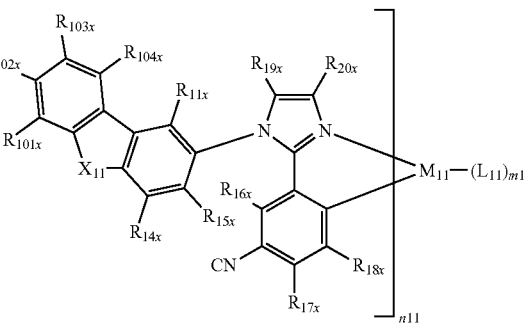

wherein, in Formulae 1-11 to 1-22, $M_{11}$, $R_{11}$ to $R_{20}$, $n_{11}$, $L_{11}$, and m11 are defined the same as those in Formula 1;

$X_{11}$ is O, S, or $N(R_{105})$;

$R_{101}$ to $R_{105}$ are each independently a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_3$-$C_{30}$ branched alkyl group, a substituted or unsubstituted $C_6$-$C_{30}$ aryl group, a substituted or unsubstituted $C_1$-$C_{30}$ heteroaryl group, or a substituted or unsubstituted $C_1$-$C_{30}$ alkylsilyl group; and $R_{11x}$, $R_{12x}$, $R_{13x}$, $R_{14x}$, $R_{15x}$, $R_{16x}$, $R_{17x}$, $R_{18x}$, $R_{19x}$, $R_{20x}$, $R_{101x}$, $R_{102x}$, $R_{103x}$, and $R_{104x}$ are each independently a deuterium-containing substituent.

16. An organometallic compound-containing composition comprising a first organometallic compound represented by Formula 1 and a second organometallic compound represented by Formula 2:

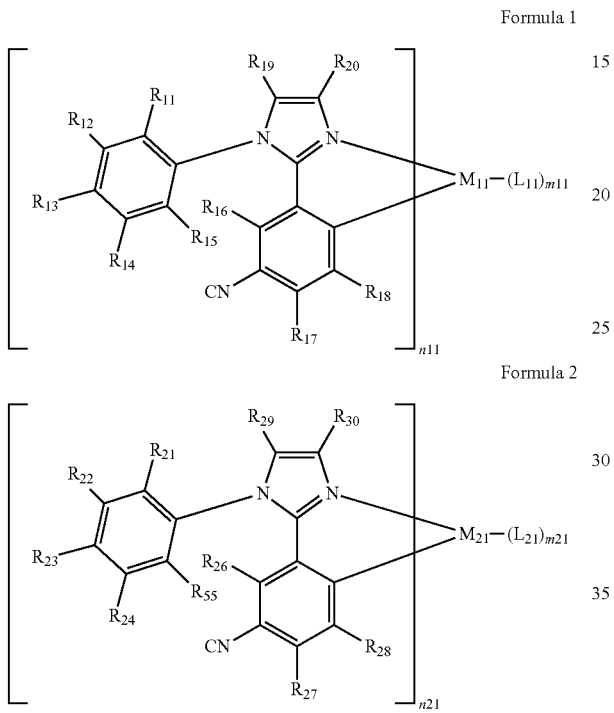

wherein, in Formulae 1 and 2, $R_{11}$ to $R_{18}$ are each independently a hydrogen, a deuterium, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, or a substituted or unsubstituted $C_1$-$C_{30}$ alkylsilyl group;

optionally, adjacent two of $R_{11}$ to $R_{15}$ are linked to form a substituted or unsubstituted saturated ring, or a substituted or unsubstituted unsaturated ring;

at least one of $R_{11}$ to $R_{15}$ is a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, or a substituted or unsubstituted $C_1$-$C_{30}$ alkylsilyl group;

$R_{19}$ and $R_{20}$ are each independently a hydrogen, a deuterium, a $C_1$-$C_{30}$ alkyl group, or a deuterium-substituted $C_1$-$C_{30}$ alkyl group;

at least one of $R_{11}$ to $R_{20}$ is a deuterium-containing substituent;

$R_{21}$ to $R_{28}$ are each independently a hydrogen, —F, —Cl, —Br, —I, a hydroxyl group, a cyano group, a nitro group, a carbonyl group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_3$-$C_{30}$ branched alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, or a substituted or unsubstituted $C_1$-$C_{30}$ alkylsilyl group;

optionally, adjacent two of $R_{21}$ to $R_{25}$ are linked to form a substituted or unsubstituted saturated ring, or a substituted or unsubstituted unsaturated ring;

at least one of $R_{21}$ to $R_{25}$ is selected from the group consisting of a substituted or unsubstituted $C_3$-$C_{30}$ branched alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, a substituted or unsubstituted monovalent non-aromatic condensed polycyclic group, a substituted or unsubstituted monovalent non-aromatic condensed heteropolycyclic group, and a substituted or unsubstituted $C_1$-$C_{30}$ alkylsilyl group;

$R_{29}$ and $R_{30}$ are each independently a hydrogen or a $C_1$-$C_{30}$ alkyl group;

$R_{21}$ to $R_{30}$ are each a substituent containing no deuterium;

$M_{11}$ and $M_{21}$ are each independently a first-row transition metal, a second-row transition metal, or a third-row transition metal;

n11 and n21 are each independently 1, 2, or 3;

$L_{11}$ and $L_{21}$ are each independently a monodentate ligand or a bidentate ligand; and m11 and m21 are each independently 0, 1, 2, 3, or 4.

17. The organometallic compound-containing composition of claim 16, wherein the organometallic compound-containing composition has a deuteration rate of 50% or more, wherein the deuteration rate is represented by Equation 2:

$$\text{Deuteration rate } (\%) = n_{D2}/(n_{H2} + n_{D2}) \times 100 \qquad \text{Equation 2}$$

wherein, in Equation 2, $n_{H2}$ represents a sum of a total number of hydrogens in the deuterium-containing substituents and a total number of hydrogens in substituents that are equivalent to the deuterium-containing substituents; and $n_{D2}$ represents a total number of deuterium atoms in the deuterium-containing substituents.

18. An organic light-emitting device comprising:
a first electrode;
a second electrode; and
an organic layer disposed between the first electrode and the second electrode,
wherein the organic layer comprises an emission layer and the organometallic compound of claim 1.

19. The organic light-emitting device of claim 18, wherein the emission layer comprises the organometallic compound or the organometallic compound-containing composition,
wherein the emission layer further comprises a host, and
wherein the organometallic compound in the emission layer is a dopant.

20. An organic light-emitting device comprising:
a first electrode;
a second electrode; and
an organic layer disposed between the first electrode and the second electrode,
wherein the organic layer comprises an emission layer and the organometallic compound-containing composition of claim 16.

21. The organic light-emitting device of claim 20, wherein the emission layer comprises the organometallic compound-containing composition,
wherein the emission layer further comprises a host, and
wherein each of the first organometallic compound and the second organometallic compound in the emission layer is a dopant.

22. The organometallic compound of claim 1, wherein m11 is 0.

* * * * *